(12) United States Patent
McGregor et al.

(10) Patent No.: US 9,898,513 B2
(45) Date of Patent: Feb. 20, 2018

(54) SYSTEM, METHOD AND COMPUTER PROGRAM FOR MULTI-DIMENSIONAL TEMPORAL AND RELATIVE DATA MINING FRAMEWORK, ANALYSIS AND SUB-GROUPING

(71) Applicant: UNIVERSITY OF ONTARIO INSTITUTE OF TECHNOLOGY, Oshawa (CA)

(72) Inventors: Carolyn Patricia McGregor, Brooklyn (CA); Kathleen Patricia Smith, Oshawa (CA); Agam Dhanoa, Mississauga (CA)

(73) Assignee: UNIVERSITY OF ONTARIO INSTITUTE OF TECHNOLOGY

( * ) Notice: Subject to any disclaimer, the term of this patent is extended or adjusted under 35 U.S.C. 154(b) by 97 days.

(21) Appl. No.: 14/363,385

(22) PCT Filed: Dec. 12, 2012

(86) PCT No.: PCT/CA2012/001139
§ 371 (c)(1),
(2) Date: Jun. 6, 2014

(87) PCT Pub. No.: WO2013/086610
PCT Pub. Date: Jun. 20, 2013

(65) Prior Publication Data
US 2014/0358926 A1 Dec. 4, 2014

Related U.S. Application Data

(60) Provisional application No. 61/569,316, filed on Dec. 12, 2011.

(51) Int. Cl.
*G06F 17/30* (2006.01)
*G06F 19/24* (2011.01)
*G06F 19/00* (2018.01)

(52) U.S. Cl.
CPC .. *G06F 17/30539* (2013.01); *G06F 17/30516* (2013.01); *G06F 17/30551* (2013.01);
(Continued)

(58) Field of Classification Search
None
See application file for complete search history.

(56) References Cited

U.S. PATENT DOCUMENTS

2002/0161763 A1 10/2002 Ye et al.
2004/0024773 A1 2/2004 Stoffel et al.
(Continued)

FOREIGN PATENT DOCUMENTS

WO 2011009211 A1 1/2011
WO WO 2011009211 A1 * 1/2011 ......... G06F 19/3443

OTHER PUBLICATIONS

WIPO, International Search Report and Written Opinion for PCT Application No. PCT/CA2012/001139 dated Apr. 10, 2013.
(Continued)

*Primary Examiner* — Alex Gofman
*Assistant Examiner* — Umar Mian
(74) *Attorney, Agent, or Firm* — Norton Rose Fulbright Canada LLP

(57) ABSTRACT

The present invention relates to a system, method and computer program product that is a multi-dimensional data mining environment and that operable to apply a series of temporal and relative rules (i.e., STDM"0) and is further operable in at least one of the following ways: to incorporate a framework to support temporal abstractions and relative alignments to data (i.e., STDM"0); and to derive characteristics within the data (STDM"0). The present invention may incorporate data from multiple sources, and potentially multiple centers. The analysis and alignment of the data may involve both temporal dimensions and other dimensions (or
(Continued)

FIG.22 relative aspects) of the data. The present invention may further be a data mining environment that is flexible enough to permit relatively open ended queries thereby enabling, for example, the detection of trends, including trends with new dimensions, or trends based on relatively small data sets.

19 Claims, 32 Drawing Sheets

(52) U.S. Cl.
CPC .......... *G06F 19/322* (2013.01); *G06F 19/345* (2013.01); *G06F 19/3418* (2013.01); *G06F 19/3443* (2013.01); *G06F 2216/03* (2013.01)

(56) References Cited

U.S. PATENT DOCUMENTS

| | | |
|---|---|---|
| 2007/0226212 A1 | 9/2007 | Aggarwal et al. |
| 2007/0239753 A1 | 10/2007 | Leonard et al. |
| 2010/0030418 A1 | 2/2010 | Holland et al. |
| 2010/0076785 A1 | 3/2010 | Mehta et al. |
| 2015/0200815 A1* | 7/2015 | Verkasalo ......... G06F 17/30867 707/740 |

OTHER PUBLICATIONS

Carolyn McGregor et al., Multi-dimensional temporal abstraction and data mining of medical time series data: Trends and challenges, 30th Annual International IEEE EMBS Conference, Aug. 20-24, 2008.

SIPO, Notification of the First Office Action for CN Application No. 2012800694967 dated Dec. 12, 2016.

IP Australia, Examination Report No. 1 for AU Application No. 2012350398 dated Jun. 8, 2017.

* cited by examiner

| Systems | Environment | Freq. | Multiple Streams? | Real-time? | Privacy | Dist. Abst. | Locations | TA Deployment |
|---|---|---|---|---|---|---|---|---|
| Asgaard I Shahar et al. 1998 | NICU - Abstractions for therapeutic plans | Can only handle low frequency data - Based on RÉSUMÉ | No | No | No | No | Single Site | Yes |
| RASTA I O'Connor et. al. 2002 | Knowledge-driven monitoring of clinical databases | Low frequency data - Uses EON - Based on RÉSUMÉ | Parallelizable and Distributable | No | No | Based on abstraction hierarchy (an abstraction tree for each patient) – focus on memory | Single Site | Yes |
| Idan I Boaz and Shahar, 2005 | Integration of data and knowledge in clinical practice | Low frequency retrospective data + data form domain experts | No | No | No | TA mediator for time oriented data sources + domain specific knowledge sources + vocabulary servers | Single Site | Yes |
| Mariposa I Stonebaker et. al. 1996 | unify disparate approaches of distributed database management systems - IT Environment | Not applicable - distributing data over a number of sites that can be connected (WAN or LAN) | None - Focus on database management not clinical data | Yes - rule processor which watches for events of interest (pre-determined and programmed) | No | None but rule processor discussed for real time analysis | Distributed | No |

FIG. 10

SYSTEM, METHOD AND COMPUTER PROGRAM FOR MULTI-DIMENSIONAL TEMPORAL AND RELATIVE DATA MINING FRAMEWORK, ANALYSIS AND SUB-GROUPING

FIELD OF THE INVENTION

The present invention relates generally to data mining. The present invention relates more specifically to data mining environments that support a framework to run temporal abstractions and relative alignments.

BACKGROUND OF THE INVENTION

There are numerous areas of invention wherein multiple devices generate multiple data streams, and it is therefore desirable to utilize the data streams for the purpose of monitoring, analyzing and/or predicting behaviour that is time dependent. This time dependency, across multiple data streams can be difficult to resolve, part milady for the purposes of analysis, using existing data mining environments.

Faced with an exponential amount of data, many organizations are turning to data mining to translate data into information that can be utilized to generate subsequent knowledge. In particular distributed data mining, which refers to the mining of distributed data sets which are often stored in local databases and hosted by local computers connected through a network, is utilized in the prior art. Notably, many environments have different distributed sources of capacious data, the analysis of which requires data mining technology specific to distributed applications. Medical data is often distributed due to concerns of security, privacy and confidentiality of patient information. For these reasons, medical data is likely to maintain its distributed nature in the future. In distributed data mining, the data mining occurs both at a local level and a central level. At the global level, local data mining results are combined to discover global patterns or themes present in the data.

As an example of a situation wherein multiple data sources are utilized, intensive care units worldwide use a range of medical monitoring equipment, such as medical devices for life support and critical monitoring. Many of these devices have been operational for over 50 years. Although the devices themselves may have evolved over time, generally these devices enable critically ill medical and surgical patients to be observed and treated in a complex, specialized environment by physicians and nurses trained in restoring and/or maintaining the function of vital organs. A diverse range of such devices display physiological data and many have the ability to output this data via serial, USB or other ports.

In addition to the collection of this data for use in real-time by care providers, it is desirable to enable secondary analysis of the data for other related clinical research. For example, such secondary analysis can enable the discovery of previously unknown trends and patterns that may be indicative of the onset of some condition. The potential for such secondary use of health data is significant. In an American Medic al Informatics Association White Paper published in the Journal of the American Medical Informatics Association in 2007, entitled "Toward a National Framework for the Secondary Use of Health Data", the urgency for infrastructures to support the secondary use of data in today's data intensive healthcare environment is characterized as pivotal to the U.S. Health system.

PCT Application No. PCT/CA2010/001148 discloses a multi-dimensional temporal abstraction and data mining technology, the method comprising: collecting and optionally cleaning multi-dimensional data, the multi-dimensional data including a plurality of data streams; temporally abstracting the multi-dimensional data; and relatively aligning the temporally abstracted multi-dimensional data based on an at least one time point of interest.

The work of Abdel-Rahman, Jeremic and Tan(2009) (cited below) test 3 two types of models namely, empirical Bayesian and autoregressive moving average to determine future state of the same stream. The present invention proposes a method to perform research to determine an association with an seemingly independent event from the streams and other entity data that is analyzed.

The work of Apiletti et al (2009) (cited below) proposes an approach for temporal analysis that does not support sub classification for classification based on entity attributes such as patient characteristics, as in the case of healthcare. Further, the research does not propose a platform to perform multiple studies.

Studies such as Krueger et al (2010) (cited below) use traditional signal processing techniques on physiological data streams to perform statistical analysis of the heart rate variability temporal feature as derived from the electrocardiogram (ECG) signal to confirm a notion of different patterns when grouped by age, however the temporal resultant features were not made explicit and are not translational for real-time observation.

A Data warehouse model for healthcare to support data mining is proposed by Lyman (2008) (cited below) however that model does not include the data model or data mining techniques for data streams such as physiological data streams or other data streams in healthcare.

Okascharoen et al (2007) (also cited below) propose a bedside predict on score for diagnosis of late-onset neonatal sepsis and in that work validate it with newly collected. While the score incorporates the assessment of some clinical conditions (apnea/bradycardia), these conditions are deemed as present through traditional electronic health record charting of occurrence rather than real-time temporal abstraction profiling of the physiological streams to better understand the temporal behaviours in the streams.

In Sharek (2006) (cited below) a NICU-focused tool for adverse event detection is proposed and tested. The adverse events relate to drug dosages. However the event detection is not via analysis of data streams but rather chart review. This invention enables the integration of drug information as data streams for example from the infusion pumps.

Verduijn et al (2007) (cited below) propose two temporal abstraction procedures for the extraction of meta features from medical data streams to enable the discovery of new abstractions or the use of abstractions from existing knowledge, however the method of extraction is not part of an overall architecture to support multiple studies and they focus on the proposition of specific approaches for both forms of temporal abstraction. In the present invention, temporal abstractions can be learned through exploratory mining for validation through explanatory mining or they can be defined by a domain expert for explanatory mining testing only. In addition, in the present invention, the data representation of the abstractions directly correlates with the manner with which these abstractions could then be observed in real-time for future real-time condition/event onset detection.

Zhang (2007) and Zhang and Szolovits (2008) (cited below) propose a method for patient-specific real time adaptive monitoring in critical care. In that work 8 hours of training data is required to train the model on the current state of the patient from which deviations can be detected. There was no automated systemic approach to data collection. A trained observer annotated data and a laptop computer was connected during the study windows to collect the data. The stream data was not assessed based on temporal features correlating to a rule set. In the present invention, a systemic approach to longitudinal multi-dimensional data stream capture is proposed and the assessment of the data is based on the construction of temporal features either as simple or complex temporal features.

Griffin and Moorman (2001) (cited below) propose a method for the early diagnosis of neonatal sepsis and sepsis-like illness using novel heart rate analysis. That method uses the analysis of ECG only and performs feature extraction based on the presence of heart rate variability. The method of extraction is not part of an overall architecture to support multiple studies. The method does not support multi-dimensional data analysis. The present invention proposes a method to perform a study such as that detailed. It proposed an approach to define the temporal abstractions that are the results from this study. It enables the completion of this study together with other studies. It supports a systemic approach for the collection of data streams and other static data to support the research.

The following include references that may be pertinent to the present invention, including references referred to above.

Abdel-Rahman, Y., Jeremic, A., & Tan, K. (2009). Neonate Heart Rate Prediction. 31st Annual International Conference of the IEEE EMBS (pp. 4695-4698). Minneapolis, Minn., USA; IEEE.

Apiletti, D., Barelis, E., Bruno, G., & Cerquitelli, T. (May 2009). Real-Time Analysis of Physiological Data to Support Medical Applications. Information Technology in Biomedicine, Vol. 13, No. 3, pg. 313-321.

Bjering, H., & McGregor, C. (2010). A Multi-dimensional Temporal Abstractive Data Mining Framework. Proc. 4th Australasian Workshop on Health Informatics and Knowledge Management (pp. Conferences in Research and Practice in Information Technology Vol. 108 pg. 29-38). Brisbane, Australia: Copyright © 2010, Australian Computer Society, Inc.

Blount, M., Ebling, M. R., Eklund, J. M., James, A. G., McGregor, C., Percival, N., et al. (2010). Real-Time Analysis for Intensive Care—Development and Deployment of the Artemis Analytic System. IEEE Engineering in Medicine and Biology Magazine, 110-118.

Catley, C., Smith, K., McGregor, C., & Tracy, M. (2009). Extending CRISP-DM to incorporate temporal data mining of multi-dimensional medical data streams: A neonatal intensive care unit case study. 22nd IEEE International Symposium on Computer-Based Medical Systems, 2009 (pp. 1-5). Albuquerque, N. Mex.: IEEE.

Catley, C., Smith, K., McGregor, C., James, A., & Eklund, J. M. (2010). A Framework to Model and Translate Clinical Rules to Support Complex Real-time Analysis of Physiological and Clinical Data. IHI '10. Arlington, Va., USA.: 2010 ACM.

Eklund, J. M., McGregor, C., & Smith, K. (2008). A Method for Physiological Data Transmission and Archiving to Support the Service of Critical Care Using DICOM and HL7. IEEE EMBS conference. Vancouver.

Griffin, P., & Moorman, R. (2001). Toward the early diagnosis of neonatal sepsis and sepsis-like illness using novel heart rate analysis. Pediatrics, vol. 107, no. 1, pp. 97-104.

Heath, J. (2006). A Framework for an Intelligent Decision Support System (IDSS) Including a Data Mining Methodology, for Fetal-Maternal Clinical Practice and Research. School of Computing and Mathematics. Sydney, University of Western Sydney, Australia, Ho, T., Kawaski, S., Quang, L., Takabayashi, K., & Yokoi, H. (2004). Combining Temporal Abstraction and Data Mining to Study Hepatitis Data. SIG-KBS.

Holmes, H. J. (2007). Intelligent data analysis in biomedicine. Journal of Biomedical Informatics, 40: 605-608.

Kamaleswaran, R., McGregor, C., & Eklund, J. M. (2010). A Method for Clinical and Physiological Event Stream Processing. 32nd Annual International IEEE EMBS Conference (p. 4). Buenos Aires, Argentina: IEEE.

Krueger, C., van Oostrom, J. H., & Shuster, J. (2010). A longitudinal Description of Heart Rate Variability in 25-34-Week-Old Preterm Infants. Biological Research for Nursing, 11(3) 261-268.

Lyman J., S. K. (2008). The Development of Health Care Data Warehouses to Support Data Mining. Clin Lab Med, 28: 55-71.

McGregor, C. P. (July 2010), Patent No. 089705-0009. Canada, Gatineau Quebec.

McGregor, C., Purdy, M., & Kneale, B. (2005). Compression of XML Physiological Data Streams to Support Neonatal Intensive Care Unit Web Services. IEEE International Conference on e-Technology, e-Commerce, and e-Service (pp. 486-489). Hong Kong: IEEE.

Okascharoen, C., Hui, C., Caimie, J., Morris, A. M., & Kirpalani, H. (2007). External validation of bedside prediction score for diagnosis of late-onset neonatal sepsis. Journal of Perinatology, 496-501.

Sharek, P. J., Horbar, J. D., Mason, W., Bisarya, H., Thurm, C. W., Suresh, G., et al. (2006). Adverse Events in the Neonatal Intensive Care Unit: Development, Testing, and Findings of an NICU-Focused Trigger Tool to Identify Harm in North American NICUs. PEDIATRICS—Official Journal of the American Academy of Pediatrics, 1332-1340.

Stacey, M., McGregor, C., & al., e, (2007), An Architecture for Multi Dimensional Temporal Abstraction and its Application to Support Neonatal Intensive Care. Engineering in Medicine and Biology Society. IEEE/EMB.

Tong, C., Sharma, D., & Shadabi, F. (2008). A Multi-Agents Approach to Knowledge Discovery. IEEE/WIC/ACM conference.

Verduijin, M., Sacchi, L., Peek, N., Bellazzi, R., de Jonge, E., & de Mol B. (2007). temporal abstraction for feature extraction: A comparative case study in prediction from intensive care monitoring data. Artificial Intelligence in Medicine, 41: 1-12.

Zhang Y, & Szolovits, P. (2008). Patient-specific learning in real time for adaptive monitoring in critical care. Journal of Biomedical Informatics, 41: 452-460.

Zhang, Y. (2007). Real-time Development of Patient-specific Alarm Algorithms for critical care. IEEE EMBS conference.

There is a need for computer systems, methods and computer programs for execution on computer systems, that address the requirements mentioned above.

SUMMARY OF THE INVENTION

The present invention provides a system, method and computer program for multi-dimensional temporal data mining.

The present invention provides a method for multi-dimensional temporal abstraction and data mining, the method characterized by: collecting and optionally cleaning multi-dimensional data, the multi-dimensional data including a plurality of data streams; temporally abstracting the multi-dimensional data; relatively aligning the temporally abstracted multi-dimensional data based on an at least one time point of interest; and managing the distribution of temporal rules and relative rules across multiple sites in order to support multi-dimensional, multi-site data mining operations based on the aligned temporal data.

In one aspect, a computer implemented data mining method for mining data streams from multiple sites is provided, wherein different attributes may be associated with data streams, characterized by: using a central distribution computer system component to store a series of temporal rules and relative rules for relatively aligning multi-dimensional data based on at least one time point of interest, the central distribution computer system when executed determining particular temporal rules applicable to data associated with a particular site, based on the different attributes; collecting at the multiple sites, and optionally cleaning, multi-dimensional data, the multi-dimensional data including a plurality of data streams; temporally abstracting the multi-dimensional data by accessing and applying the applicable temporal rules so as to generate temporally abstracted multi-dimensional data, and relatively aligning the temporally abstracted multi-dimensional data based on an at least one time point of interest by accessing and applying the applicable relative rules; and collecting temporally abstracted and relatively aligned data from the multiple sites to provide multi-dimensional, temporal, multi-site data for use in data mining operations.

In another aspect, the method comprises managing the distribution and application of the temporal rules and the relative rules across the multiple sites in a way that supports data mining operations across the multiple sites in real time or near real time. In another aspect, the different attributes may include one or more of: (a) data structure, (b) data collection frequency, or (c) the type of device collecting the data (including manufacturer/model, approach of device to data correction or mechanism for identifying artefacts in signals).

In another aspect, the method comprises distributing applicable temporal rules and applicable relative rules based on the attributes associated with the relevant data streams.

In a further aspect, each data stream relates to a human subject, and the central distribution computer system when executed (a) initiates creation of simple abstractions for each human subject, and storage of the simple abstractions locally at each site, and tagging of the data streams using site identification data, and (b) initiates creation of complex abstractions using the applicable temporal rules and tagging of the complex abstractions with tagging information defined by the central distribution computer system so as to enable access for multi-site data mining operations initiated by the central distribution computer system.

In another aspect, the method comprises generation of patient monitoring data in real time or near real time for use in connection with one or more patient care systems or patient monitoring systems.

In a still other aspect, each data stream is associated with a particular human subject, and comprises dynamically defining groups or sub-groups of human subjects, or characteristics associated with such groups or sub-groups, and enabling data mining operations in real time or near real time based on such groups or sub-groups.

In a still other aspect, a data mining computer system for mining data from multiple sites is provided, wherein different attributes may be associated with data streams, the system comprising a central distribution computer system component to store a series of temporal rules and relative rules for relatively aligning multi-dimensional data based on at least one time point of interest, the central distribution computer system when executed determining particular temporal rules applicable to data associated to a particular site; one or more devices associated with two or more sites, the devices collecting data in a plurality of data streams; and at least one local computer at each site connected to central distribution computer system; wherein: the central distribution when executed manages the temporal abstraction and relative alignment of the data streams so as to support data mining operations for multi-dimensional data across the multiple sites by: accessing from the local computer information regarding the different attributes for the data streams; providing to the local computer the applicable temporal rules and applicable relative rules thereby enabling temporal abstraction of the multi-dimensional data so as to generate temporally abstracted multi-dimensional data, and relatively alignment of the temporally abstracted multi-dimensional data based on an at least one time point of interest in a way that addresses the different attributes; and collecting the temporally abstracted and relatively aligned data from the multiple sites by communicating with the local computers and initiating the retrieval and transfer of the temporally abstracted and relatively aligned data based on a data mining request.

In this respect, before explaining at least one embodiment of the invention in detail, it is to be understood that the invention is not limited in its application to the details of construction and to the arrangements of the components set forth in the following description or the examples provided therein, or illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF THE DRAWINGS

The invention will be better understood and objects of the invention will become apparent when consideration is given to the following detailed description thereof. Such description makes reference to the annexed drawings wherein:

FIG. 10 shows a summary of the functionalities of existing prior art distributed temporal abstraction systems.

Figure 1:
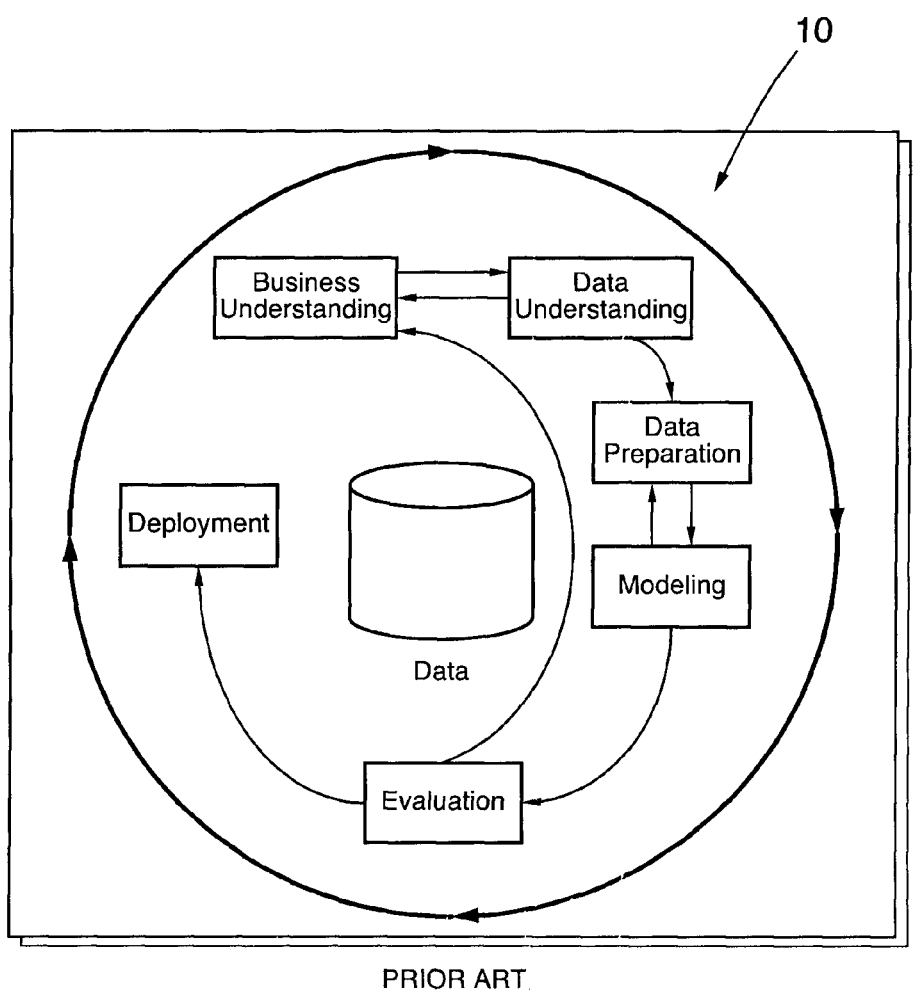
FIG. 1 illustrates a CRISP-DM model of the prior art.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

The present invention relates to a system, method and computer program product that provides a multi-dimensional distributed data mining environment that applies a series of temporal and relative rules (i.e., STDM$''_0$) includes one or more of the following features: (A) incorporates a framework to support temporal abstractions and relative alignments to data (i.e., SDTDM$''_0$); and (B) derives characteristics within the data and utilizes these characteristics to produce patient characteristic rules (STDM$''^{+p}_0$). The present invention may incorporate data from multiple sources, and potentially multiple centres. The analysis and alignment of the data may involve both temporal dimensions and other dimensions (or relative aspects) of the data. Another contribution of the present invention is a computer system, method, and computer program that is configured to manage distribution of distribute temporal and relative rules to multiple entities (such as different sites participating in the collection of data) in a way that permits data mining across multiple entities.

The present invention refers to a "data environment", "data mining environment" or a "framework" that enables the data mining operations described. The data environment, data milling environment or framework may be implemented by one or more computers linked to a computer program that when executed implements the processes described herein. A skilled reader will understand that the various references to the data environment, data mining environment, or framework also refer to computer system implementations of the present invention. In addition, a skilled reader will understand that the present invention contemplates various computer system implementations or computer network architectures for implementing the technology of the present invention are possible including but not limited to client/server architectures and cloud networking implementations; various existing networks or systems that collect data from different devices (such as monitoring devices), process data, aggregate data and report on data for a variety of purposes. In particular, the present invention may be implemented so as to interface with or be part of a health information system that may be connected with a plurality of devices (such as medical devices) that collect information in connection with which the present invention enables data mining on a managed distribution basis.

The present invention may be a data mining environment or computer system that enables data analysis (including for data mining purposes) of time dependent data across for example multiple streams, multiple entities, multiple possible attributes of the entities, multiple possible behaviours of the data stream over time and multiple events reflected in the data stream, resulting in a multi-dimensional environment. For example, the multi-dimensional environment may incorporate one or more of the following: multi-dimensional entities; multi-dimensional streams; multi-dimensional entity attributes; multi-dimensional stream behaviours; and multi-dimensional stream events. The present invention may further be a data mining environment that is flexible enough to permit relatively open ended queries, thereby enabling, for example, the detection of trends, including trends with new dimensions or trends based on relatively small data sets.

The discussion and description of the present invention in this document may utilize health care environment applications, and Neonatal Intensive Care Unit (NICU) uses in particular, of the present invention as examples of the present invention as a system, method and computer program product. This discussion and description of the present invention is provided merely as an example of one type of possible uses and applications of the present invention. The discussions and descriptions of the present invention are intended to clarify the operability and potential scope of the present invention. A skilled reader will recognize that many other uses and applications of the present invention in many other environments and industries may also be possible.

The present invention may incorporate a Service based Multi-Dimensional Temporal Data Mining framework operable to support a distributed multi-dimensional environment. This aspect of the present invention may be referenced herein as a $STDM''_0$ framework, element or computer system. The $STDM''_0$ aspect of the invention may further incorporate a framework designed to: enable the distribution of Temporal Rules in a multi-dimensional environment; support the multi-dimensional distribution of Relative Rules; and support distribution of Rule Base data which can be deployed for real time analysis.

However, the $STDM''_0$ framework may have certain limitations. For example, it may not address the area of data distribution and it may lack a structure that can support multi-center studies. The main limitations of the $STDM''_0$ framework may include that: it anticipates the use of a single Temporal Rule table and is therefore not well suited for a multi-centre approach; it anticipates the use of a single Relative Rule table and is therefore not well suited for a multi-centre approach; it lacks of a structure that is operable to accommodate multi-center studies in that its structure may not allow for the possibility of cross comparison of results between similar studies taking place at the same time; and it lacks clarity regarding how the Temporal Abstractions may be kept consistent in different locations/sites. Additionally, the $STDM''_0$ framework does not include a means of handling static and stream data in a distributed environment. This is an important limitation to consider as some data sets to be utilized by embodiments of the present invention may contains patient identifying information which may not be easy to distribute due to privacy policies. The present invention may overcome the limitations of the $STDM''_0$ framework and create an output that is operable to analyze and process multiple sources of data, including data from multi-center environments and multi-center studies.

One insight of the present invention is providing a computer system and computer system implemented method wherein there are two or more sites, each site having a $SDTDM''_0$, and a central computer system if provided (which may also be implemented on a distributed basis) that provides management and coordination between temporal and relative rules for the two or more sites.

The present invention may further incorporate a framework that supports analysis and trend detection in a multi-dimensional and distributed environment. This aspect of the present invention may be referenced herein as an $SDTDM''_0$ design framework. This framework may support a multi-dimensional distributed data mining environment. This environment may allow for the management of Temporal and Relative Rule tables in a distributed environment to support multi-center studies. The environment may further allow for the distribution of Rule Base data which may be applied to achieve real-time, or virtually real-time, monitoring across multiple sites. The $SDTDM''_0$ framework, a multi-dimensional distributed data mining framework, may be suitable for use in clinical research.

The present invention may address a problem in data analysis that is recognized by persons skilled in the art. Some types of monitoring may produce significant amounts of data, and it may be impossible to manually analyze the volume of data that is produced. Medical monitoring equipment is an example of monitoring that frequently produces large amounts of data that are impossible to analyze manually. Besides the volume of data sets that are produced, the complexity dealing with large datasets is increased further by the nature of the physiological monitoring data. Such data can multi-dimensional. This means that the data may reflect not only significant changes in a discrete, individual dimension, but may also reflect simultaneous changes in several dimensions that are significant.

Data produced by medical monitoring systems is often time-series produced. For this reason prior art analysis of such data has often focused on analyzing the temporal dimension of the data. However, there is a need for clinical research frameworks that enable both temporal behaviour and other dimensionality of the data to be preserved during data mining. Incorporating analysis of other dimensionality beyond merely temporal aspects of the data may have the result that information regarding time and context collected during the data mining process is not lost. Prior art systems routinely lose data that reflects aspects other than temporal behaviour. Consequently such systems lose important information regarding time and context of the data collected. This information can provide depth to the analysis and understanding of the data. Therefore the loss of dimensions of data occurring through the use of prior art systems is significant, and causes data gaps to exist.

The present invention can offer a framework whereby the dimensional, relational and contextual aspects of data is not lost, but can be captured. The present invention therefore may provide a means of analyzing multiple data streams to recognize not only temporal aspects of the data, but other aspects that represent non-temporal dimensions of the data streams. The present invention therefore may produce a robust analysis and understanding of the data that is collected, beyond that which is possible through application of known prior art systems.

Notably, in the field of clinical research critical advances can occur upon the discovery of new trends and patterns within collected data. In particular, such trends and patterns may be indicative of the onset of a condition in intensive care patients wherein the timing of certain events in a patient's condition and treatment can be of high importance. The present invention is operable to facilitate and otherwise enable discovery of trends and patterns in collected data. The present invention may achieve the discovery of trends and patterns by offering an integrated temporal abstraction data mining system that includes methods that enable realignment of historical data in relation to the onset of the condition being investigated. A skilled reader will recognize that the present invention may incorporate other methods as well to identify trends and patterns in collected data through the analysis of temporal behaviours and other dimensions of data.

In an embodiment of the present invention, a multi-dimensional distributed data mining framework may be defined that is operable to process time series research data and discover trends and patterns that may indicate a clinical event, prior to the occurrence of such a given clinical event. The framework of this embodiment of the present invention may utilize elements of data fusion and agent-based analysis so that it may be operable, either with or incorporating, relational databases and large scale data mining applications. In such a framework a set of data mining tools may be applied to undertake temporal abstraction, relative alignment and cluster analysis in a distributed manner that may support multiple research studies. As an example, the framework may be applied in a broad neonatal context addressing issues of data privacy and confidentiality and being deployable as part of one or more multi-center studies, while maintaining data integrity at each participating site.

One of the contributions of the present invention is that medical devices may collect physiological data with different frequency (which may be based on rules established for example by different sites regarding data capture and data transmission). For example, site A may collect data at a sampling rate of one data capture per minute, and at site B the sampling rate may one data capture per 30 seconds. In one aspect of the invention, the computer system of the present invention adapts the temporal and relative rules so as to address the difference in frequencies while enabling data mining relative to data sets collected from both site A and site B.

This embodiment of the present invention may analyze data in a context that incorporates all of the data available, which is data that is: collected from multiple sources (for example, such as multiple medical devices, or other sources); collected from multiple centres (for example, multiple hospitals, clinics, or other centres); and collected for multiple research studies (for example, centre-specific studies, and multi-centre studies). In the course of the analysis and other processing of the data, the present invention may recognize the data as a whole, and may further recognize the sub-sets of data, namely, the source, centre, and research study to which the data is related. Therefore, as the data is analyzed it may not only produce output that represents results, for example, such as trends and patterns, that relate to the data as a whole, the data may be analyzed in a manner that recognizes the other contexts of the data, such as the source, centre and research study relationships of the data. This means that the present invention may be operable to recognize results, for example, such as trends and patterns, for sub-sets of the data, namely relating to the source, centre or research studies to which the data is related. Therefore, the original integrity of the data may be preserved even after processing or analysis of the data is performed by the present invention. This offers the benefit that the data may be utilized from its original format for later purposes.

An advantage of this embodiment of the present invention may be that contextual relationships existing within the original collected data may be preserved, and utilized. Such contextual relationships represent dimensions of the data beyond merely the temporal dimension of the data and relating to other relevant context to the data that may be specific to a type of device, a manufacturer/model of a device, or even parameters specific to a particular device. For example these contextual relationships or data attributes other than temporal dimension may include the time/date when the data is collected, the approach of a particular device to data frequency, the approach of a particular device to correction of data collected, the approach of a particular device to identifying artefacts in the signals), but also represent other dimensions of the data, which may even include context provided by aspects of the data, such as the source, centre or research studies to which the data is related, or other dimensional aspects of the data. Moreover, both the temporal dimension and other dimensions of the data may be addressed and considered in the analysis of the present invention. This combination of dimensions of the data being involved in the analysis and processing of the data may further provide results which other prior art systems are unable to provide. Such data analysis results may lead to the identification of trends and patterns that may point to elements that may lead to the contraction of certain conditions, such as patient illness, or else early detection of an already contracted illness, that may not otherwise be identified when the prior art systems are utilized. A skilled reader will recognize the potential benefits that the present invention may offer in the health environment, and that the present invention may also offer other benefits in other sectors and environments.

One example of the present invention may be an embodiment that is utilized in the NICU environment. The NICU environment can often prove to be data rich yet information poor. The data intensive nature of this environment can create situations that cause physicians to be faced with an overwhelming number of variables when caring for an infant. Data collected from the necessary monitoring systems can be of a significant volume, for example it may include millions of entries in a database. Thus, the data being collected may not be usable in a manual manner due to the sheer volume of information. Data may be required to be extracted and organized to become useful information, and a domain expert may then be required to interpret the information before it can be rendered into a form that represents applicable knowledge.

There may be two forms of critical data that can be defined in the NICU environment. First, the physiological data which is collected from sensory and monitoring devices which may include as an example monitoring devices collecting and displaying data like heart rate, transcutaneous oxygen saturation (SpO2), electrocardiogram (ECG), blood pressure, and respiration rate. The physiological data may be comprised of data streams, often acquired at varying frequencies. For example, the Phillips Component Management System (CMS) outputs the following types of data streams: numeric—a reading generated every 1024 milliseconds; wave—every 32 milliseconds four data values arrive via the wave data stream (126 values every 1024 milliseconds); and fast wave—16 values arrive every 32 milliseconds (512 values every 1024 milliseconds). Second, the clinical data may include information pertaining to aspects of the patient, such as patient age and weight, and such data may be comprised of paper notes or periodic readings undertaken by nurses.

There may be several conditions of interest affecting patients in the NICU. Infection is a common cause of morbidity and an important cause of mortality for newborn infants. Although many infants may acquire an infection around the time of delivery, others may acquire an infection while receiving intensive care in the NICU. These are referred to as hospital-acquired or nosocomial infections. The early diagnosis of a nosocomial infection may be difficult, because the clinical signs of infection can be subtle and nonspecific until the infection is well established. These infections can occur 48 hours or more after birth and data indicates that almost 30% of infants born at 25-28 weeks gestation and more than 45% of infants born prior to 25 weeks gestation may experience a serious nosocomial infection while in the NICU. Intraventricular Hemorrhage (IVH) is another common cause of morbidity and mortality for the newborn infant, Approximately 20% of preterm infants may develop an IVH. The haemorrhages may occur during the first few days of life and more than 90% of the IVHs have occurred by the third day of life. A skilled reader will recognize that other conditions of interest exist for both NICU patients and for other patients, as well as for other data sets, streams and sources, therefore the NICU example and related details is merely presented as one example of an embodiment and application of the present invention.

Patterns may be detected in the physiological data if the data from the monitoring devices is captured and stored in data warehouses and is available for date mining. The main reason for storing and mining this data would be to discover previously unknown trends and patterns across various parameters and the establishment of indicators of the onset of conditions that may have an adverse effect on outcomes. Additional information, for example, such as clinical data, may be combined with the physiological data as part of the overall data provided to the present invention.

The data provided to the present invention may be a distributed data environment that involves multiple hospitals across the globe, and both the type of data generated and frequency at which data is being output may differ from one site to another. The differences may also occur due to the physiological monitoring devices being different at each facility. As an example, The Hospital for Sick Children makes use of the Philips IntelliVue MP70 series of patient monitoring devices in their NICU. The Shenzhen Maternity and Children's Hospital, Shenzhen makes use of the Dräger Infinity Delta XL series of monitors and the Women & Infants Hospital in Providence, R.I. makes use of the Spacelabs Ultraview SL series patient monitors, Not only can the format and frequency of data output differ between these devices, the frequency at which this data may be streamed to the data warehouse or other data receivers can also vary for each site. In addition, the levels of NICU care can add another level of complexity and distribution as a patient graduates or is moved from one NICU to another. Thus the need for a distributed data mining framework is quite evident when dealing with multicenter studies.

The present invention applied in the NICU environment can process and analyze the data from multiple sources, multiple centres and multiple research studies. The present invention may address the temporal dimension of the data, as well as other dimensions of the data. Through this analysis and processing patterns and trends in the data can be discovered, which may lead to the identification of factors leading to, or related to, the onset of particular conditions. This information may be used to set-up new policies, for example, such as policies to improve NICU care, or may be used to determine how to avert the onset of particular conditions in future.

Another embodiment of the present invention may be a multi-dimensional patient oriented data mining framework used to support critical care research. The framework may be operable to discover physiological stream behaviours.

Due to the multi-source, multi-stream, and/or multi-research studies data that may be utilized by the present invention to be analyzed or otherwise processed, the behaviours discoverable through the utilization of the present invention may be earlier condition onset behaviours than those currently used in evidence based practices. The behaviours currently used in evidence based practices may be those behaviours that are discoverable by prior art systems or other known methods. The present invention may be operable to provide outputs that are based on the analysis of large volumes of data, from multiple sources/centres, that involve the analysis of dimensions of the data beyond merely temporal dimensions. For these reasons the present invention may provide important support to critical care research that prior art systems cannot provide. The physiological stream behaviours identifiable by the present invention may provide crucial identifiers of condition onset, and such identification may occur at an early stage before the condition progresses significantly.

One embodiment of the present invention, which incorporates a $STDM^{n+p}{}_0$ framework or element, may incorporate one or more individual attributes included in the data, for example, such as patient specific attributes, into the analysis and processing of data, and such attributes may further be part of the results of the present invention. The attributes, such as patient specific attributes, may be utilized as measures, such as patient specific measures. The incorporation of attributes, such as patient specific attributes, may cause the present invention to be operable to tailor and cluster physiological stream behaviours based on these patient specific measures. In another important insight of the present invention, the computer system of the present invention permits data driven data mining that permits the clustering of streams of physiological data in order to support analysis of data sets for specific attributes.

The framework of the $STDM^{n+p}{}_0$ element of the present invention may include methods for applying temporal abstractions (TAs) representing physiological stream behaviours across multiple patient attribute parameters for multiple patients. This may cause the present invention to be operable to undertake mining of multi-dimensional temporal data. One embodiment of the present invention may utilize the $STDM^{n+p}{}_0$ framework as an element in a multi-dimensional approach that may: support temporal abstractions of time series data; and deploy clinical algorithms and other calculations.

Certain data may be captured and utilized by the present invention in a manner that allows for the extraction of patterns of predictive temperament. As an example, the exponential activity of a growing neonate in its early stages of life may be required to be captured and embedded into algorithms designed to extract patterns of predictive temperament within the NICU (neonatal intensive care unit) domain. Embodiments of the present invention that incorporate a $STDM^{n+p}{}_0$ framework may undertake an extended multi-dimensional approach to data, and may further create, or lead to the creation of, patient characteristic clinical rules.

In this manner the present invention may offer a benefit over the prior art. The present invention may be operable to further define algorithms or other calculations, for example, such as NICU algorithms or other calculations, through the use of attributes, for example, such as attributes that include gender and gestational age (GA). The present invention may further use the algorithms and other calculations in clinical decision support systems to increase the accuracy of such systems. Increasing the accuracy of clinical decision support systems may minimize the risk of adverse events in comparison to the risk of adverse events presently experienced in the course of the application of known prior art systems.

In this document the terms "attributes" and "characteristics" may be understood to have the same meaning and may be utilized interchangeably.

Looking to the NICU context as an example of one possible application of the present invention, in the NICU context individual patients may undergo rapid growth and development leading to changes in individual patient characteristics. For example, patient characteristics such as weight, heart rate (HR), blood pressure, and postnatal age may change. There is a growing body of research showing examples of the use of data mining and temporal abstractions to demonstrate that a given condition exhibits certain physiological stream behaviours. However sensitivity and specificity are not yet near 100%, and this lack of specificity in the healthcare environment can have devastating impact on an individual patient.

The present invention offers the potential to use patient characteristics to gain better understanding of individual patients in retrospective data and to improve sensitivity and specificity by creating subgroups of characteristics. For example, subgroups may include individuals having similar physiological behaviours and temporal behaviours. The present invention may provide frameworks that can support exploration and clustering based on patient characteristics. The present invention may be operable to identify trends and patterns while it explores patient specific physiological data streams. The result may be that the present invention aids in the improvement of real-time clinical management and clinical decision support by providing data analysis and data processing results in real-time or virtually real-time to a clinical professional, such as a nurse, doctor, or therapist for a particular patient. The data results of the present invention may support a patient oriented approach to patient care, and this may assist in minimizing adverse events that occur in the NICU and other health departments and environments. A skilled reader will recognize that the present invention may also be applied to other environments as well as health care environments.

The present invention may be operable to perform multi-dimensional data mining based on patient characteristics that ultimately can assist in providing clinical support to caregivers. For example, clinical support may be provided by the present invention to a caregiver as the data analysis or data processing functions of the present invention recognize that physiological thresholds are being breached. In this manner the $STDM^{n+p}_0$ framework may support clinicians as they perform patient oriented clinical research to improve patient outcomes and morbidity via real-time, or virtually real-time, anomaly detection in multi-dimensional physiological data streams.

Embodiments of the $STDM^{n+p}_0$ framework may involve one or more of the following: (i) that a patient characteristic multi-dimensional data mining framework can be defined for clinical research to enable use of patient attributes when data mining patient physiological data streams; (ii) that the patient characteristic framework will include methods for applying temporal abstraction (TA) across multiple parameters for multiple patients to enable mining of patient characteristic multi-dimensional temporal data; (iii) that the multi-dimensional algorithm (or other calculation) framework can be applied in a neonatal context clustering patient characteristics by gender and gestational age; and (iv) that the hypotheses generated by the patient characteristic framework can be used by a real-time, or virtually real-time, event stream processor that analyzes the current condition of babies in a NICU.

One embodiment of the present invention that incorporates a $STDM^{n+p}_0$ framework may represent extensions to the $STDM^n_0$ multi-agent framework for analysing time series data. Such extensions may include operability to use attributes, for example, such as gender and gestational age, into a multi-dimensional approach capturing patient characteristic-based temporal abstractions, complex abstractions, and relative alignment of these abstractions. The design of the $STDM^{n+p}_0$ framework of the present invention may be operable to incorporate patient characteristic multi-dimensionality with temporally abstractive data mining. Thus, the present invention may demonstrate the potential benefit and use of data mining from electronically stored physiological data for improved real-time clinical management and patient centric clinical decision support. The present invention may further demonstrate the potential for clinical research on stored physiological data streams to deduce new findings for condition onset prediction indicators in support of a current ethics approved clinical research study. A skilled reader will recognize the wide scope of uses and applications of the present invention in a variety of environments.

The present invention may provide several benefits and advantages over the known prior art. There are several challenges in developing a distributed data mining framework able to work in a multi-dimensional environment. Ability to handle varied data frequencies, considerations on data privacy and the location of where patient data exists, ability to handle real time stream data and the synchronous deployment of abstractions for data consistency are key considerations towards designing a functional framework. In order to enable the discovery of new trends and patterns that may be indicative of the onset of a condition in patients, there is a need for an integrated multi-dimensional distributed data mining framework. FIG. 10 provides a list 100 of several prior art distributed temporal abstraction systems and provides comments outlining the shortcomings of each of these. The present invention overcomes the shortcomings of the prior art systems, as noted in the table of FIG. 10, and thereby provides several benefits over the known prior art.

As another example, a particular advantage provided by the invention is that the temporal rules of the present invention are operable to create a multi-dimensional environment that by means of a data preparation stage, enables data streams to be encoded with time stamps relative to specific points of interest. Prior art systems are generally only able to process data in a temporal dimension. The present invention may include temporal data analysis, but can also process and analyze data in other dimensions, as described herein. The present invention may provide an environment that is operable as a holistic framework that can utilized data from, as well as provide relevant results to, multiple studies across multiple parameters for multiple patients.

As yet another example of a benefit offered by the present invention over the prior art, the present invention may provide a flexible and distributed multi-dimensional approach to data mining. Known prior art generally lacks flexible and distributed multi-dimensional approaches to data mining of time series data. The recent momentum in research has prompted hospitals across the globe to partake in multi-center studies that involve the cross site analysis of the same physiological data streams to review the data for indications of the same events at different hospitals. This activity brings the element of data distribution into context, as physiological data being collected from monitoring devices may differ in format and frequency for each facility, as discussed herein. The differences may also occur due to the physiological monitoring devices being different at each facility, as discussed herein. Known prior art systems are generally unable to cope with the varying data, and cannot treat the analysis of such data in a common manner. The present invention may be operable to process and/or analyze data from multiple sites in a common manner, even if the data is collected from different physiological monitoring devices and/or from different sites. Thus, the present invention may incorporate levels of flexibility that the prior art lacks. The present invention may further apply distributed multi-dimensional approaches to the data mining of time series data which the prior art is unable to undertake.

Possible Implementation of Invention with Temporal and Relative Rules for Multi-Dimensional Data Mining ($STDM^n{}_0$)

Figure 2:
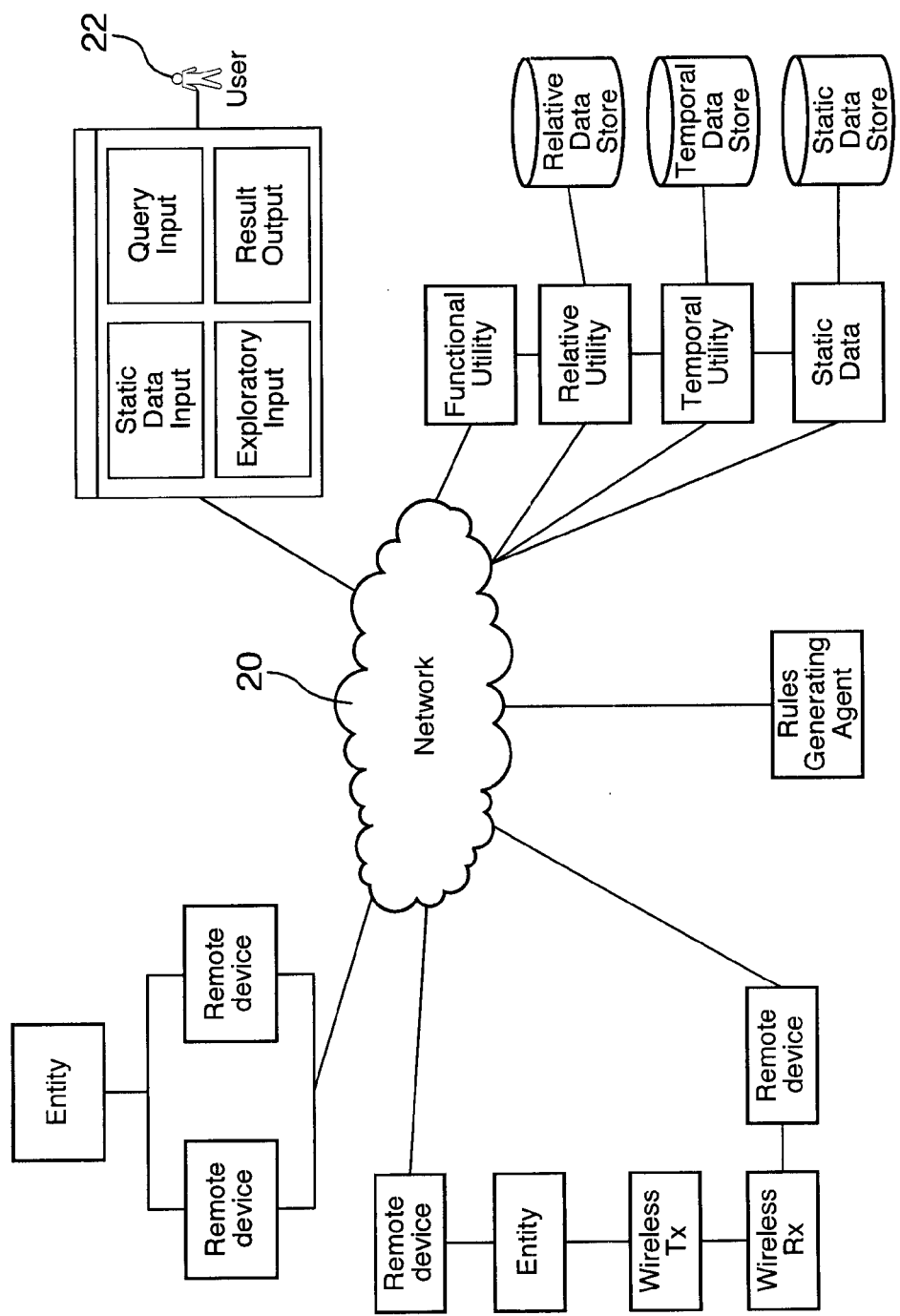
FIG. 2 illustrates a system that is one possible embodiment for implementing the present invention.

A $STDM^n{}_0$ framework may represent aspects of the present invention. This framework, as shown in FIG. 2, may generally include several elements that may be connected via a network 20, be operable to receive and store data, and be operable to correspond with a user 22.

The method of the present invention may include a number and variety of steps. As a general initial step, the multi-dimensional data may be collected and the present invention may optionally clean-up this data. The activity of cleaning-up the data may involve any of the following: removing superfluous data; establishing a means of commonly processing variant forms of data; and organizing the data info a form for processing and analyzing. As a general next step the present invention may temporally abstract the multi-dimensional data to create a dynamic data mining environment in multiple dimensions, as is described in more detail herein. As a genera subsequent step, the temporally abstracted data may be relatively aligned.

The process of temporal abstraction may involve either raw device or pre-processed stream data as input and may utilize domain knowledge (context) to translate the raw data into behaviour or event information that is at a slower frequency of lime than the inputted stream(s) for the inputted data thereby producing higher level, context-sensitive, qualitative, interval-based representations. Complex temporal abstractions can be created by assessing behaviours across multiple streams.

Optionally, as a general fourth step, the present invention may engage in exploratory and/or explanatory data mining in the created multi-dimensional data mining environment. Exploratory data mining refers to data mining by supporting queries to the data mining environment without imposing rules or functions. Explanatory data mining attempts to further validate rules by performing further data mining on more datasets.

An alternative fourth step, or a fifth step in addition to the fourth step described above, is linking to one or more remote devices to enable the one or more remote devices to use the resulting temporally abstracted and relatively aligned data. The remote devices could be any device linked to or associated with the invention that provides the data streams described. The remote devices may be located in close physical proximity of each other, the system and the entity. The remote devices may alternatively be located outside of close proximity to the system, each other, or the entity for example at remote regions of a country or the world, connected to the system over the Internet or another network. The remote devices could be linked to the system or to entities wirelessly.

The devices could all be connected to one entity, or a series of subsets of devices could be connected to a series of entities existing within an overall population of sample set. Devices could be for example medical physiological monitoring devices, smart meters, car telemetry monitoring devices, weather sensors, network traffic monitors, share price data streams or power plant monitoring systems. Matching entities within a population could be patients within a healthcare population, homes within an electricity grid, motor vehicles, or weather stations respectively.

The computer program of the present invention is best understood as including (1) a temporal utility or agent, and (2) a relative utility or agent, both corresponding to the method steps above. The temporal utility and the relative utility are linked. The computer program of the present invention enables at the very least queries to the resulting temporally abstracted and relatively aligned data. Optionally, the computer program enables exploratory and/or explanatory data mining, which in one implementation takes the form of the functional agent that has been described.

Optionally, a rules generating agent is provided. The rules generating agent provides a mechanism for a user to either generate rules by proposing rules and storing them in a data table or to store rules proposed by the system during the exploratory data mining stage. Alarms, alerts or messages can be initiated in response to the temporally abstracted and relatively aligned data with respect to the rules.

The process may be user driven. Typically, the user will know what they are studying and the rules that are desired. Queries may be user driven in that a user may manipulate, analyze or monitor data as desired. The queries may be provided by the user using a user interface.

The user interface may provide means for inputting study selection criteria. This part of the user interface is data driven and enables the user to select criteria to define the relative time point of interest together with other selection criteria for the entities that will qualify for the study.

The user interface may also provide means for inputting relative time points of interest, which enables the user to select points of interest based on either; an event; an entity attribute; a stream behaviour; or a stream event (with the latter two being represented by their own stream temporal abstractions). A user may first determine whether the time point of interest is from an event, entity attribute or a temporal abstraction. The time point of interest may be defined as a date/time, which is a time point operable to be used as the reference point to relatively align the data streams of interest. Based on the user's selection, the user is then provided with a list populated directly from the database that is either: a list of possible events; a list of entity attributes that have date/times; or a list of temporal abstractions. In the case of temporal abstractions the user can choose whether the first or most recent occurrence of the temporal abstraction is of interest and may also determine whether the start or end time is of interest.

If an event is chosen as the relative point of interest then the date/time that the event occurred for a selected entity is the relative time point.

If an entity attribute that is a date/time is chosen as the relative point of interest (for example, what common behaviours exist after a certain time relative to the entity), then that date/time is the relative time point for the selected entity such as the date of completion of manufacture or the date of birth.

If a temporal abstraction is chosen, then the date/time associated with the selection criteria for the temporal abstraction for the given entity is chosen.

The result is a list of entities that satisfy the selection criteria and for each entity the date/time point representing $t_0$ for the relative alignment process is also listed. This resultant list may be persistently stored within the database, but this is not compulsory as it can be regenerated via the information contained within the other tables based on the contents of the study table for that particular study.

In addition to defining the relative time point of interest, the user is able to provide other selection and/or exclusion criteria through similar database populated data driven lists to determine what entities should be part of the study. These criteria can be from any or all of the entity attributes, event attributes, temporal abstractions or relative temporal abstractions.

Queries can be made on the static and/or raw data stream together with the temporal and relative data streams in any desired combination. The temporally abstracted and relatively aligned data can also be dynamically analyzed to determine specific information. For example, one could easily determine average performance at a specific point of time, which is very difficult to do manually, particularly where concurrent stream assessment is required.

The system of the present invention can be implemented to a known database engine or similar technology. The invention may comprise a computer system that includes one or more computers including at least the temporal utility and the relative utility, the computer system being linked to one or more database engines or similar technologies, the database engine(s) either including static data, data from one or more remote devices or sensors, or the computer system being linked to one or more remote devices or sensors, directly or indirectly, so as to populate the one or more databases provided by the database engine(s) with sensor data.

Figure 3:
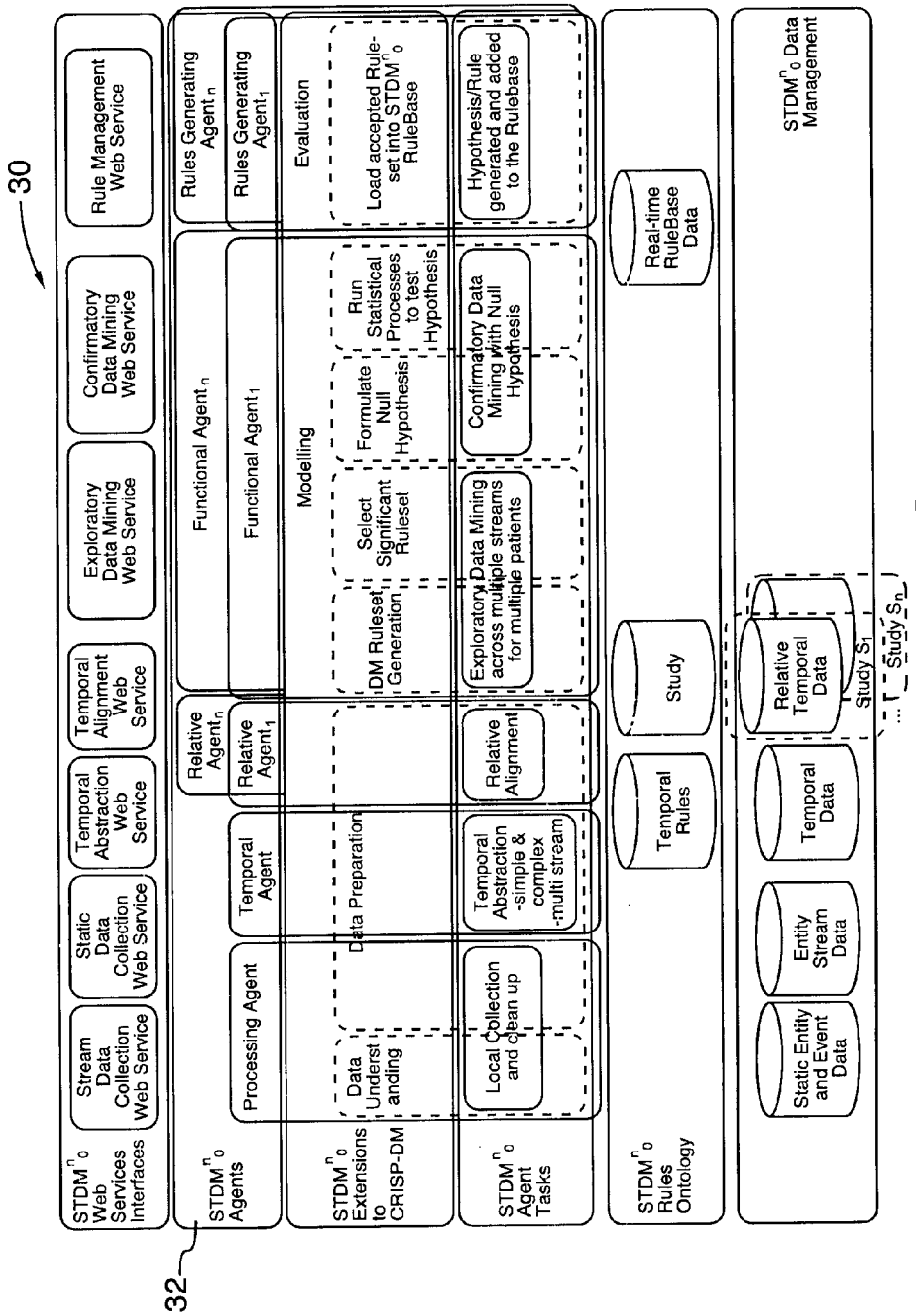
FIG. 3 illustrates an embodiment of the present invention that is accessible through a cloud computing architecture.

Optionally, the system can be implemented as a cloud computing implementation where the use of this environment is provided as an external service through a series of web services. FIG. 3 illustrates the present invention accessible through a cloud computing architecture. The system could also be implemented as a proprietary solution still accessible via the set of web services where data from one source (and possibly multiple sensors, etc. from each source) is provided to a web server connected to the Internet and linked to at least the temporal utility and the relative utility where the web server delivers the temporally abstracted and relatively aligned data, or output of the exploratory and/or explanatory data mining discussed above. Rules as provided by the present invention could also be added, changed or deleted from using a web service. It should be noted that one of the benefits of the web service model is that multiple organizations linked to the web server can provide a larger number of data sets that improves the data accessible by each of the participating organizations.

The invention is particularly applicable to a variety of areas, specifically wherever there are multiple sensors or otherwise multiple streams of data relating to events or behaviours occurring and different times that relate to a specific "end state" or "end condition" of an "entity" that is of interest. An "entity" could be a patient or an apparatus being monitored, for example. The events or behaviours may cause or contribute to the end state or end condition, for example, a series of successive events may define a timeline leading to a particular state or condition.

Figure 5:
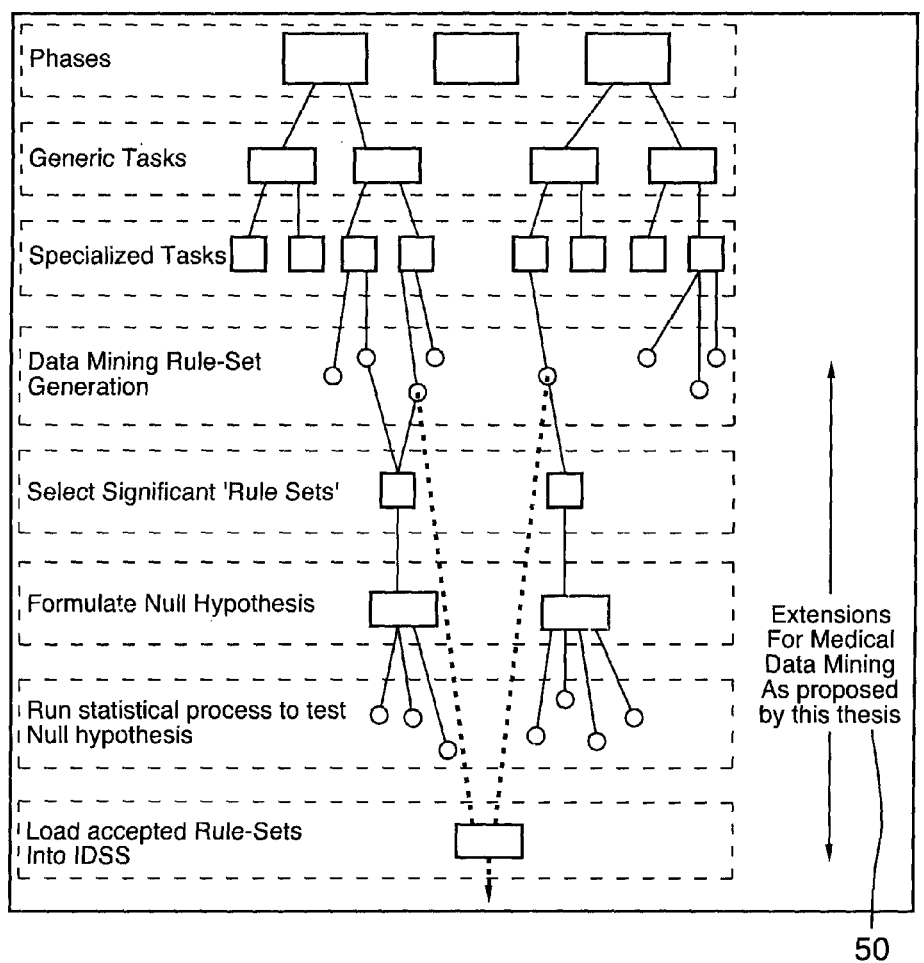
FIG. 5 illustrates an extended CRISP-DM model satisfying the need for null hypothesis testing that is an embodiment of the present invention.

This environment, an example of which is shown in FIG. 5, may include an approach to data mining that supports null hypothesis testing through the provision of exploratory and confirmatory data mining functions 50. The invention also includes an ontology design to support the temporal, relative rules together with a multi-dimensional rule base. The environment supports static data (for example, clinical data) together with sensor data that can be numeric data (for example, temperature or blood pressure) streams or waveform data (for example, ECG and EEG) streams and supports data mining that cross correlates between data streams together with the static data. The storage of temporal and relative temporal data is also supported for secondary analysis of the data for other related clinical research.

In terms of the area of application, it is important to understand that the invention can be applied to any domain where there may be multiple sensors used to monitor events or parameters that relate to similar or the same behaviour. The technology is relevant at least to patient care, monitoring structural failure, weather events, smart meters, etc. Wherever it is a challenge to extrapolate from multiple sources of information, over multiple events that occur at different times, the invention is advantageous.

Also advantageously, the multi-dimensional data mining environment of the present invention supports multiple studies. These can be entity centric, entity attribute centric, stream centric, or event centric, or can also draw from any other fields in the ontology. For example, in the field of patient care, three babies may all develop an infection and, for example, the technique enables the investigation of common factors between these three cases, for example as to heart rate, respiratory rate, etc. Additionally, as there are actual times associated with these incidents, the invention enables tracking of multiple behaviours on multiple streams generated by the various sensors, and building a data structure that enables realignment relative to a diagnosis event in order to engage in better analysis within the environment, for example to better track progress of each baby in real time based on average factors at a particular point in time during the progression of the infection, etc.

The present invention enables a user to have advanced knowledge of when to intervene to prevent or mitigate a condition. There is an event state of interest, for example an engine failure or diagnosis event. The present invention provides an environment where the user can see the previous events that move toward an event state, and to explore that trajectory path to determine where the entity is in terms of event state (i.e. is the entity heading for the event state or not, and when). The trajectory path may be defined based on averages that are historical, but enables a user or a system to react in real time.

Furthermore, the present invention enables the trajectory path to be created using relatively small data sets and to be refined based on additional data sets. The present invention also reacts to new conditions.

In a particular illustrative example, the data can be temporally abstracted relative to an event. For example, where a condition or event has occurred, there are multiple sensors providing a picture of a particular entity, for example a patient or a car. These multiple sensors may be on different organs or components for example, thereby providing a multi-dimensional data stream. Data can be collected over an extended period. Data from similar entities in which the condition or event occurred can also have been collected over time. The condition or event can be set as a point of interest, and the multi-dimensional data can be mined to determine trends leading to the condition or event.

The paper entitled *"Multi-Dimensional Temporal Abstraction and Data mining of Medical Time Series Data: Trends and Challenges"*, Catley, C, Stratti, H & McGregor, C, Aug. 2008, 30 International IEEE Engineering in Medicine and Biology Society Conference, 4322-5 illustrates some of the current research on time series data, temporal abstraction generally (as opposed to the particular temporal abstraction techniques and system described herein), as well as principles of null hypothesis testing.

One aspect of the invention is population of the data mining environment for health care applications with physiological data. This can be done for example using the physiological data models described in "A Web Service Based Framework for the Transmission of Physiological Data for Local and Remote Neonatal Intensive Care", McGregor, C., Heath, J., & Wei, M., 2005, *Proceedings of the IEEE International Conference on e-Technology, e-Commerce and e-Service*, Hong Kong, IEEE pp 496-501.

Data Mining Framework

The present invention provides a framework for multi-dimensional data mining of temporal data. The present invention can support both local use together with the use through a service based model. This framework is herein referred to as a service-based multi-dimensional temporal data mining ($STDM''_0$). The framework as applied to support analysis and trend detection in historical data from Neonatal Intensive Care Unit (NICU) patients is described in "A Multi-dimensional Temporal Abstractive Data Mining Framework", Bjering, H. & McGregor, C., 2010, *Proc. 4th Australasian Workshop on Health Informatics and Knowledge Management*, Brisbane, HIKM pp. 29-38, which is herein incorporated by reference. $STDM''_0$ is operable to discover trends and patterns indicative of the onset of a condition; includes methods for applying temporal abstraction across multiple parameters for multiple entities to enable miring of multi-dimensional temporal data; supports null hypothesis testing; can generate hypotheses that can be used by a real-time event stream processor analysing the current condition of entities; and generates hypotheses that can be translated into rules to be used by a real-time event stream processor used for monitoring and alerting.

Figure 7:
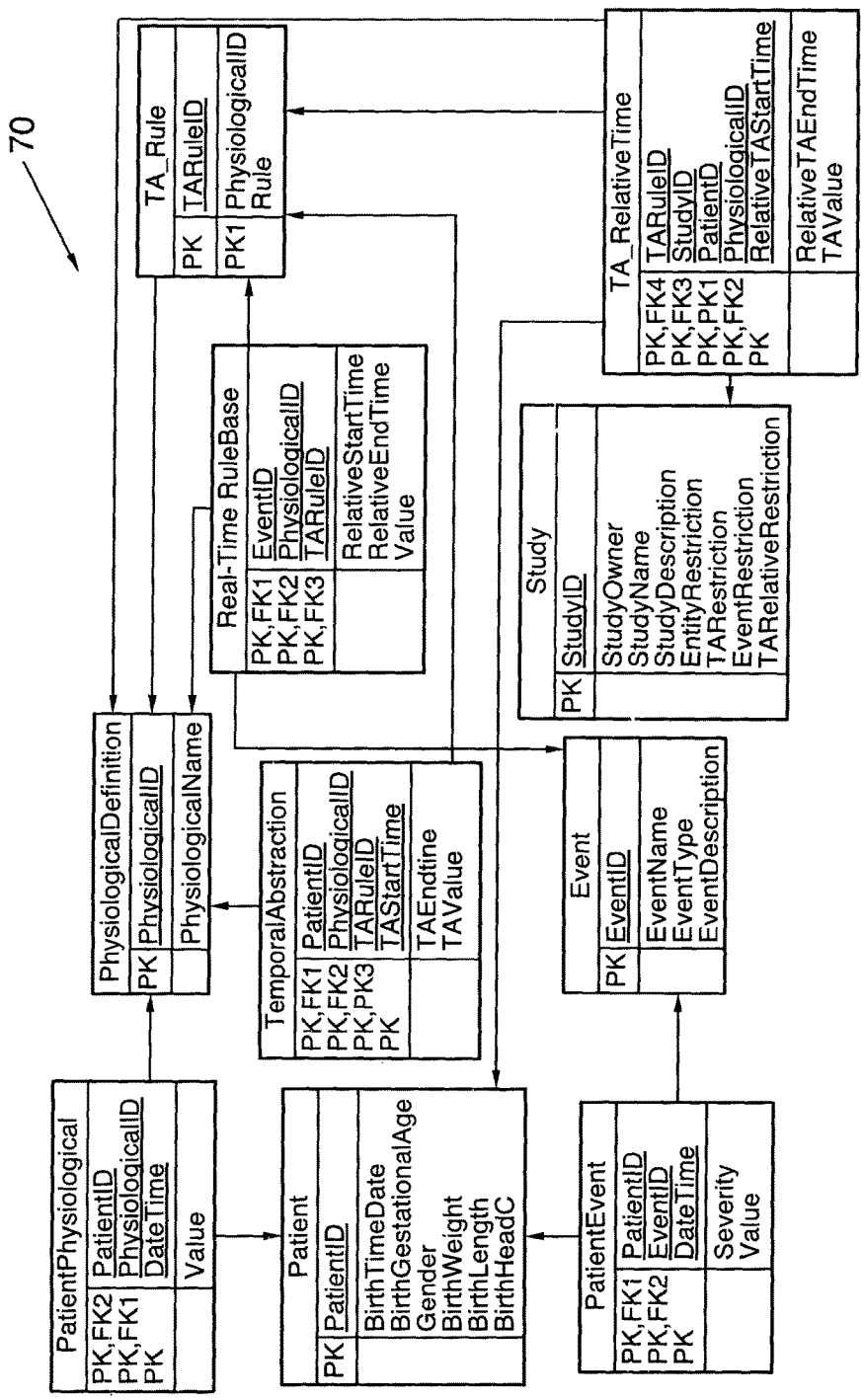
FIG. 7 illustrates the data storage schema of FIG. 6 particularly for implementing the $STDM''_0$ framework for clinical research that is an embodiment of the present invention.

$STDM''_0$ may provide a mechanism to support the functionality of an extended CRISP-DM data mining model to facilitate null hypothesis testing. CRISP-DM may be a 6 phase hierarchical process model 10, as shown in FIG. 1. At the highest level the six phases are: business understanding; data understanding; data preparatior; modeling; evaluation and deployment. In the present invention the phases may have associated with it a set of sub tasks 70 that are spread across the lower levels of the hierarchical model, as shown in FIG. 7. The approach to extend CRISP-DM to support the scientific method based null hypothesis testing may be incorporated in the overall present invention, as shown in FIG. 3. It may be possible to engage this aspect of the present invention in an embodiment that is a cloud computing model.

$STDM''_0$ comprises an architecture that bridges the gap between data management and data mining research, enabling the secondary use of some of the vast amount of data collected by monitoring equipment. New data collected is fed into the framework with the existing data to help further refine the hypotheses created in the $STDM''_0$ framework.

The $STDM''_0$ model is supported by multiple agents that facilitate interaction between the user and the data contained in the active rules ontology and the data management layers. The multiple agents are comprised of a processing agent, temporal agent, a relative agent, functional agent, and a rules generating agent, as hereinafter described and as shown in FIG. 3.

A plurality of data stores are also provided by the $STDM''_0$ framework including a temporal data store and a relative temporal data store.

The multi-agent data mining system of the $STDM''_0$ framework 30 is shown in FIG. 3. This framework diagram maps the agents used to the appropriate parts of the extended CRISP-DM model and sets out the individual $STDM''_0$ tasks.

Referring to the horizontal column in FIG. 3 labelled $STDM''_0$ Agents 32, the first agent in the $STDM''_0$ framework is the processing agent. The processing agent acts as a pre-processor for the functional agent, performing the tasks of getting and preparing the data and storing it within the data stores so as to be ready for further processing by the temporal agent. As illustrated under the $STDM''_0$ Extensions to CRISP-DM column, the processing agent is used to support and partially support the phases of data understanding and data preparation within the CRISP-DM model.

Under the $STDM''_0$ Data Management column, the processing agent would usually acquire data from external databases for the static data and via sensor devices for the stream data.

The processing agent uses the static and stream web services enabling data to be pushed or pulled directly to the processing agent. Data can also be sent directly to the processing agent via a direct connection.

Referring next to the $STDM''_0$ Agent Tasks column of FIG. 3, there is one primary task performed by the processing agent, namely, local collection and cleanup. This task involves collecting the static and stream data from the external databases or use within the $STDM''_0$ framework, as the data arrives and general data cleaning, such as, checking for erroneous values is performed. Those erroneous values are those, for example, caused by irrelevant factors related to the entity, employing strategies for dealing with missing values, etc.

The data is extracted from external databases by the processing agent, transformed to the required format and stored in the data stores within the $STDM''_0$ framework, as set out in the $STDM''_0$ Data Management column. Static data obtained from the entity or describing the entity is entered into a static data table and the sensor data is stored in the sensor data table. This task supports all of the data understanding and part of the data preparation components of the extended CRISP-DM model proposed within $STDM''_0$.

The local collection and clean up task is the task of the processing agent as one of the agents within $STDM''_0$. Referring next to the $STDM''_0$ Web Services Interlaces column shown in FIG. 3, the processing agent can either acquire the data directly from the source or be provided the data by the Stream Data Collection Web Service and the Static Data Collection Web Service.

In a traditional data warehouse setting, where raw data is copied into the data warehouse and aggregated via a periodic load followed by batch aggregations, the processing agent can, for example, be implemented as an agent in the database management system (DBMS) housing the data warehouse. A periodic extract could run from the operational data receiving the sensor data and that extract loaded into the $STDM''_0$ environment via a script enacting the processing agent.

Within the stream computing paradigm, where data is manipulated as a stream as the data arrives in real-time, the processing agent could be a stream competing program receiving the streams directly from the sensors as the data arrives in real-time and outputting the data through a database output operator to enable the row insertion.

In a services computing paradigm, both the database script and the stream computing program can be enacted via the enactment of the Stream Data Collection Web Service or the Static Data Collection Service.

Referring again to the STDM"$_0$ Agents column, the next agent in the framework is the temporal agent. The temporal agent generates temporal abstractions on the data prepared and stored by the processing agent. The temporal abstractions to be performed are defined by temporal rules of the STDM"$_0$ Rules Ontology. The temporal abstractions represent a pre-processing method before data mining which allows the temporal aspects and the context of the data to be preserved.

By way of example, in a clinical research setting, for a given patient set each of the relevant physiological streams may be temporally abstracted into appropriate abstractions such as trends (increasing, decreasing) and level shifts (high, low). Each raw piece of data may belong to several abstractions. For example, a particular measurement may be part of an 'increasing' abstraction, and at the same time be within 'normal' limits. Complex abstractions can also be done across multiple abstracted parameters.

While individual data values themselves may not provide valuable information, when considered over time and context the values can create meaning. The STDM"$_0$ framework will use temporal abstraction as pre-processing of the data prior to exploratory data mining. In accordance with the tasks listed under the STDM"$_0$ Agent Tasks column, for each entity, each sensor stream is temporally abstracted into appropriate abstractions such as trends and level shifts. Complex abstractions can also be done across multiple abstracted parameters. Each abstraction including actual start and end times for the particular abstraction instance may be stored as temporal data as part of the STDM"$_0$ Data Management component As depicted by its overlap in FIG. 3 with the data preparation step, the temporal agent is used to partially support the phase of data preparation within the CRISP-DM model.

Referring next to the STDM"$_0$ Web Services Interfaces column, it is observed that the temporal agent uses the temporal abstraction web service enabling data to be pushed or pulled directly to the temporal agent. Data can also be sent directly to the temporal agent via a direct connection.

The temporal agent has five main functions performed as the temporal abstraction task: (1) retrieve the relevant temporal rules from a temporal rules table; (2) apply the temporal rules to the data creating simple abstractions for individual data streams for individual entities; (3) store the created slow frequent temporal abstractions streams in the temporal data store; (4) create complex abstractions from the simple abstractions created in step 3, according to any of the relevant temporal rules; and (5) store any complex temporal abstractions streams created in the temporal data store.

Examples of temporal abstractions may include the following: (i) Neonatal Intensive Care: (a) the start and end times where mean arterial blood pressure falls below the neonatal patient's current gestational age; (b) the start and end times where the neonatal patient's blood oxygen level fails below 85%; (c) the start and end times where the neonatal patient's blood oxygen level is falling at a rate greater than the threshold specified; and (d) a complex abstraction of the start and end times where 1) and 2) occur concurrently for more than 20 seconds. (ii) Electricity Grids: (a) the start and end times when electricity goes above a certain threshold. (iii) Weather: (a) the start and end times when the temperature at that weather station goes above 35° C.

Referring again to FIG. 3, the relative agent represents the next phase of the framework. When a user wishes to investigate the possibility of certain patterns or other signs appearing in an entity's sensor data before or after some event, there will often be a need for aligning the data, including both static data and abstractions of sensor data, relative to for example the time of diagnosis. This will allow users to study particular outcomes and remedial methods on other entities. These relative alignment processes make up the STDM"$_0$ Agent Tasks of the relative agent.

The point of interest to which to relatively align the data could be a time of diagnosis in a clinical context but need not be. It could be based on any event or behaviour.

When researching a particular event, the abstractions are matched with the event table holding the entity's event time and date. This information is fed through a transform algorithm to enable a measurement in time for the abstractions relative to the point in time of the diagnosis. $T_0$ is the point of event, and $T_{-1}$, $T_{-2}$, $T_{-3}$ . . . $T_{-n}$ indicates the distance in time between an abstraction before the time of event, and the event. This step enables the 'lining up' of data relating to entities at the point of the event, to enable the detection of trends and patterns that may be common in entities at a particular point in time before or after the onset of some event. Significant changes it a particular parameter in the lead up time to the event can be isolated to enable the finding of any significant indicators for determining what time the change or behaviour of a particular parameter occurred in relation to the onset of the event.

The relative agent uses the abstractions created by the temporal agent and stored in the TemporalAbtraction table, together with static information of individual entities to create the data subset or data mart in support of a specific study. There can be any number of relative alignments performed on the temporal abstractions, as denoted by the Relative Agent$_1$ and Relative Agent$_n$ labels in FIG. 3. A particular alignment is determined by the type of study that is to be undertaken, which is specifies in the Study table in the database.

The relative agent is designed to enable the relative alignment of entity data and temporal abstractions based on the study to be undertaken. The relative agent is used to realign the temporal abstractions, relative to some point in time of interest that is shared within the temporally abstracted data set, for example as the relative point in time for when an event was apparent for entities.

Many studies can be conducted on the same temporal abstractions, and the same temporal abstractions can be used for many different studies and may require realignment in several different ways. Each aligned temporal abstraction stored in the relative temporal data table will belong to a particular study. The realigned temporal abstractions will form the basis for the optional exploratory and confirmatory data mining performed in later stages of the process.

Studies can be created where no time adjustment occurs as a result of the relative alignment. In these cases, the relative alignment performs a subset selection of entities of interest based on the static information of individual entities.

The relative agent is used to partially support the phase of data preparation within the CRISP-DM model and represents the final step of data preparation for a given study.

Referring to the top horizontal column of FIG. 3, the relative agent uses the relative alignment web service enabling data to be pushed or pulled directly to the relative agent. Data can also be sent directly to the relative agent via a direct connection.

The relative agent has three main functions: (1) retrieve the relevant data and temporal abstractions from the temporal data store, based on the selection specifications given by the user; (2) apply the transformations specified for the study to be undertaken to the absolute timed temporal abstractions to create the set of aligned temporal abstractions, called relative abstractions, as time (start and end times) is relative to the alignment point; and (3) store the relatively aligned abstractions in the relative temporal data store to allow for further processing by the functional agent.

Example of relative alignment tasks may include the following: (i) Neonatal Intensive Care: (a) select all neonatal patients who were diagnosed with nosocomial infection and relatively align the data based on the data of suspected nosocomial infection and include data for the four days before and all days after the suspected nosocomial infection diagnosis; select all patients who were born at 23 weeks gestation and create a study set of data for those patients for the equivalent of their 27-29 gestational 27-29 weeks. (ii) Electricity Grids: (a) align meter data for weekend days where the temperature was >40 C for more than 4 hours the following days temperature was <27 C and select the subsequent 72 hours of meter data (ie to detect a pattern of excessive air conditioner usage in the time following a very hot day in instances where it may not be required.

Again referring to FIG. 3, the next agent of the STDM″$_0$ framework is the functional agent. The functional agent attempts to detect and validate new trends and patterns in the relatively aligned temporal data and includes exploratory and confirmatory data mining. The initial analysis is done using exploratory data mining to enable the discovery of interesting rule sets to investigate further. Exploratory data mining is used to analyze the realigned temporal abstractions, created by the temporal and relative agents, across multiple data streams for multiple entities to explore the data in search of new trends and patterns that can be represented through rule set generation and also known as a hypotheses. The scientific method stages of "make observation" and "invent hypothesis to explain observation" are supported by the exploratory data mining. If a correlation within the data is found, then this can be validated using confirmatory data mining. The validation can be either via testing on further data sets or via the use of null hypothesis testing or both.

The purpose of the analysis is to look for level shifts and trends in temporal data and cross correlate data mining findings across multiple data streams for multiple entities in an attempt to detect previously unknown patterns that may exist in entities with a particular event, and thereby create new hypotheses that can possibly become new rules that can be applied in entity monitoring.

Temporal abstraction as performed in the previous step preserves the temporal aspect of the data, enabling this temporal aspect to be included when performing the exploratory data mining across multiple streams and for multiple entity tasks.

There exists the ability for the user to use alternate data mining techniques in this step; the framework does not restrict a selection of the data mining technique that best matches the mining task. The data mining technique selected must have an awareness of time series data. The result of the exploratory data mining is examinee by the user, and significant rule-sets are selected.

The functional agent is used to support the phase of modelling within the CRISP-DM model. The STDM″$_0$ framework extends CRISP-DM 42 to support the scientific method 44. The parallel between the known CRISP-DM and the scientific method is illustrated in FIG. 4.

Figure 4:
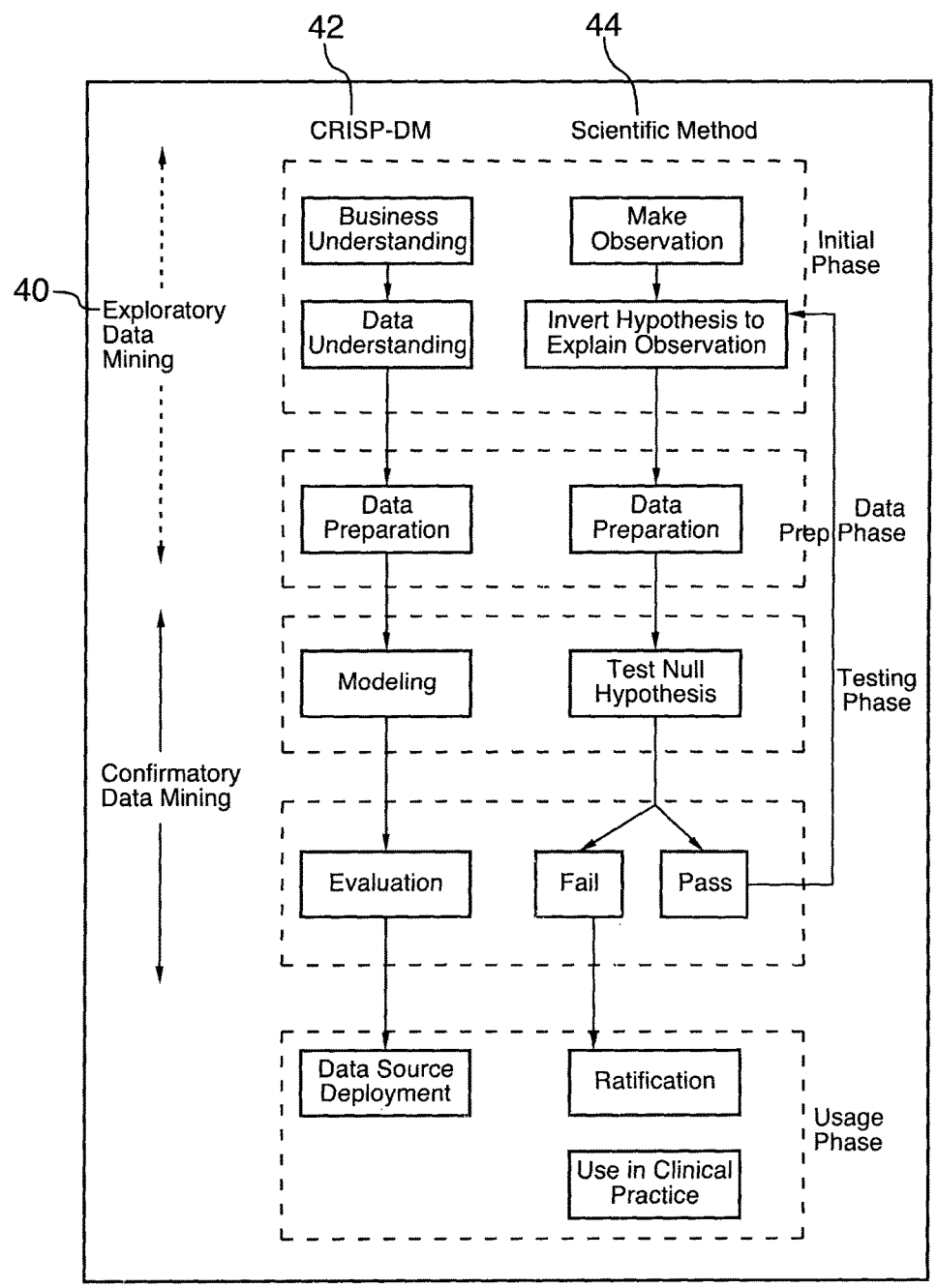
FIG. 4 illustrates a parallel between the known CRISP-DM and the scientific method that is an embodiment of the present invention.

The STDM″$_0$ framework exploratory data mining task 40, as shown in FIG. 4, is part of the data mining rule-set generation and select significant rule sets phases of the extended CRISP_DM model. This task will be completed by the functional agent in the multi-agent framework.

Referring to the STDM″$_0$ agent tasks column, under the functional agent step, a subset of entities, as selected for a given study based on a given hypothesis, and their associated relatively aligned temporal streams can be used as a training set for exploratory data mining. Subsequently in explanatory mode the same hypothesis (without switching to null hypothesis mode) can be run on more data for other subsets of entities as originally selected for the given study or the whole subset that satisfies the study selection criteria for entities.

The incorporation of null hypothesis testing within STDM″$_0$ enables validation of the hypothesis through a confirmatory data mining process and represents an optional step for use within domains where further verification of the resultant rules are required such as but not limited to healthcare. This Confirmatory Data Mining with Null Hypothesis task is performed within the Formulate Null Hypothesis and Run Statistical Processes to test Hypothesis extensions to CRISP-DM. The hypothesis is translated from a hypothesis to a null hypothesis and the validation attempts to disprove the null hypothesis. If the disproving is unsuccessful then the hypothesis holds.

An example of the integration of a null hypothesis test is as follows:

Anecdotal clinical evidence suggests that the correlation of the following two events has a direct association with neonatal instability resulting in unstable heart rate: "Given a hypothetical newborn baby born 5 weeks premature (35 weeks gestational age), a fall in mean blood pressure less than 35 mm Hg (ie the numerical value of their gestational age) is clinically relevant. At all gestations a fall in peripheral oxygen saturation less than 85% for greater than 20 seconds is also clinically relevant."

The temporal agent prepares the initial simple temporal abstractions on mean blood pressure and blood oxygen saturation as per the above and a complex temporal abstraction is prepared to select segments when both occur concurrently. These are relatively aligned to heart rate instability episodes.

In this example, the exploratory data mining performed during the DM Rule Generation and Select Significant Rule set steps by the Functional Agent results in a correlation that supports the anecdotal clinical evidence as above.

The Formulate Null Hypothesis step enables the representation of the rule set as a Null Hypothesis.

For this example a correlation coefficient of 0.8 is used. This hypothesis is thus utilizing a correlation coefficient notation of the form:

$$H_1: \rho_{(X,Y)} > 0.8$$

Where:
  X represents ECG instability and;
  Y represents ABPmean<gestational age for 20 seconds; AND SaO2<85% for the same 20 seconds The effective null hypothesis is represented as:

$$H_0: \rho_{(X,Y)} = 0.8$$

The true null hypothesis is represented as:

$$H_0: \rho_{(X,Y)} < 0.8$$

During the Run Statistical Processes to test Hypothesis step, set out under the $STDM''_0$ Extensions to CRISP-DM model, the null hypothesis is tested against further mixes of test sets to attempt to disprove the null hypothesis. If the null hypothesis can not be disproved, then the hypothesis is considered proven.

Optionally, exploratory and confirmatory data mining can be automated Exploratory data mining can be automated with the system using in turn the time of an event, an entity attribute that represents a date/time point, or temporal abstraction start times to determine relative alignment points for entities that would qualify. Qualifying entities could be chosen iteratively based on restrictions based on entity attribute criteria, event attribute criteria temporal abstraction criteria and/or relative temporal abstraction criteria. Data mining could be automated to attempt to cluster entities based on common behaviours or via other data mining approaches return results where the are strong correlations.

For example, a user may optionally select some data streams or ones that make sense and then use those for further explanatory data mining. A user may choose to perform this step for example to input results that are known based on domain knowledge, to avoid additional system processing to discover known trends.

The functional agent uses the exploratory data mining and confirmatory data mining web services enabling data to be pushed or pulled directly to the functional agent. Data can also be sent directly to the functional agent via a direct connection.

Referring next to the rules generating agent vertical column of FIG. 3, the rules generating agent performs the task of adding the rules created as part of the rule set generation through the exploratory data mining within the functional agent into a rules format that can be represented in a manner to enable insertion into the rules table. A user may evaluate the rule set and decide if it is to be incorporated into the Real-time Rule Base as an active rule for intelligent entity monitoring.

As indicated in FIG. 3, this task is part of the evaluation phase in the extended CRISP-DM model.

Figure 8:
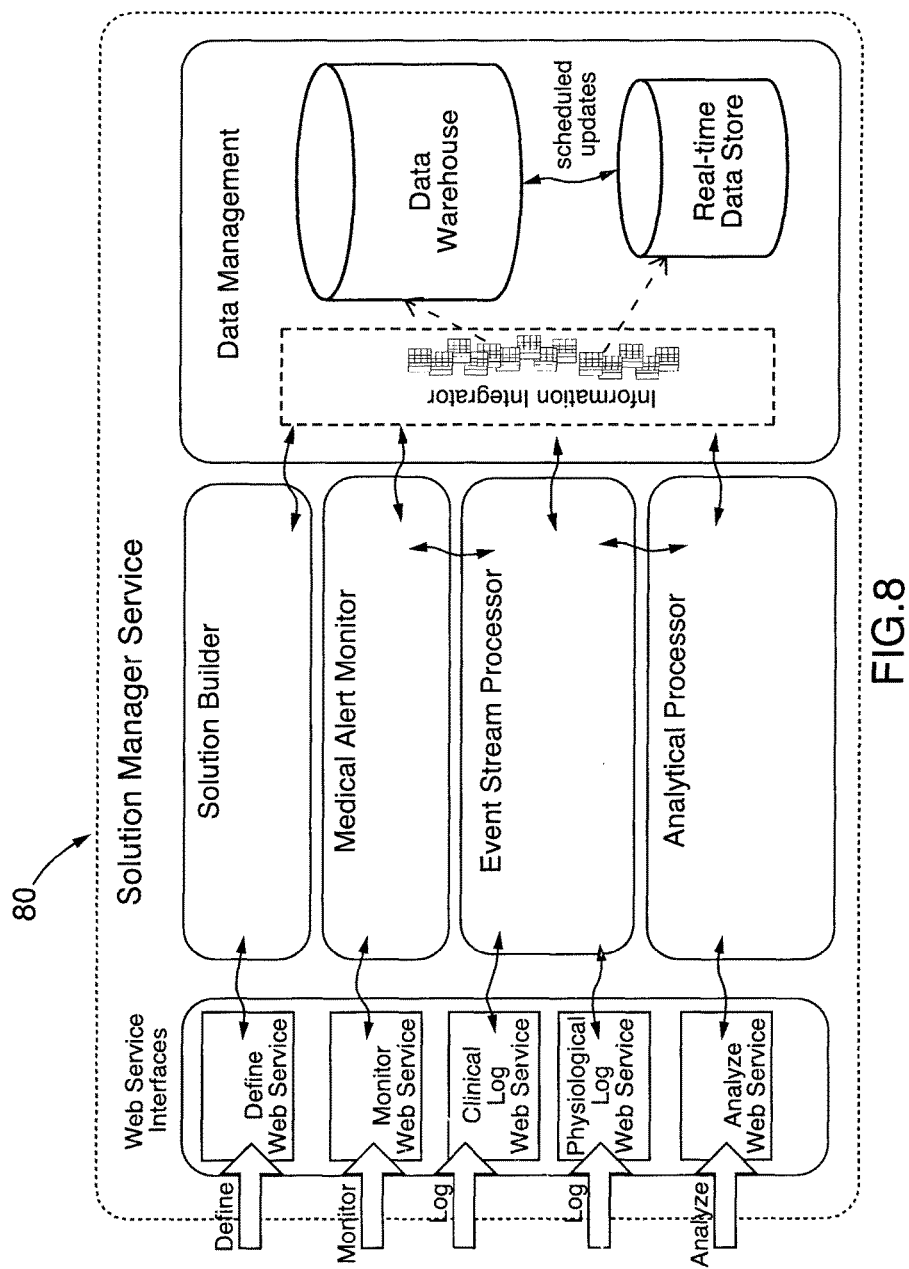
FIG. 8 illustrates a solution manager service for enabling clinicians to carry out the methods of the present invention.

These rules can be utilized by an event stream processor such as that detailed in the solution manager service 80, as shown in FIG. 8, for real-time, or virtually real-time, event monitoring. An event stream processor may incorporate temporal abstraction on real-time data streams to allow the utilisation of temporally abstracted rules for alerting.

The rules generating agent uses the rule management web service enabling data to be pushed or pulled directly to the rules generating agent. Data can also be sent directly to the rules generating agent via a direct connection.

An extended CRISP-DM model satisfying the need for null hypothesis testing is illustrated in FIG. 4. The extended CRISP-DM model is used to support the data mining model in the $STDM''_0$ framework. This extension to the CRISP-DM model illustrates the incorporation of the null hypothesis testing component of the Scientific Method approach within the Confirmatory Data Mining Modelling and Evaluation components of the extended CRISP-DM model. The following sections detail the extended CRISP-DM implementation within the $STDM''_0$ framework. In particular the extensions within the Modeling and Evaluation components.

Data Understanding

The data understanding phase involves various tasks associated with collection and familiarization with the collected data. The data is described and investigated, and any data quality problems are identified. The data understanding phase uses the services of the processing agent in the multi-agent system to complete part of the local collection and clean-up task in the $STDM''_0$ framework.

Data Preparation

The data preparation phase includes all action involved in transforming the initial unprocessed data into the final dataset to be fed into the data mining took. It includes activities such as selecting and cleaning the data, constructing and integrating data sets and formatting the data to be ready for data mining. The data preparation phase uses the services of three agents in the multi-agent system. The processing agent finalizes the initial preparation started in the data understanding phase, ready for the temporal agent to perform the temporal abstractions on the temporal data, before the relative agent performs the relative re-alignment of the data in accordance with the study undertaken.

Modeling and Evaluation

The modelling phase includes selecting and applying modeling techniques. This phase includes data mining rule-set generation, select significant rule-set, formulate null hypothesis, and run statistical processes to test hypothesis. The Formulate Null Hypothesis and Run Statistical Processes to Test Null Hypothesis represent the $STDM''_0$ framework implementation of the CRISP-DM extensions within the modelling and evaluation components to support the Test Null Hypothesis and Pass/Fail test within the Scientific Method. All the modelling and Evaluation phases are performed by the functional agents in the multi-agent system and are mapped to the $STDM''_0$ framework as described below.

Data Mining Rule-Set Generation and Select Significant Rule-Set

The data mining rule set generation phase is the phase where exploratory data mining is conducted. In the $STDM''_0$ framework exploratory data mining is performed on relatively aligned temporal abstractions, including multiple streams for multiple entities. The results of the exploratory data mining are used when moving to the select significant rule-set phase.

(i) Formulate Null Hypothesis

The formulate null hypothesis phase uses the output of the select significant rule set phase, where significant rule sets are selected from the results of exploratory data mining. A null hypothesis is created for any results that indicate interestingness and further investigation.

(ii) Run Statistical Processes to Test Null Hypothesis

Another part of the modelling phase, run statistical processes to test null hypothesis phase follows the formulate null hypothesis phase. The run statistical processes to test null hypothesis phase performs the confirmatory data mining with null hypothesis task of the $STDM''_0$ framework, aiming to prove or disprove the null hypothesis.

Data Source Deployment

The Data Source Deployment component of the Extended CRISP-DM model is implemented through the functions of the Rules Generating Agent.

Data Storage

Figure 6:
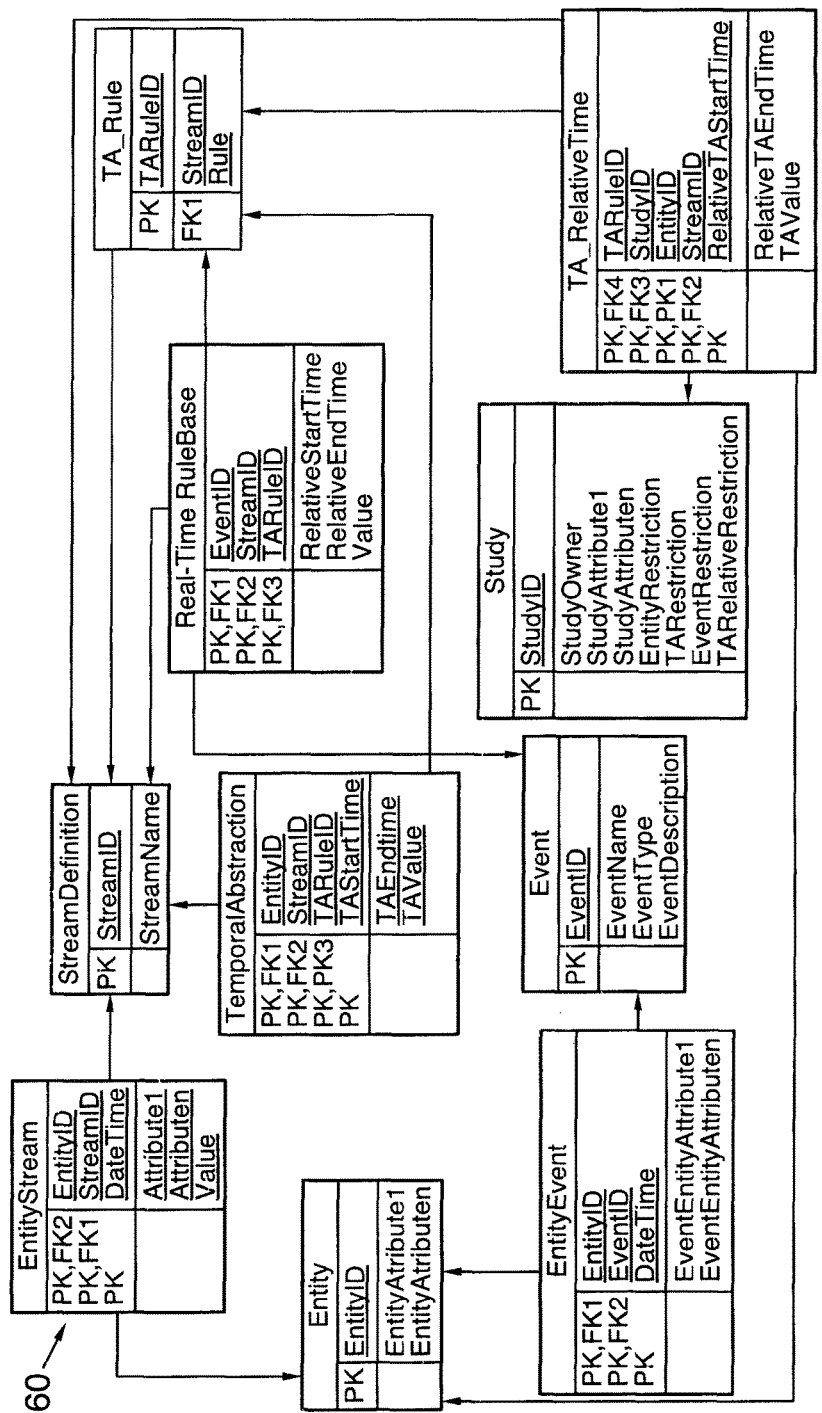
FIG. 6 illustrates a data storage schema for implementing the $STDM''_0$ framework that is an embodiment of the present invention.

FIG. 6 illustrates a data storage schema 60 for implementing the $STDM''_0$ framework. A further example of a data storage schema as applied to support neonatal intensive care is shown in FIG. 7.

The static entity data for the entities in the framework may be recorded n an Entities table. The Entity table contains either identified or research de-identified historical clinical static data for entities. The attributes of the Entity table are EntityId, which is used to link the content of the Entities table to the content of the Entity Event, Entity Stream, TemporalAbstraction, TA_RelativeTime and EntityDiagnosis tables. The relationship between the Entity table and the EntitySteam is one-to-many, the relationship between the Entity table and the TemporalAbstraction table is one-to-many, the relationship between the Entity table and the TA_RelativeTime table is one-to-many and the relationship between the Entity table and the EntityDiagnosis table is one-to-many. The entity table can then contain any number of EntityAttributes listed in FIG. 6 as EntityAttribute$_1$ through EntityAttribute$_n$.

As shown in FIG. 7 this can be implemented to support neonatal intensive care. Within this context, entities are patients. The entity table is shown as a patient table with a Patient_ID rather than EntityId and a series of EntityAttributes (Birthtimedate, BirthGestationalAge, Gender, BirthWeight, BirthLength, BirthHeadC).

The Event table stores definition information about the types of events that can occur to entities at a given point in time. The Event table contains the EventID code which is a unique identifier for each event together with the EventName containing a human readable name for the event. The EventType enables events to be grouped, for example, in the case where events could relate to diagnosis, recording observations, lab results and growth recording. EventDescription contains further textual details describing what the event is.

The EntityEvent table contains a record of all events that are listed in the events table that occur to a given entity have been diagnosed with. The attributes that comprise the primary key for this table are EntityId, which may, for example, be used to link a diagnosis to a particular entity, EventID, which may for example, used to link a record for an entity to a particular type of diagnosis, and Date and Time. A particular entity could be diagnosed with the same condition several times during the data collection process, so it may be necessary to include all of these attributes in the concatenated primary key. In FIG. 7, the Entity/Event table has been populated as a Patient/Diagnosis table, wherein the last attribute, Severity, is used to record the severity of the condition, if appropriate.

Referring back to FIG. 6, the identified or research de-identified raw sensor data for the various sensors for each entity is stored in the EntityStream table.

The attributes contained in the EntityStream table are EntityId, Stream_ID, Date and Time for the reading, a Value and a series of other Attributes, denoted as Attribute$_1$ to Attribute$_n$ as required such as but not limited to Location and Position, as set out in the clinical research schema in FIG. 7. The EntityId attribute is used to link the sensor data to the correct entity in the Entities Table. There is a many-to-one relationship between the EntityStream table and the Entities Table. The Stream_ID is used to identify which sensor and possibly within that which stream within the sensor the reading is for, and is linked to the StreamDefinition table. There is a many-to-one relationship between the EntityStream table and the StreamDefinition table.

Each stream that an entity has readings for must be identified. The StreamDefinition table contains as attributes the id, SensorId, and name, StreamName, for each stream entities may have reading values for. The SensorId is used in the EntityStream table as a foreign key to fink to the StreamDefinition table to enable identification by name of each stream.

The rules for how to abstract particular streams are contained in the TA_Rule table of FIG. 6. Each stream may be linked to more than one rule to create more than one abstraction.

The attributes in the TA_Rule table are RuleID, which contains the id of a particular rule, the SensorId, which links the TA_Rule table to the StreamDefinition table and is used to identify which type of parameter the particular rule is applied to. The Rule attribute contains the details of the particular rule. The TA_Rule table has a many-to-one relationship to the StreamDefinition table, which indicates that a particular StreamDefinition can have more than one temporal abstraction rule applied to it.

The temporal abstractions created from the entity's streams are stored in the TemporalAbstraction table. The abstractions may be created by applying previously defined abstraction rules, stored in the TA_Rule table of FIG. 6, to the data values for the individual entities' streams, which are found in the EntityStream table. The raw data for each sensor data stream for each entity is extracted from the EntityStream table, abstracted, and the resulting abstractions stored in the TemporalAbstraction table.

The attributes of the TemporalAbstraction table are EntityId, used to link a particular abstraction to a particular entity, SensorId, which is used to relate the abstraction to a particular stream, AbstractionValue (TAValue), showing the result of the abstraction (values could for example be high, low, normal, rising . . . and so on), ActualStartTime (TAStartTime), which is the time that the abstraction became true, and ActualEndTime (TAEndtime), which is the time when the particular abstraction no longer held true, it ended.

The temporal abstractions stored in this table are created by applying the rules contained in the TA_Rule table to the relevant stream of a entity, stored in the EntityStream.

The TemporalAbstraction table is finked to the Entity Table in a many-to-one relationship, indicating that a particular entity can have many abstractions stored in the table. There is a many-to-one relationship between the TemporalAbstraction table and the StreamDefinition table, which indicates that a stream can have several abstractions performed on it.

In a traditional data warehouse setting, where raw data is copied into the data warehouse and aggregated via a periodic load followed by batch aggregations, the temporal agent can be, for example, implemented as an agent in the database management system (DBMS) housing the data warehouse. This could be utilising scripts within DB2 (a trade-mark) for example. In this instance, for example, the five functions listed above would be implemented as follows:
1) Query the TA_Rule table and select all the rules from the rule column of each row of the selected rows in the table that were active.
2) Build a DB2 script that contained an insert statement for each temporal abstraction rule as listed in rule column of the TA_Rule table. The insert statement would contain the select statement that performs the temporal abstraction function for the date range specified to insert rows in to the TemporalAbstraction table.
3) Storage would be achieved by running the script and initiating the insert statements
4) Complex abstractions would select data from the newly created simple abstraction insert statements that are performed before the complex abstractions.
5) Storage of complex abstractions would be achieved by running the script and initiating the insert statements for the complex abstractions.

The use of the present invention in connection with stream based manipulation illustrates the advantages of the present invention. Within the stream computing paradigm, where data is manipulated as a stream as the data arrives in real-time, the temporal agent could be a stream computing program analysing the streams of data as the data arrives in real-time or sourcing data from the data warehouse tables and creating a series of resultant slower frequency streams that are simple or complex abstractions and then loading them in real-time in the database. In this implementation, in addition to a periodic copying of the raw data streams to the data warehouse environment, a periodic copying of the temporal abstraction data would also be required. In this instance for example, the five functions listed above would be implemented as follows in the real-time environment:

1) Use the information contained in the TA_Rule table to drive the creation of the real-time streaming modules for each rule. In IBMs Infosphere Streams for example this would result in the creation of a series of SPL graph programs.
2) Each streaming module representing a simple abstraction would read in the source raw stream and the associated required static data and write out the resultant slower frequency output steam. These real-time streaming modules would be deployed against each entity that is being monitored by the real-time streaming environment.
3) Storage would be achieved by writing the output stream or streams to the database.
4) Similarly to 1), complex abstractions would be implemented as streaming modules that read in the created output streams from 2) from the real-time stream as it is generated or the by selecting the data once it is written to the database from the newly created simple abstractions that are performed before the complex abstractions.
5) Storage of complex abstractions would be achieved by writing the output stream or streams to the database.

The Study table of FIG. 6, which specifies a particular alignment, holds the information about any relative rules that may need to be applied to the abstractions stored in the TemporalAbstraction table for each study. Depending on a particular study undertaken, the temporal abstractions may need to be re-aligned relative to a particular point in time, such as the point of diagnosis, if the behaviour of certain parameters in the time leading up to a diagnosis is to be studied. In that case the absolute point in time when a particular abstraction was true is not important, rather it is the relative point in time for each entity in relation to the entity's diagnosis time that is relevant.

There is an entry in the Study table for each study. The attributes of the Study table are Study_ID, a unique identifier for each study and used to link to the TA_RelativeTime table. The Study table could have zero to many study attributes such as but not limited to Study Name and Study Owner denoted in the table in FIG. 6 as $StudyAttribute_1$ through $StudyAttribute_n$. The Study_Owner attribute is used to identify the user conducting the particular study. To enable the restriction, if required, of entities to those of interest, the Study table contains an attribute to define the nature of the entity restriction through the EntityRestriction attribute. To enable the restriction, f required, of events to those of interest, the Study table contains an attribute to define the nature of the event restriction through the EventRestriction attribute. To enable the restriction, if required, of temporal abstractions to those of interest, the Study table contains an attribute to define the nature of the temporal abstraction restriction through the TARestriction. To enable the restriction, if required, of relative alignments to those of interest, the Study table contains an attribute to define the nature of the relative alignment restriction through the TARelative attribute.

An example of an implementation of this table to support neonatal critical care is shown in FIG. 7 as the Study table where the Entity has been replaced with patient.

An example of the definition of a study is as follows: Researchers wish to select all patients who were born at less than 30 weeks gestation. In this example, the event of interest is episodes of neonatal bradycardia, which for the study is defined as a fall in heart rate below 100 beats per minute. The temporal abstraction of interest may be the simple TA of when the heart rate falls below 100 beats per minute. The relative alignment restriction may be to only select temporal abstractions that occur up to 36 hour before the date and time of that neonatal bradycardia event. Of note in this example is that the same entity can have multiple events occur, resulting in multiple sets of relatively aligned data for that patient.

An example of the study restriction information as implemented in a database management system in SQL would be a series of select statement where clause components in each of the EntityRestriction, TARestriction, EventRestriction and TARelativeRestrictions attributes for restriction of rows from the Entity, TemporalAbstraction, EventRestriction and TA_Relativetime tables respectively. This could then be used in a composite insert statement to insert the data into the TA_RelativeTime table.

Referring again to FIG. 6, the TA_RelativeTime table holds the abstractions that have been realigned in time relative to a point in time that has been deemed interesting by the user who owns the study of the relatively aligned abstraction in the table. The data for multiple studies can be stored in the TA_RelativeTime table.

The attributes of the TA_RelativeTime table are very similar to the attributes in the TemporalAbstraction table, however the ActualStartTime and ActualEndTime have been replaced with RelativeStartTime and RelativeEndTime, which will be times relative to a point in time deemed interesting to the owners of the study the entry belongs to. A Study_ID attribute has been added to link the relative abstraction to a particular study in the Study table. The relationship between the TA_RelativeTime table and Study table is a many-to-one relationship, as there can be many entries in the TA_RelativeTime table that belongs to a particular study.

In this context, the relative agent can, for example, be implemented as an agent in the database management system (DBMS) housing the data warehouse. This could be utilising scripts within DB2 for example. In this instance for example, the three functions listed above would be implemented as follows;

1) Query the Study table and select all the studies and use the information contained in each column to populate the information within the resultant insert statement to create rows in the TA_RelativeTime table.
2) Build a DB2 script that contained an insert statement for each relative alignment rule as created from 1). The insert statement would contain the select statement that performs the relative alignment function for the date range specified to create rows in the TA_RelativeTime table.
3) Storage would be achieved by running the script and initiating the insert statements into the TA_RelativeTime table.

Within the stream computing paradigm, where data is manipulated as a stream as the data arrives in real-time, the relative alignment agent could be a stream computing program analysing the streams of temporal data as the data arrives in real-time or sourcing data from the data warehouse tables and creating a series of resultant slower frequency streams that are simple or complex abstractions and then loading them in real-time in the database. In this implementation, a periodic copying of the relative data would also be required to create a relative data copy for use for data mining. In this instance for example, the five functions listed above would be implemented as follows in the real-time environment:
 1) Use the information contained in the Study table to drive the creation of the real-time streaming modules for each rule. In IBM InfoSphere (a trade-mark) Streams for example this would result in the creation of a series; of Streams Processing Language (SPL) graph programs;
 2) Each streaming module representing a study relative alignment would read in the temporal abstraction streams and the associated required static data and write out the resultant relatively aligned streams. These real-time streaming modules would be deployed against each entity that is considered within the scope of the particular study; and
 3) Storage would be achieved by writing the output stream or streams to the database.

In addition to the above tables which form part of the $STDM''_0$ framework, the possibly resulting rules created from hypotheses that are a result of the processing in the $STDM''_0$ framework, may be stored in the Real-time Rule Base table, shown in FIG. 6, that is accessible for use by real-time patient monitoring such as the Event Stream Processor within the SMS. This table may be external to the $STDM''_0$ data store.

FIG. 6 demonstrates an example of the Real-time Rule Base table where for each EventID that has been the subject of a study, the temporal abstractions (TARuleID) related to a certain stream (StreamID) can be defined based on their relative distance from the event and where required an associated value. There can be multiple temporal abstraction rules for a stream each likely to be at different relative distances from an event. There can be multiple temporal abstractions across multiple stream for each event.

Solution Manager Service

Figure 9:
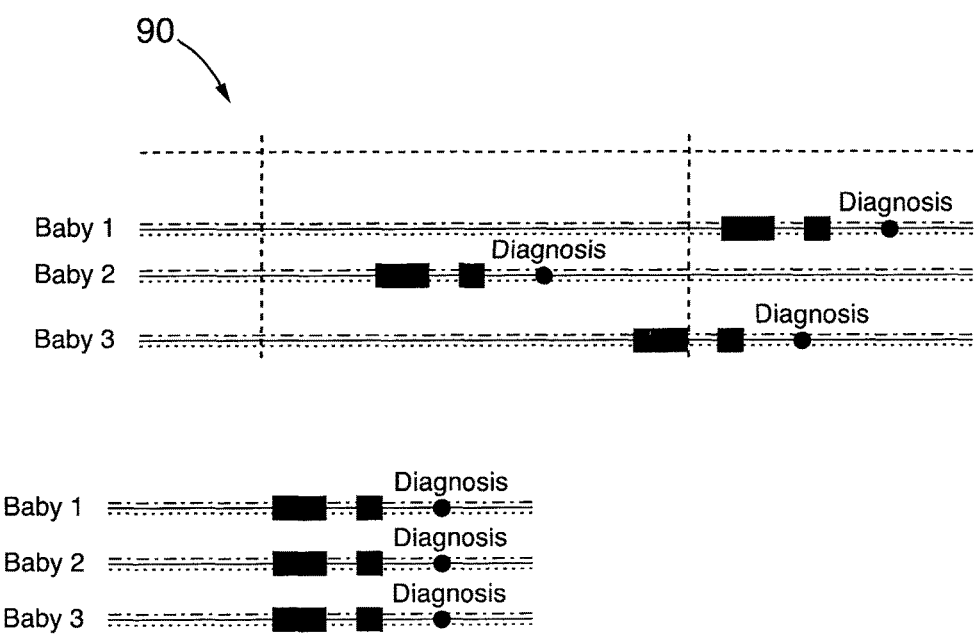
FIG. 9 illustrates an example of relative alignment of ECG instability streams that may occur in an embodiment of the present invention.

The Solution Manager Service (SMS) is an Intelligent Decision Support System (IDSS) to support neonatal clinical management and research, in one implementation of the present invention. Interaction with the solution management service may be achieved via a series of web services. The SMS 90, as shown in FIG. 9, may contain six components, in a particular representative implementation of the invention:

Solution Builder is a build-time component that captures metadata that is used to setup and initialize the runtime components and the Data Management layer.

Medical Alert Monitor is a run-time component enabling Neonatalogists to define and change complex medical alert rules.

Event Stream Processor provides a scalable data staging environment to continuously integrate and transform events to support complex medical alerts.

Analytical Processor provides a run-time interface for retrieving near real time patient data or to perform clinical trial analysis at patient or summary levels from data located in the data warehouse or real-time data store within the data management layer.

Data Management provides persistent storage of build-time metatdata, medical rules and run-time physiological and clinical data stored in either the data warehouse or active rule and data store together with the temporal abstraction (TA) rule base.

Web Services Interfaces provides access to these components via a set of web services. This paper describes research relating to the Solution Manager Service and Data Collection Units.

The SMS supports both real-time processing, which in the context of the neonatal example implementation represents real-time intelligent patient monitoring, and data mining.

The $STDM''_0$ framework components as shown within FIG. 3 map to the SMS components within FIG. 8 as follows:

The Clinical Log Web Service within the SMS performs the function of the Static Data Collection Web Service in the $STDM''_0$ framework.

The Physiological Log Web Service within the SMS performs the function of the Stream Data Collection Web Service in the $STDM''_0$ framework.

The Analyse Web Service within the SMS represents a set of web services in the $STDM''_0$ framework namely: Temporal Abstraction Web Service, Relative Alignment Web Service, Exploratory Data Mining Web Service, Confirmatory Data Mining Web Service and Rule Management Web Service A part of the SMS Event Stream Processor function is to enact the Processing Agent to move the data from the SMS Real-time Data Store to the SMS Data Warehouse.

The Analytical Processor within the SMS is enacted through the remaining four types of Processing Agents within the $STDM''_0$ framework namely: Temporal Agent, Relative Agent, Functional Agent and the Rules Generating Agent.

The $STDM''_0$ framework data model as shown in its generic form in FIG. 6 and an example form for neonatal intensive care in FIG. 7 is a representation of the data warehouse within the SMS.

The SMS Clinical Log Web Service and Physiological Log Web Service load data into the Real-time Data Store copy of the $STDM''_0$ framework data model Entity and EntityStream tables respectively and represent the continuously populated tables to support the real-time patient monitoring. A copy of the Temporal Abstraction table may also exist within the Real-time Data Store in the instance where the contents of this table is being created in real-time through such techniques, but not limited to, stream programming. The $STDM''_0$ framework Processing Agent as a component of the SMS Analytical Processor copies data for population within the $STDM''_0$ framework data model Entity, EntityStream and optionally the TemporalAbstraction data tables of the SMS Data Warehouse from the matching tables within the SMS Real-time Data Store as a periodic incremental load.

The SMS Medical Alert Monitor and its supporting Monitor Web Service support functions required for real-time intelligent patient monitoring.

The SMS Solution Builder and the Define Web Service can be used to initially define the tables required for the real-time intelligent patient monitoring within the SMS Real-time Data Store and the $STDM''_0$ framework data model tables within the SMS Data Warehouse.

Overview of Service Based Multi-Dimensional Distributed Temporal Data Mining ($SDTDM_O$)

Figure 11:
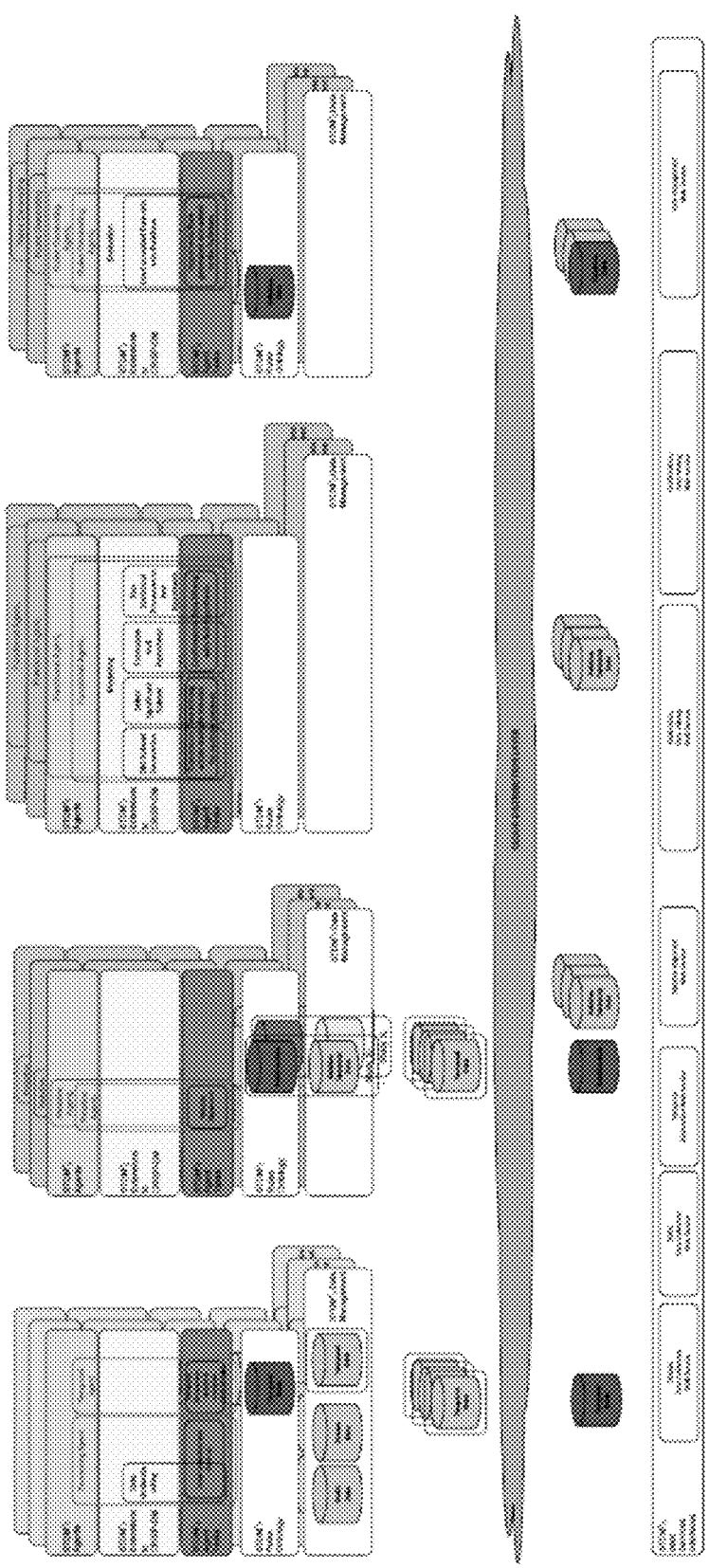
FIG. 11 shows a Service Based Multi-Dimensional Distributed Temporal Data Mining (SDTDM$''_0$) of an embodiment of the present invention.

The present invention may provide a Service Based Multi-Dimensional Distributed Temporal Data Mining ($SDTDM''_O$). For example $SDTDM''_O$ may be incorporated in an embodiment of the present invention, such as that shown in FIG. 11. The $SDTDM''_O$ framework may be incorporated into, or otherwise merged with, the $STDM'_O$ model 110, to provide the functionality that is otherwise lacking in the $STDM''_O$ model. The present invention may incorporate a multi-dimensional distributed data mining framework that provides a structure to support multi center studies and manages the Temporal and Relative Rule tables (as previously described) in a distributed environment while maintaining consistency across the distributed sites. An embodiment of the present invention having the $SDTDM''_O$ framework incorporated therein may be su table for use in clinical research.

The Temporal Agent of the present invention may be operable to manage physiological data being used by the $STDM''_O$ framework and to help to create temporal abstractions based on the temporal rules. As an example, the main elements in this phase may be: the creation of the simple abstractions for individual data streams for individual patients, which are stored in the $STDM''_O$ temporal data store; and the creation of complex abstractions based on any rules found in the temporal rules table, which are also stored in the $STDM''_O$ temporal data store.

Figure 12:
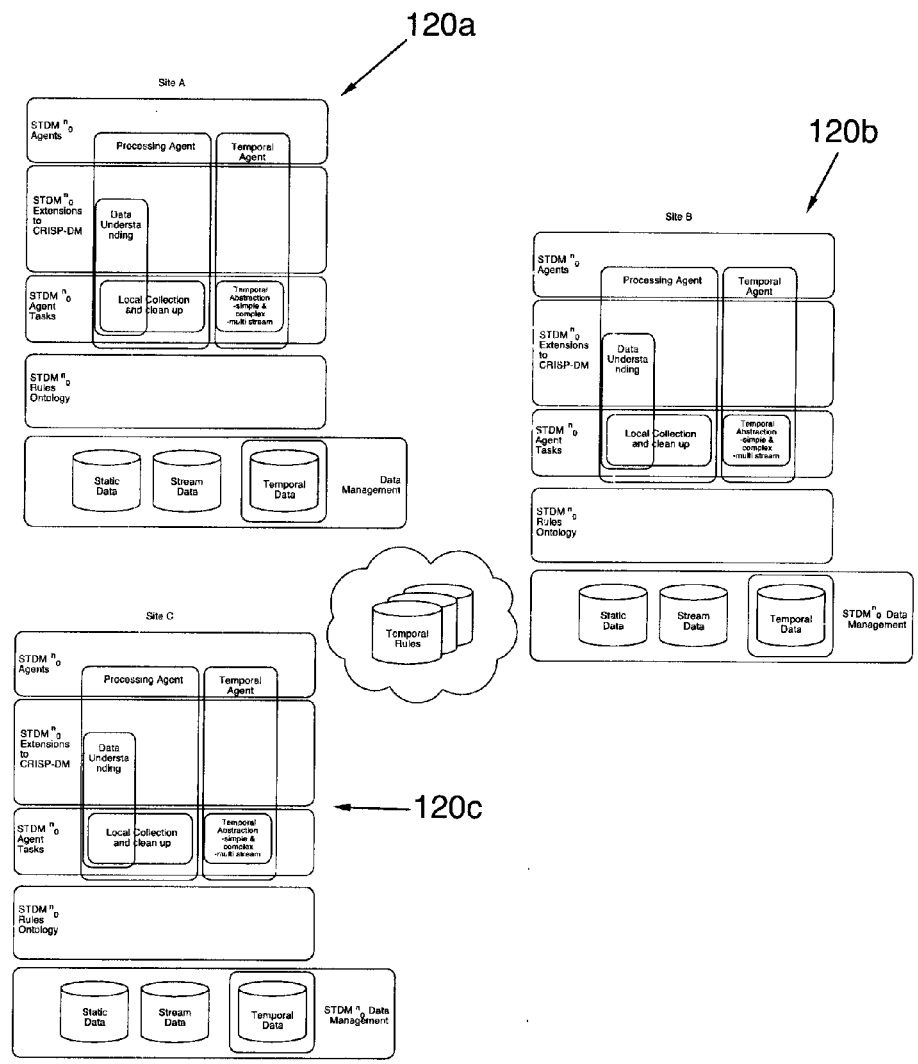
FIG. 12 shows an embodiment of the present invention wherein the Temporal Rules are decentralized.

Within the architectures of the $STDM''_O$ model the creation and storage of Temporal Abstractions and Temporal Rules may be local to each site and may lack a mechanism for distribution. In a multi-dimensional environment, wherein the $SDTDM''_O$ framework is incorporated (or otherwise merged), the physiological data that is being retrieved may come from multiple sites. The multiple sites may produce data that is not the same in terms of data structure or even data frequency, as described herein. A skilled reader will recognize that it would not be very efficient to have multiple local stores of temporal data and temporal rules applicable to the varying data, for example, such as multiple local stores of temporal data and temporal rules applicable to data from each site. However, due to current health care policies and improved patient privacy concerns, it may be required that the static and stream data, as well as the Temporal Abstractions, exist locally at each site. The Temporal Rules, however, do not contain patient identifying information and thus may be decentralized to exist are sites 120a, 120b, 120c that are remote from one another, for example, as shown in FIG. 12.

Several advantages may be the benefits of de-centralizing data, such as the following: (i) keeping the Temporal Abstractions and Rules consistent across different sites; (ii) better controlling the security of the data because there is only one location to manage; (iii) providing better accessibility to the data through a controlled and secure environment; and (iv) creating a modular environment in regards to resource management.

The task of decentralizing the Temporal Rules may begin by moving elements of the framework into the central data server that will act as a cloud distribution layer across all participating sites. The following four steps are possible steps in a method of applying a distributed approach: (1) the physiological data may be retrieved from the physiological data store for each parameter for each patient; (2) a link may be made with the cloud distribution layer in order to retrieve the relevant abstraction rules from the temporal rules table, which may then be applied to the physiological data; (3) the simple abstractions that may be created for individual data streams for individual patients may then be stored locally at each site (they may also be tagged with a SITE_ID for ease of identification of their source site for comparison studies); and (4) complex abstractions may be created from the simple abstractions using the temporal rules table. Once completed, the newly created complex abstractions may also be stored locally in the same TA tables and tagged for easy identification.

The Relative Agent may play an important role in clinical research studies and can greatly benefit from a distributed framework. The Relative Agent may require access to the abstractions created by the Temporal Agent, as well as to the clinical information of the individual patient relative to the time of the study of interest. In order to enable this functionality in a distributed structure, the distributed framework may make use of the Relative Alignment Web Service which may act as the gatekeeper for data access. It is important to note that different research studies may use the same temporal abstractions. For this reason, the central data server may contain a relative temporal data table specific to each study. Abstractions that have been relatively aligned may be stored in the relative temporal data store and may also be tagged for easy identification.

Figure 13:
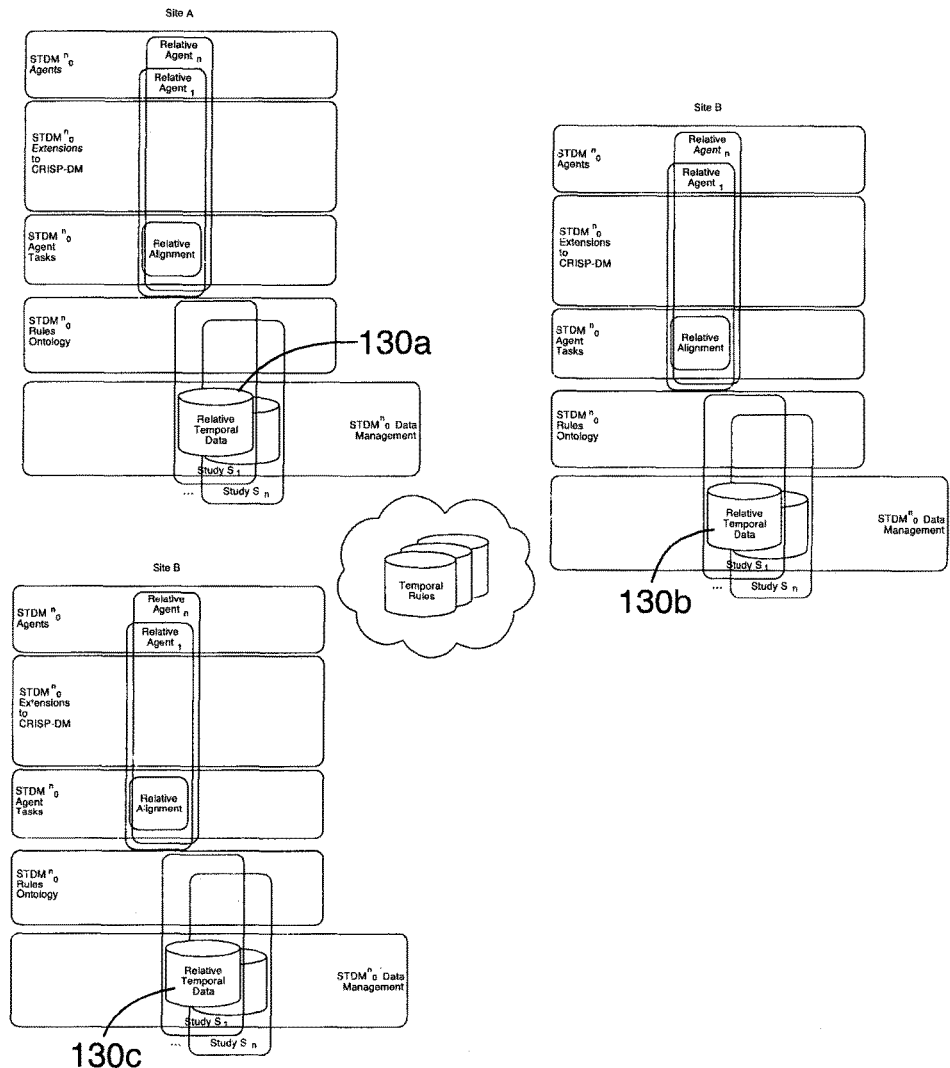
FIG. 13 shows an embodiment of the present invention wherein the Distributed Relative Agent is decentralized.

By decentralizing the Relative Rule data, as shown in FIG. 13 for example, so that the Relative Rules data 130a, 130b, 130c is decentralized to exist at sites remote from one another, it may be possible that the present invention may be operable to enable multicenter studies to take place simultaneously. Decentralization of the Relative Rules may also allow for the possibility of cross comparison of results between similar research studies taking place at the same time.

The present invention may further include distributed functional agents and rules generating agents. The functional agent may perform data mining tasks and be operable to detect interesting trends and patterns within data. A distributed functional agent may, for example, detect trends and patterns within data relating to a particular research study. The distributed functional agent may also, as another example, recognize data relating to a particular research study within a collection of data streams and may detect trends and patterns within the research it identifies as being related to a particular research study, and thereby produce results that provide the detected trends and patterns relevant to a particular research study.

In an embodiment of the present invention, exploratory data mining may be used to analyze realigned temporal abstractions across multiple data streams for multiple patients in order to detect new trends and patterns that might present in the data prior to, or after, an event of interest. Once possible trends and patterns have been discovered, they may be evaluated by a clinician who will use the trends and patterns to develop a hypothesis, for example, such as a hypothesis relating to the factors that may lead to the onset of a condition. The results of the exploratory data mining exercise may further identify rules of significance that should be; considered or researched further in the context of patient care; removed from policies/procedures; or implemented into policies/procedures.

The steps involved in the distribution of agents in an embodiment of the present invention may include the following: Exploratory Mining may be utilized to analyze the realigned temporal abstractions (from the Relative Agent) across multiple data streams for multiple patients in order to detect new trends and patterns that might present in the data; a Rules Generating Agent may utilize exploratory functional rules in the creation of a new Rule Base Data table which may be stored centrally; and an Event Stream Processor may connect with a Rule Base Data table for the application of abstractions on real-time data streams.

Figure 14:
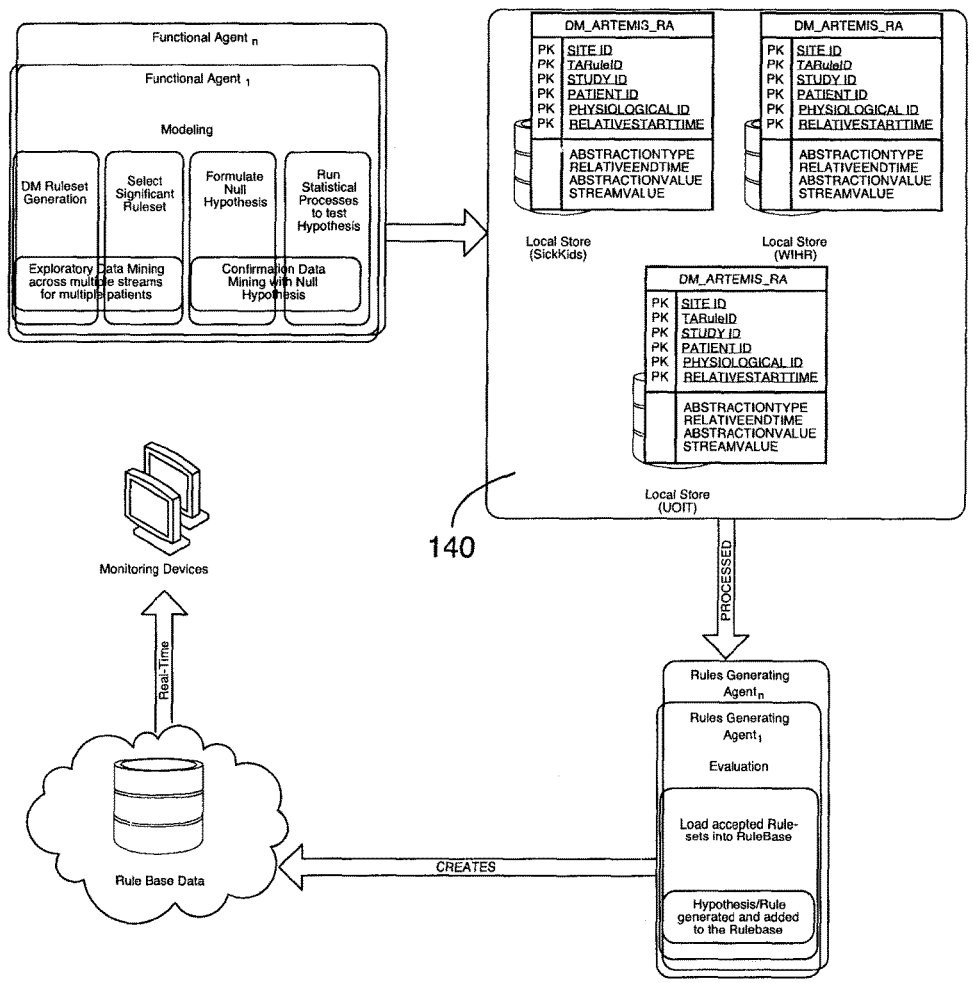
FIG. 14 shows an embodiment of the present invention having distributed functional generating agents and rules generating agents.

FIG. 14 shows an example of a collection of possible local stores 140 (said collection may include one or more local stores) that may be incorporated in an embodiment of the present invention.

Figure 15:
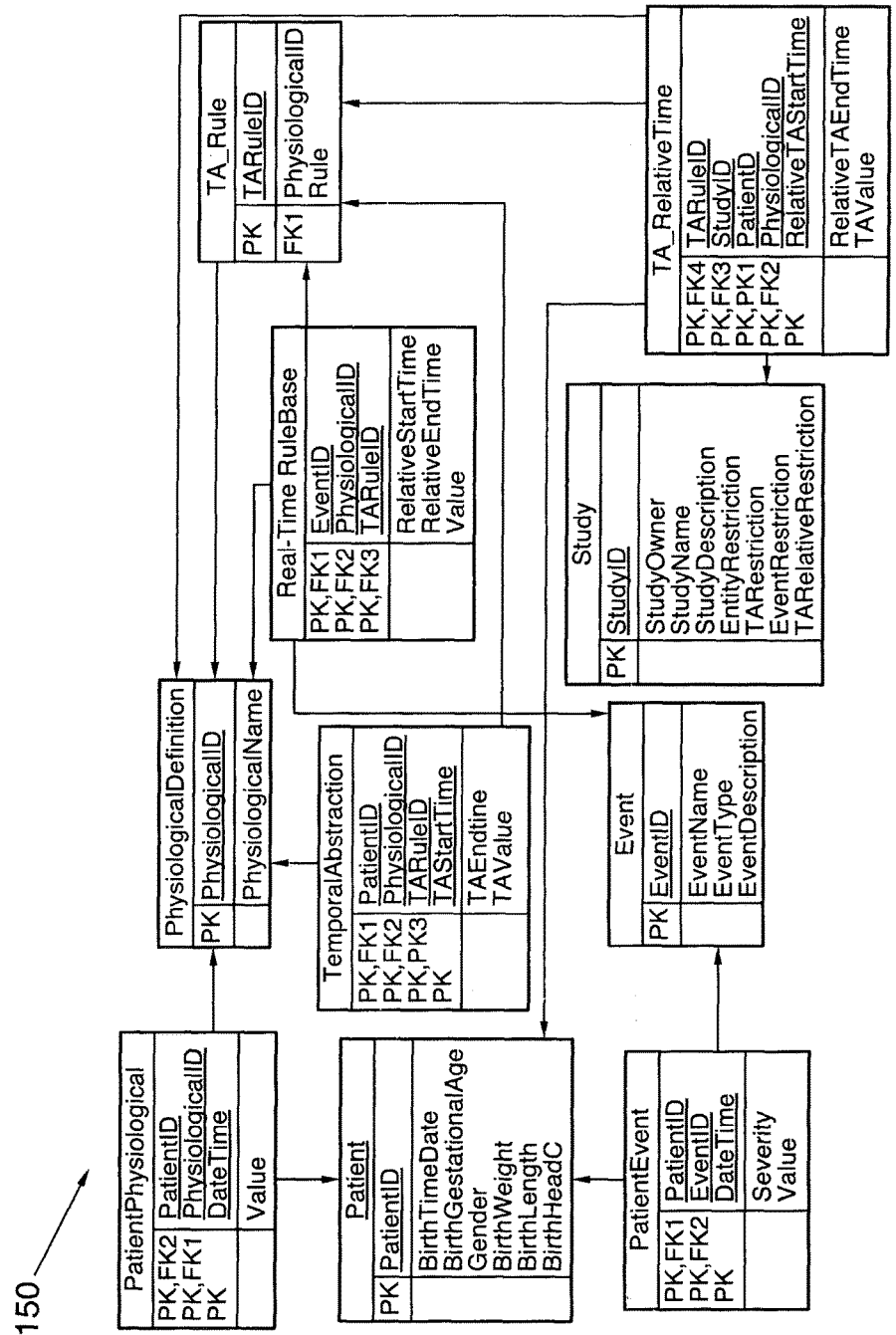
FIG. 15 shows an example of an overall data storage scheme for the STDM$''_0$ that may be included in a possible embodiment of the present invention.

An example of a possible overall data storage schema 150 for the STDM''$_0$ framework of an embodiment of the present invention is shown in FIG. 15. To implement the SDTDM''$_0$ framework several components of the data storage schema may be distributed and the multiple changes may occur, as described herein.

Embodiments of the present invention incorporating a SDTDM''$_0$ framework may include a variety of data storage means. The data storage means may involve a database structure. The data base structure may be utilized to store data received by the present invention, data analyzed or processed by the present invention, as well as data relating to functions or other operability of the present invention, including rules for the invention. The following details provide descriptions of possible data storage that may be included in the present invention, or utilized by the present invention, in possible embodiments of the present invention that utilize a data base structure. A skilled reader will recognize that these descriptions are provided as examples only, and that other data storage means are possible in embodiments of the present invention.

Temporal Rules

In one embodiment of the present invention a TA_Rule table may contain rules that may be utilized to direct how to abstract particular physiological parameters from data processed/analyzed by the present invention. Each physiological parameter may be linked to multiple rules and may therefore create more than one abstraction. The TA_Rule table may be capable of containing the entire SQL abstraction query that needs to be run to abstract particular physiological parameters. The present invention may locate and extract the relevant rule to be utilized by the present invention to undertake particular functions or other operabilities from the TA_Rule table during its operation.

There may be several attributes in the TA_Rule table. For example, one embodiment of the present invention may include three attributes in the TA_Rule table. These three attributes may include: (i) the TARuleID which contains the unique ID of a particular rule; (ii) the PhysiologicalID which links the TA_Rule table to the PhysiologicalDefinition table, and is used to identify which type of parameter the particular rule applies to; and (iii) the Rule attribute which contains the details of the particular rule including the SQL query needed to run the rule. The TA_Rule table may have a many to one relationship to the PhysiologicalDefinition table, which indicates that a particular PhysiologicalDefinition can have more than one TA rule applied to it.

Temporal Abstraction Data

In one embodiment of the present invention, the Temporal Abstraction table may contain TAs created from the patient's physiological parameters. The temporal abstractions stored in this table may be created by applying the rules contained in the TA_Rule table to the relevant physiological parameter of a patient. Said physiological parameter of a patient may be included in the data relating to the patient that is received by the present invention. The PatientID attribute may be used to link a particular abstraction to a particular patient, the PhysiologicalID attribute may be used to relate the abstraction to a particular physiological definition.

In one data base that may be utilized by the present invention a Temporal Abstraction table may include fields relating to the abstraction of a particular physiological definition. For example, in such a data base the field ABSTRACTIONTYPE may indicate the type of abstraction, for example, such as a trend or a level shift. In the same data base the field ABSTRACTIONVALUE may store the results of the abstraction. The results of the abstraction may include values that indicate an increase, decrease or a range of values from high to normal. Also in the same data base, the field ACTUALSTARTTIME may indicate attributes relating to the time that the abstraction became true, and the field ACTUALENDTIME may indicate attributes relating to the time when the particular abstraction was no longer true.

The Temporal Abstraction table may be linked to the Patient table in a many to one relationship. This relationship between tables may imply that a particular patient can have many abstractions stored in the table. The Temporal Abstraction table may also maintain a many to one relationship with the PhysiologicalDefinition table, with the result that a physiological parameter can have several abstractions performed thereon.

Relative Rule

In one embodiment of the present invention a Relative Rule, or Study, table may be included in the data base. The Relative Rule table may specify a particular alignment of abstractions for a particular study. This table may also contain information about any relative rules that may need to be applied to the abstractions stored in the Temporal Abstraction table. The Relative Rule table may include several fields. For example, a StudyID field may contain an attribute that is a unique identifier for each study. Fields for StudyOwner, StudyName and StudyDescription information may contain attributes that reflect details regarding a research study, such as ownership of the study, and other relevant details pertaining to the study. Fields for EntityRestriction, TARestriction, EventRestriction and TARelativeRestriction may contain attributes that relate to clauses providing higher levels of constraints to the Study table.

Relative Temporal Abstractions

In one embodiment of the present invention a Relative Temporal Abstraction table may be included in the data base. The Relative Temporal Abstraction table may be utilized to store the abstractions that have been realigned relative to a point of interest to the researcher. For example, the researcher may be a person who owns the study. The attributes of the Relative Temporal Abstraction table may be similar to the Temporal Abstraction table, except that the Relative Temporal Abstraction table may contain fields to store values such as RelativeTAStartTime and RelativeTAEndTime values. The RelativeTAStartTime field may store values that are times relative to the start of the period in time that is interesting to the researchers/owners of the study. The RelativeThEndTime field may store values that are times relative to the end of the period in time that is interesting to the researchers/owners of the study. Additional fields may be included in the Relative Temporal Abstraction table, for example, such as a unique StudyID field which may contain an attribute that allows abstractions to be linked with the Study Table with which it shares a many to one relationship. The many to one relationship between the StudyID field and the Study Table may mean that there can be many entries in the TA_RelativeTime table that relate to a particular study.

Rule Base Data

One embodiment of the present invention may include a table in the data base that stores rules. For example, this table may store the Rules created from hypothesis that may be a result of a step in the method of an embodiment of the present invention incorporating the $SDTDM''_0$ framework. Such Rules may be stored in a RuleBase table in the data base. The attributes of the RuleBase table may include several fields, for example, such as EventID, PhysiolocialID and TARuleID fields, each of which may store unique identifications that may be derived from other tables in the database, including the tables discussed herein. Other fields that may be included in a RuleBase table may include the RelativeStartTime and RelativeEndTime fields, that store the data that is described herein. A Value field may also be included in the RuleBase table, to store values that indicates the threshold values that are of interest to researchers.

Data stored in the RuleBase table may be accessed by a user of the present invention. Accessing data in the RuleBase table may cause such data to be deployed to the user in a real time, or virtually real time, environment. Moreover, the Rules stored in the RuleBase may be utilized by the present invention to determine the existence of a particular event or condition onset. For example, a lapse in the breathing of a neonate for greater than 15 seconds and a fall in peripheral oxygen saturation less than 85% for greater than 20 seconds combined with a heart rate of less than 100 BPM, may be recognized, in accordance with data in the RuleBase table, to be an indicator of an apneic event. A skilled reader will recognize that the RuleBase table and the data stored therein may be utilized to aid a user to recognize a variety of events.

A skilled reader will recognize that other tables and/or other data storage means may be available in the present invention. The data of the present invention may be accessible by the present invention by a variety of means and in accordance with a variety of methods. The data of the present invention may be either processed/analyzed or utilized to undertake the functions and other operabilities of the present invention.

Other Possible Functions and Operabilities of the $SDTDM''_0$ Framework

In order for the present invention to be able to perform temporal abstractions on data, the data may first be required to be processed from its raw format by a processing agent. The role of the processing agent may be to initiate the collection of stored physiological and clinical data from external data stores. For example, such external data stores may be stores that support online analysis. Once the data has passed from the external collection phase, the Processing Agent may convert the data to the required format, if such conversion is necessary. The data may be also be structured and stored in the clinical data and physiological data tables. Once storage of the data is completed, the Temporal Agent may begin to process data in order to create the temporal abstractions. The Temporal Agent may utilize rules defined in the temporal rules table to undertake such processing of the data.

Limitations in the known prior art cause it to be unable to be operable to achieve the results of the Temporal Agent of the present invention. For example, one limitation of known prior art is that it is structured to support only one Temporal Rule table. Another limitation of the prior art is that there is generally a lack of clarity regarding how the Temporal Abstractions will be kept consistent across the multi-dimensional distributed locations.

Figure 16:
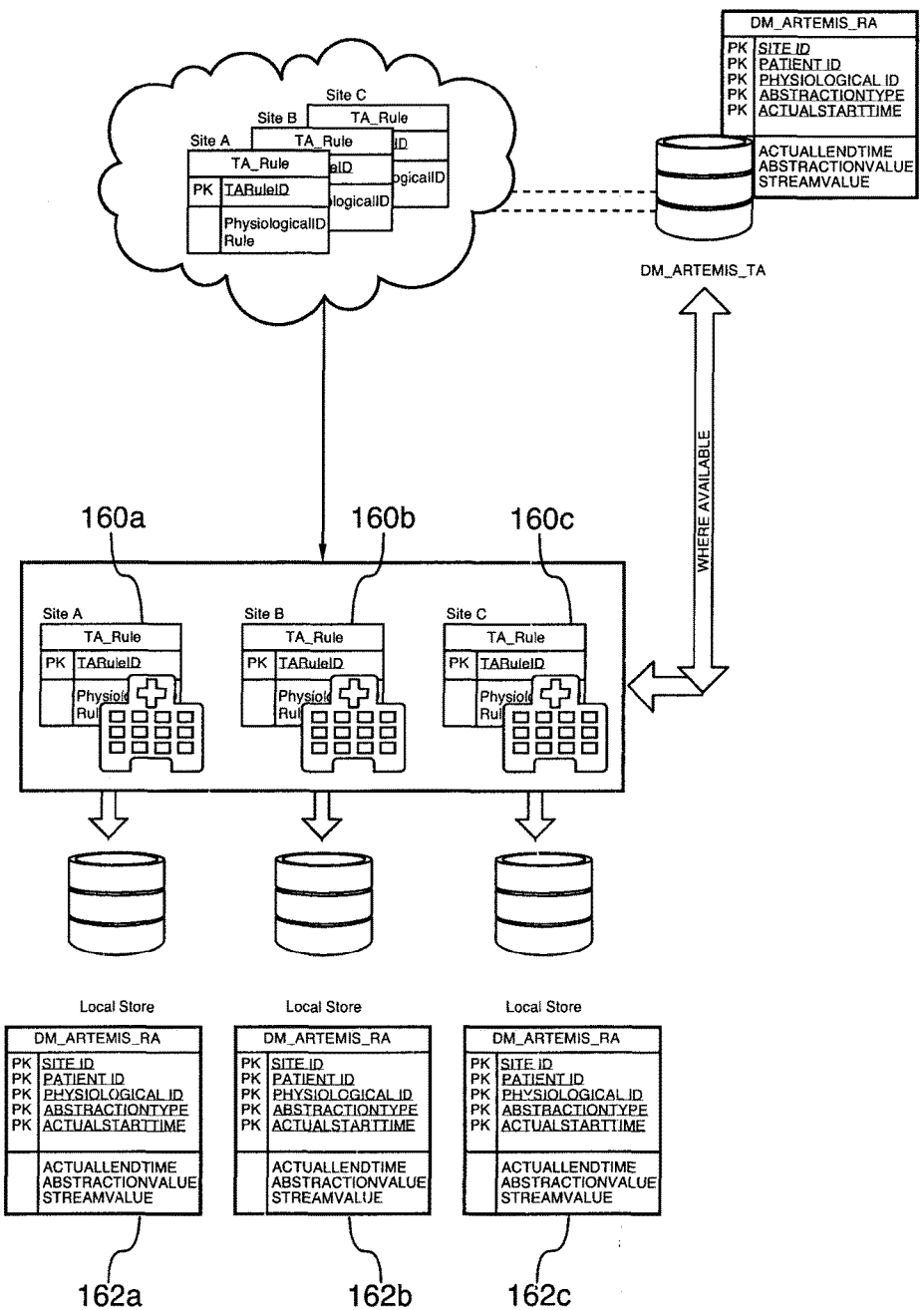
FIG. 16 shows a distribution of temporal rules across multi-dimensional distributed locations that may be included in an embodiment of the present invention.

As shown in FIG. 16, the present invention may offer a solution to these limitations of the prior art. The present invention may be operable to manage multiple Temporal Rule tables 160a, 160b, 160c, and to simultaneously keep the Temporal Abstractions consistent across multiple the distributed sites. Due to current health care policies and improved patient privacy concerns, it may be a requirement that certain types of data exist locally at each site. Thus the Temporal Abstractions 162a, 162b, 162c, may have to be stored locally at each distributed site.

The Temporal Rules may not be required to be stored locally at each distributed site because they may not contain any patient identifying information. For this reason Temporal Rules may be de-centralized to allow for consistency, better control over the security and better accessibility. The present invention may involve a structure which supports the distribution of Temporal Rules and at the same time provides a solution for the Distribution of Temporal Abstractions, where temporal abstractions are allowed to be distributed.

Policies regarding the handling of data and the privacy of data may differ across the multi-dimensional distributed sites. For this reason, there may be a need to support the data in a distributed setting in embodiments of the present invention. In one embodiment of the present invention the distribution of Temporal Rules may involve the following steps: (i) The Temporal Rules may be distributed so that they are stored centrally. When TA's need to be run, the associated rules may be deployed simultaneously for each participating site (Site A, Site B, Site C . . . Site N, etc.). The TA rules deployed for each site may also contain a query, for example, such as a SQL query. The query may be required to be run in order to perform the abstraction at each site. The query may involve, and may be run in accordance with, particular data, for example, such as data stored in a TA_Rule table. (ii) Once one or more of the Temporal Abstractions are deployed each temporal abstraction may be run locally at each site. A temporal abstraction may involve specific parameters, for example, such as parameters provided by the Temporal Rules; (iii) A unique identifier may be attached to the output that is a result of step (ii). As an example, the unique identifier may be stored in a field, such as a SITE_ID field, which may store the unique identifier as a tag that provides each location with a unique ID. The unique identification may be utilized to locate related data, and may be utilized to facilitate a comparison of results across sites if such a comparison is required; and (iv) The results of the Temporal Abstractions may be stored locally at each site, for example, such as in data tables (e.g., an example of a table used for such storage may be a DM_ARTEMIS_TA table). In embodiments of the present invention the results of the Temporal Abstractions may be also stored at a central data storage area for example, such as a central data base table that may be a DM_ARTEMIS_TA table.

The data storage for Relative Rules, for example, such as a Relative Rule table, may specify a particular alignment of abstractions for a particular research study. The Relative Rules data storage may also contain information about any relative rules that may need to be applied to the abstractions, such as may need to be applied to abstractions that are stored in a data storage area, for example, such as the Temporal Abstraction table.

The present invention may provide a benefit over the known prior art. Most prior art frameworks are configured to support only one Relative Rule table and are therefore not suited for multi-dimensional distributed studies. The present invention may support multiple Relative Rule data storage areas, such as Relative Rule tables, and for this reason the present invention may be utilized to process/analyze data of multi-dimensional distributed research studies.

Figure 17:
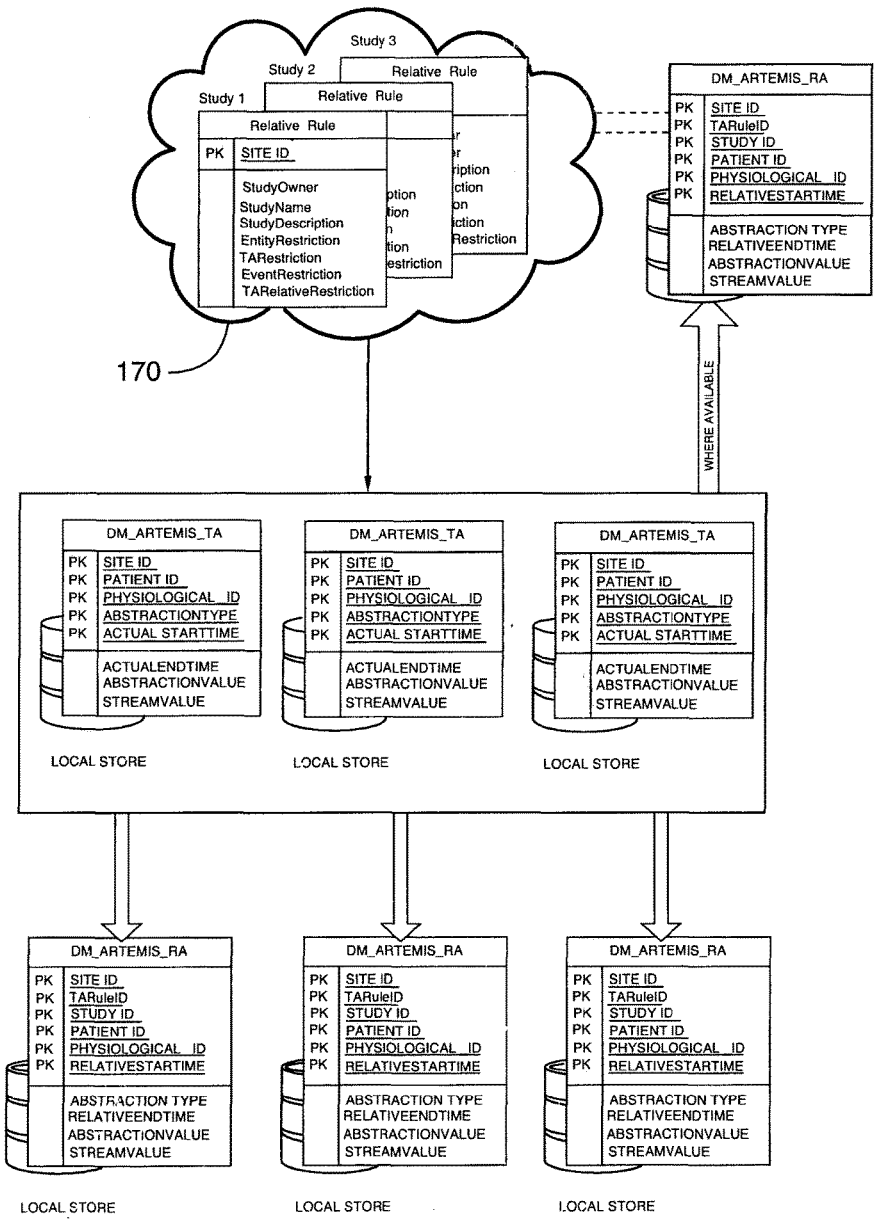
FIG. 17 shows an example of a structure supporting the distribution of Relative Rules that may be included in a possible embodiment of the present invention.

As shown in FIG. 17, the present invention may incorporate a structure supporting the distribution of Relative Rules 170. In one embodiment of the present invention the following three step approach may be taken to enable the distribution of Relative Rules: (i) Relative rules for each study may be deployed or otherwise accessed from a central data storage area. A separate research study table may exist for each participating facility and these separate study tables may each be assigned a unique StudyID; (ii) once deployed or otherwise accessed, the Temporal Abstractions data storage area, for example, such as a Temporal Abstractions table, that may exist at each site may be accessed locally in order to perform the Relative Alignments that may be required for a particular research study; (iii) the re-aligned Temporal Abstractions may be created and stored locally in a data storage area, for example, such as Relative Temporal Data tables, such data storage area may be specific to a research study and a site, the site may be identified by a unique identifier, such as is contained in a table and field of a data base, for example the table/field combination SITE_ID (DM_ARTEMIS_RA). In embodiments of the present invention the Relative Temporal Data may also be stored at the central data storage area, for example in a field in a data base table such as the DM_ARTEMIS_RA field. The storage of the Relative Temporal Data may also include site identification, for example, such as a SITE_ID tag. The site identification data may be utilized to separate and/or compare data between sites.

The Rules Generating Agent of the present invention may utilize findings made by the Functional Agent to allow for the creation of rules that can be defined in the rules database. Hypotheses created via the exploratory data mining phase may be used by the rules generating agent to create rules that can be stored and utilized by an event stream processor in the application of abstractions on real-time data streams. The distributed Rule Base data may exist centrally and may be accessed every time a rule needs to be applied for real-time, or virtually real-time, monitoring. For example, in one embodiment of the present invention the Functional Agent may invoke the Relative Temporal Abstractions stored locally at each site (DM_ARTEMIS_RA). The Rules Generating Agent may utilize results produced by the Functional Agent to create Rule Base Data, which may be stored in the central data storage area. Rules may be accessed and utilized for active real-time, or virtual real-time, monitoring of data, for example, such as patient data.

Figure 21:
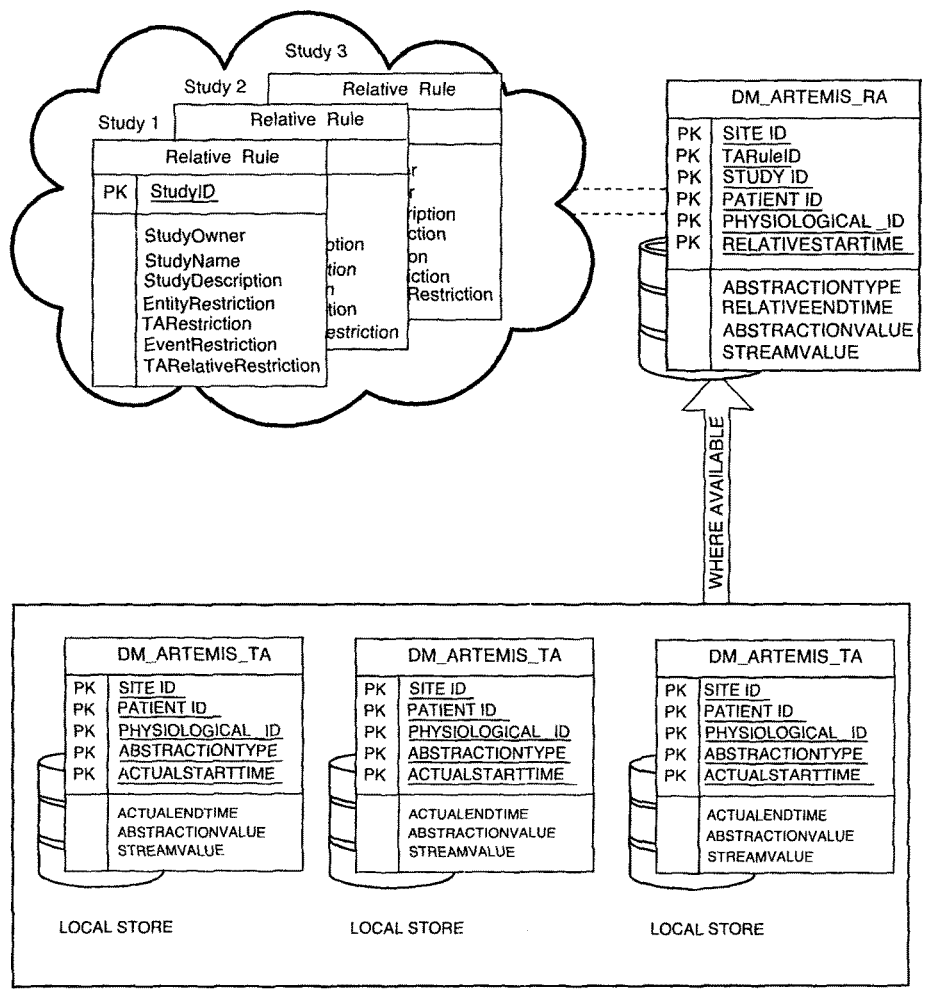
FIG. 21 shows an embodiment of the SDTDM$''_0$ framework of the present invention designed to distribute the Temporal Rules, Relative Rules and Rule Base Data to store the Temporal Abstractions and Relative Temporal Abstractions in a cloud environment.

As shown in FIG. 21, it may be possible for an embodiment of the $SDTDM^n_0$ framework to distribute the Temporal Rules, Relative Rules and Rule Base Data. The $SDTDM^n_0$ framework may further involve storing the Temporal Abstractions and Relative Temporal Abstractions locally to each site, in a cloud environment 210, or in a combination of locally and in a cloud. Storage of Temporal Abstractions and Relative Temporal Abstractions locally to each site may address health care policies and improved patient privacy concerns. However, the creation of regionalized cloud environments may provide a means of distributing the Temporal and Relative Temporal Abstractions. For example, each region, province, state or country may provide one dedicated cloud environment where abstractions may be stored in accordance with privacy policies governing the particular jurisdiction. The dedicated cloud environment may also allow for cross site comparison of results in multicenter studies in order to identify whether particular trends or patterns occur globally or occur solely at particular facilities.

Overview of the Characteristic Multi-Dimensional Framework ($STDM^{n+p}_0$)

The present invention may be a $STDM^n_0$ framework that further incorporates a patient characteristic multi-dimensional ($STDM^{n+p}_0$) framework. The $STDM^{n+p}_0$ framework of the present invention may be defined for clinical research to enable patient specific pre-diagnosing at the onset of illness conditions based on trends and patterns discovered. A skilled reader will recognize that the $STDM^{n+p}_0$ framework may have other operabilities and applications.

Figure 22:
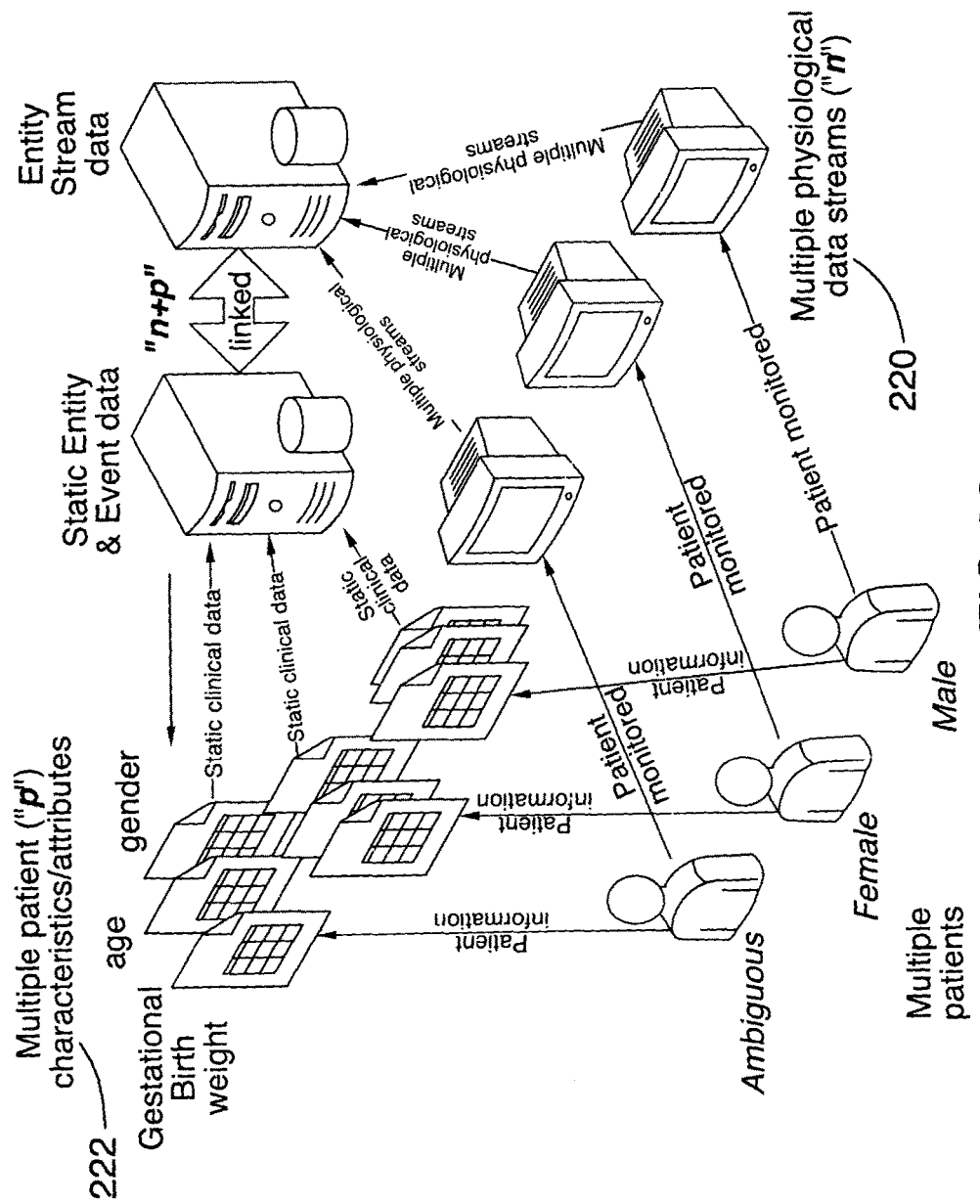
FIG. 22 shows an example of the STDM$''^{+p}_0$ patient characteristic multi-dimensional framework that utilizes patient attributes and may be incorporated in a possible embodiment of the present invention.

The $STDM^{n+p0}$ framework of the present invention may involve the use of patient attributes. As shown in FIG. 22, an embodiment of the present invention may utilize patient characteristic attributes 222 and physiological data 220. The patient characteristics and physiological data utilized by the present invention may be derived from multiple patients.

The $STDM^{n+p}_0$ framework may be operable to assist in the production of a diagnosis based on individual patient characteristic attributes. The $STDM^{n+p}_0$ framework may define a structured methodology that adds patient attributes ("+p") to multiple streams of physiological data collected ("n"). The addition of patient attributes to physiological data may facilitate an individual patient characteristic analysis. The result is that, while prior art system may produce an undefined patient 'one size fits all' approach no diagnosis, the present invention may provide a diagnosis based on defined patient attributes, so that the diagnosis is not general in nature, applicable to multiple persons, but is defined and targeted to a specific patient.

The $STDM^{n+p}_0$ framework may further involve a structured method for creating sub-groupings of the physiological behaviours and also of temporal abstraction behaviours.

The discussion in this section will reference examples from neonatal and NICU applications of the present invention specifically. These references are provided as examples for the purpose of clarifying the nature of the invention. A skilled reader will recognize that the present invention may be applied to other applications as well.

In the $STDM^{n+p}_0$ framework, temporal abstractions may be processed by the relative agent, in a manner discussed herein, and the temporal abstractions may then be transferred to the functional agent. The functional agent may facilitate rule set generation through one or more of the following activities: exploratory data mining; selecting significant rule sets; null hypothesis formulation; and running statistical processes to test the null hypothesis during confirmatory data mining. Null hypothesis testing may be represented by "0" in the $STDM^{n+p}_0$ framework.

The present invention may utilize defined patient characteristic rules and such rules may be applied to a variety of data mining studies. For example, such data mining studies may be conducted to consider a variety of patient characteristics, for example, such as gender and gestational age. These patient characteristics may be considered in the analysis and processing of multiple physiological data streams. The defined patient characteristic rules may include baseline acceptable thresholds and the processing of the multiple physiological data streams by the present invention may involve comparing the data to the baseline acceptable thresholds. This comparison may determine trends and patterns in research study data, or across data sets or streams. The trends or patterns may indicate specific events of significance to a user that may be utilized to assist in a diagnosis of a condition. In particular, the present invention may provide further insight into accurately diagnosing individual preterm infants.

The $STDM^{n+p}_0$ framework may further undertake a step to sub-group or cluster data. For example, the present invention may undertake the following steps to achieve sub-grouping and/or clustering of data relating to preterm infants and neonates. The patient characteristic attributes considered and defined within this example are that of gender and gestational age. These attributes may be chosen due to the significance of these attributes to certain questions being addressed by one or more particular research studies. In this example, the present invention may undertake to process and analyze static clinical data that is linked with the physiological HR data of male preterm infants at 35 weeks gestation age. The present invention may further undertake to process and analyze static clinical data that is linked with the physiological HR data of male neonates at 28 weeks GA. The processed data could be compared with similar data collected, processed and analyzed relating to female infants at 35 weeks GA, and at 28 weeks GA. The processing/analysis of the data and the comparison of the data may provide results that offer insight into conditions affecting the particular infants involved in the study and/or the groups of infants involved in the study. In particular, data may provide results that offer specific information relating to the sub-group; of patients involved in the study.

Figure 23:
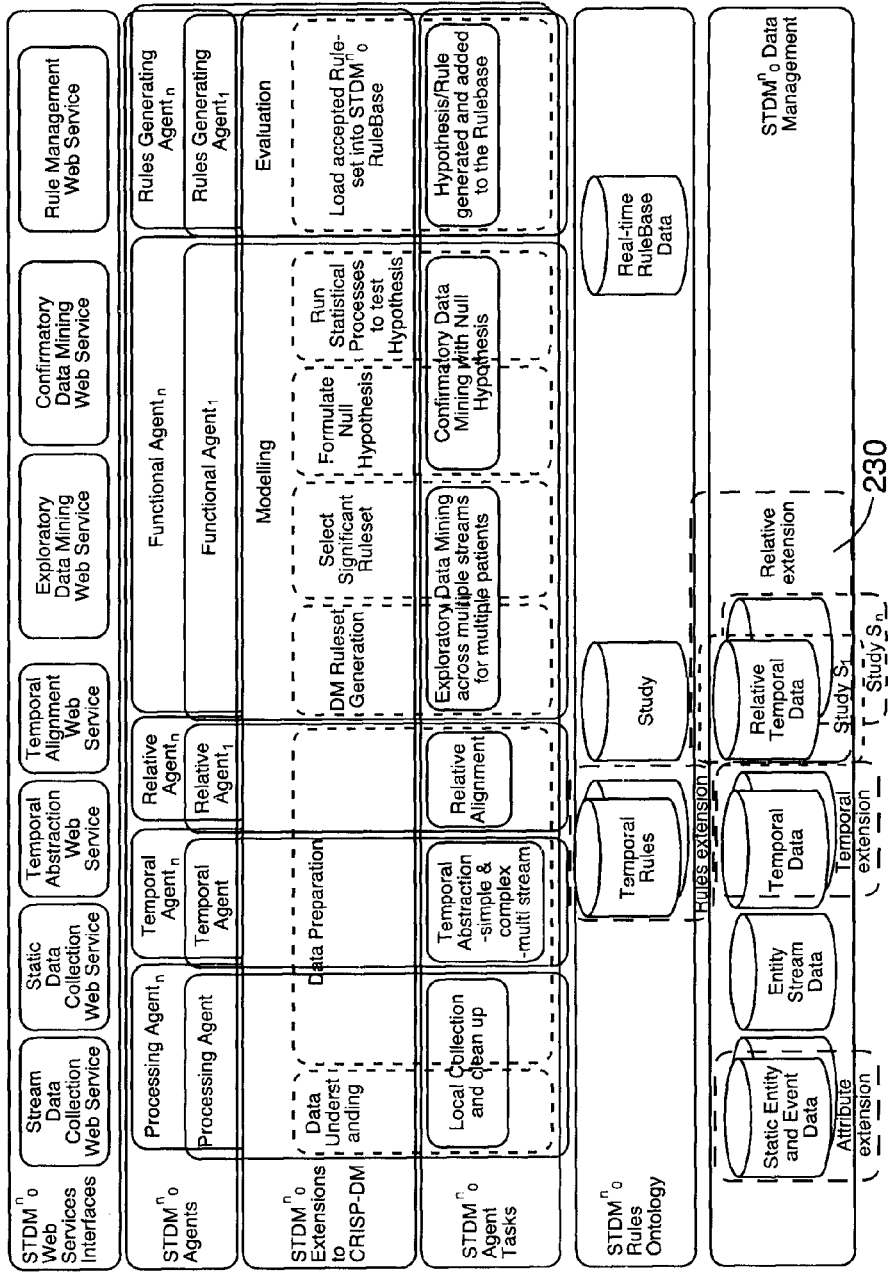
FIG. 23 shows areas of the STDM$''_0$ framework that may be extended to form the STDM$''^{+p}_0$ framework as an embodiment of the present invention.

In one embodiment of the present invention, the $STDM^{n+p}{}_O$ framework may be operable to analyze multiple streams of data from multiple patients with asynchronistic, static, patient-centric data. In this manner, the present invention may be multi-dimensional. An embodiment of the present invention may be understood to provide an extension or add-on to the functions of the $STDM^n{}_O$ framework. Some areas of the $STDM^n{}_O$ framework that may be extended to form the $STDM^{n+p}{}_O$ framework, such as relative extension 230, are shown in FIG. 23. A skilled reader will recognize that the present invention may also be viewed as the $STDM^n{}_O$ framework being incorporated with, or otherwise integrated with, the $STDM^n{}_O$ framework.

The $STDM^{n+p}{}_O$ framework of the present invention may involve the Static Entity and Event database interacting through the use of extended patient attribute data. This may also have an impact on other databases within the $STDM^{n+p}{}_O$ framework. There are many different examples of patient-centric data available from an electronic health record and/or clinical information system (CIS), including attributes such as: gender, gestational age, birth weight, birth length and birth head circumference. A skilled reader will recognize the various embodiments of the present invention that may exist to address particular data in a particular manner as part of the $STDM^{n+p}{}_O$ framework.

In one embodiment of the present invention, patient attributes may be stored in a stored data area, for example, such as a Patient attribute table in a data base. In one embodiment of the present invention that may be utilized in an NICU environment, gestational age and gender may be utilized as patient attributes. These attributes, or other attributes, may be chosen as representing attributes that may impact results from clinical algorithms (or other calculations) due to the relationship of these attributes with patient maturity. A skilled reader will recognize that other attributes may be utilized in other embodiments of the present invention for other reasons.

Several extended tasks may be completed within the layers of the multi-agent systems utilized by the $STDM^{n+p}{}_O$ framework. For example, in one embodiment of the present invention, the $STDM^{n+p}{}_O$ framework applicable to physiological data stream, the framework may be operable to support a characteristic multi-dimensional data mining framework that may be defined for clinical research. This framework may utilize patient attributes in the process of data mining patient physiological data streams.

Figure 24:
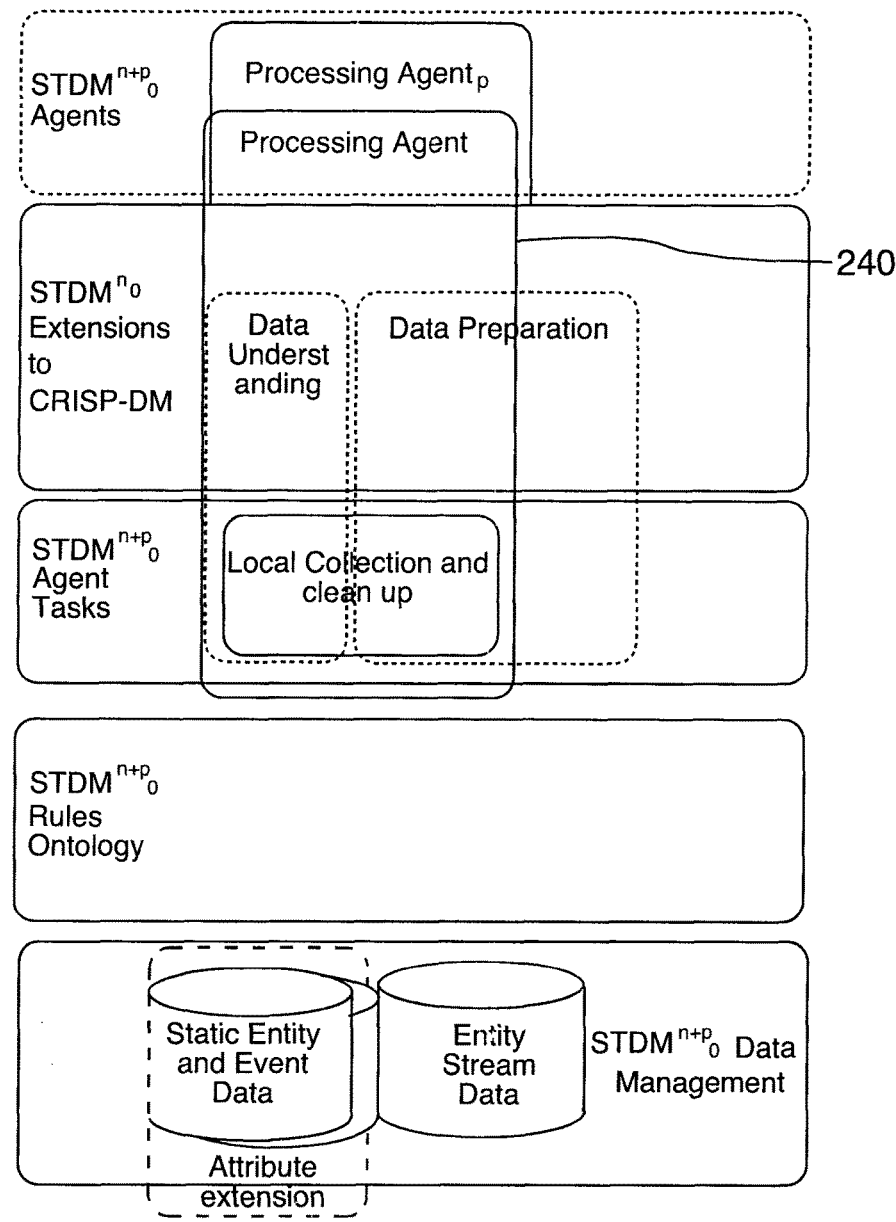
FIG. 24 shows an example of the layers and tasks performed within the Processing Agent that may be included in an embodiment of the present invention.

Within the $STDM^{n+p}{}_O$ framework a Processing Agent may perform the task of attaining and preparing physiological streamed data. The physiological streamed data may be obtained from, and otherwise transferred to the present invention, from sensors, or may be retrieved from static data sources. Some of the data may be provided in the form of data tables from databases, such as clinical and physiological databases. As shown in FIG. 24, multiple layers and multiple tasks may be performed within the Processing Agent 240.

A step of the method of the present invention, may involve the processing and integration of synchronistic collected physiological stream data with asynchronistic, static clinical data. For example, such integration may occur within the context of the neonatal intensive care environment. In this example, stream data may represent either or both of the following types of data: (i) physiological stream data collected from medical monitoring devices such as RR, $SpO_2$ and HR; and (ii) asynchronistic, static or slow moving data may represent clinical information such as patient ID, date of birth, gender, and gestational age. The present invention may be able to accept and process ambiguous characteristics as well. For example, in the NICU environment in some rare cases there may be a non or 'ambiguous' gender applied to a neonatal subject, such as a neonate born within the range of 23-27 weeks. This subject may later develop into either a male or a female subject.

Figure 25:
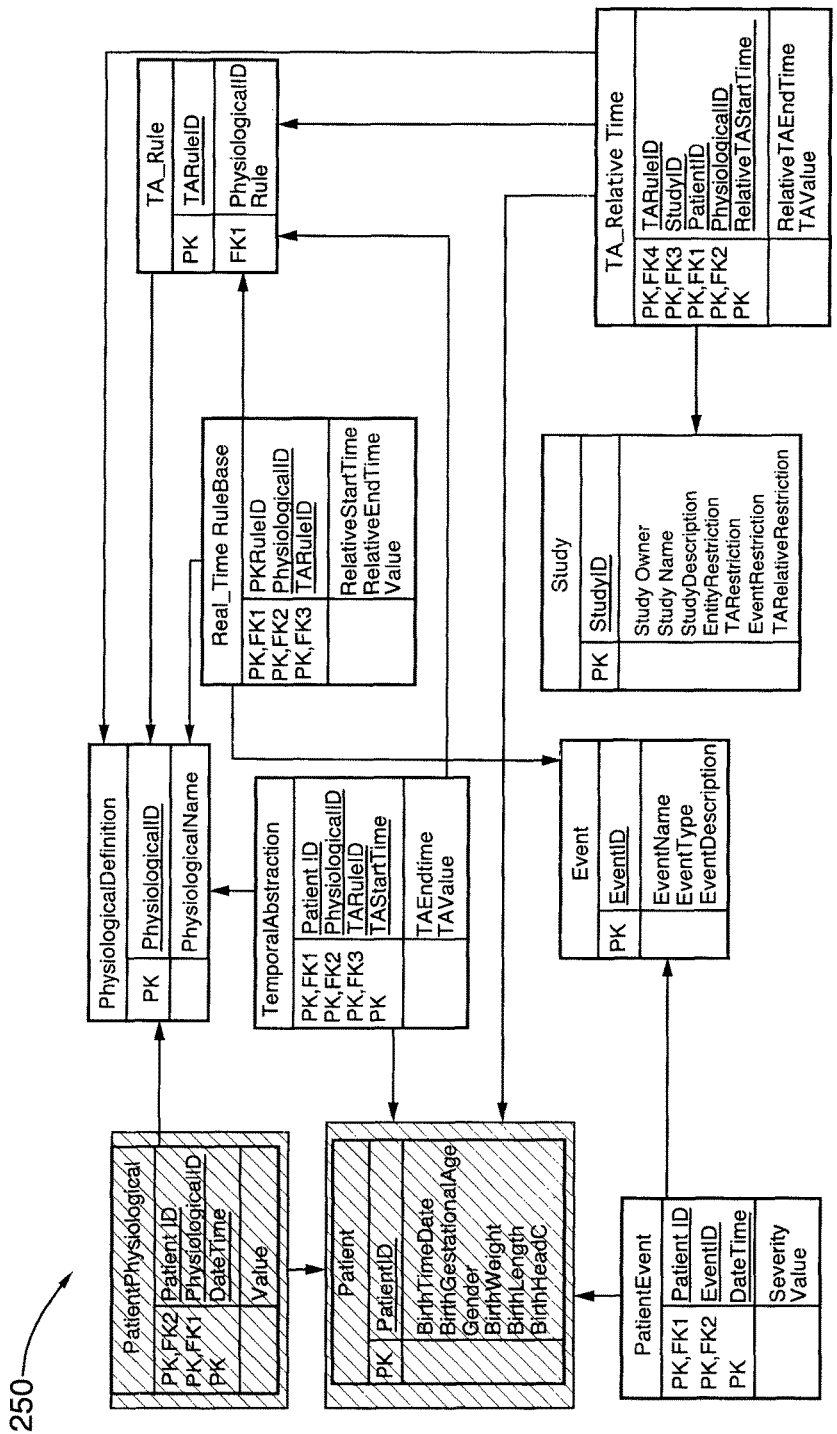
FIG. 25 shows an example of static clinical data of the STDM$''^{+p}_0$ framework that may be included in an embodiment of the present invention.

FIG. 25 shows an example of possible static clinical data table structure 250 that may be utilized by an embodiment of the $STDM^n{}_O$ framework and these may represent particular tables of interest. For example, the Patient table may contain attributes of interest for $STDM^{n+p}{}_O$ research, such as attributes relating to gender and/or gestational age at birth (BirthGestationalAge). A table may be created for the synchronistic collected physiological stream data. A table may also be generated to incorporate new attributes. The structure of the tables may be designed to improve results when running temporal abstraction queries in the temporal agent.

The tables of the $STDM^n{}_O$ framework may be generally stored in a clinical knowledge database. In embodiments of the present invention, the tables may be accessed in the database and the data therein, or the tables themselves, may be further refined at a future point in time. For example, such refinement may involve the creation of clinical knowledge from the data. The data may be first investigated by exploratory data mining and subsequently by confirmatory data mining. The table structure of the $STDM^n{}_O$ framework may be that of a relational database. However, a skilled reader sill recognize that other table structures, or data storage configurations and means may be utilized in the present invention. Moreover, the table structures or data storage configurations/means utilized in the present invention may be in real-time or virtually real-time, such as such as, a real-time database structure. Incorporating real-time capable data structures and storage configurations/means may provide clinical advantages for the present invention over the prior art, as the data may be immediately available for processing, access and other uses by professionals. This may allow a professional to have information almost literally at their fingertips for immediate access and therefore the data and its results may be immediately be applicable to a particular scenario or situation where such data is required, for example, such as for application of such data to produce a clinical decision that may be a health diagnosis or treatment decision. A skilled reader will recognize the benefits that may be derived in the present invention over the prior art in many field of use by real-time data table structures or data storage configuration/means.

In an embodiment of the present invention interaction may occur within the Temporal Agent between the Static Entity and Event Database, with the Entity Stream database. For example, such interaction may occur when a temporal abstraction is created in the Static Entity and Event Database. Discoveries may be made based upon the temporal abstractions, and such discoveries may help drive and influence the temporal rules that are created. The Temporal Agent of the $STDM^{n+p}{}_0$ framework may be operable to undertake a method that may allow the patient characteristic framework to include methods for applying temporal abstraction (TA) across multiple parameters for multiple patients to enable mining of patient characteristic multi-dimensional temporal data. In this manner the present invention may offer a benefit over the prior art which is generally unable to undertake such a method, and is therefore generally unable to apply temporal abstractions across multiple parameters for multiple patients to enable mining of patient characteristic multi-dimensional temporal data.

In embodiments of the present invention, the Temporal Agent may be designed to create new temporal encoded data streams. For example, the Temporal Agent may be designed to create a new temporal encoded data stream by abstracting behaviours or trends that represent anomalies within that defined stream. The abstraction of behaviours or trends may occur at time stamped intervals. The anomalies may be defined either as a trend such as increasing/decreasing, or as level shifts such as low/normal/high. An example of an anomaly may be an ECG physiological data stream. All thresholds may be dependent on the source of the data stream collection. For example, if a data stream is generated for a particular infant, then the thresholds may be dependent upon the gender and gestational age of the infant.

As an example, if an anomaly is the ECG physiological data stream, each reading or data point from the ECG stream has the potential to be included in several abstractions. For example, this data point could have been collected while the heart rate was 'increasing' but was still within limits recognized to the be "normal" limits. Complex abstraction may involve the comparison of abstracted parameters performed across multiple streams. Each abstraction performed may be stored in a table form within the temporal database.

Tables may be generated for multiple data types, for example, such as temporal abstractions, new attributes, and temporal rules. The tables may be interconnected or linked in a variety of manners. For example, the temporal rules table may incorporate new attributes, or there may be a link between the new attributes and the temporal rules tables.

Interaction may occur within the Relative Agent between the Temporal Database and the Relative Temporal. For example, such interaction may be driven by a research study of interest. Within the Relative Agent it may be possible that studies performed on temporal abstractions be based on clinical information from individual patients, such as gender and gestational age. A skilled reader will recognize that there may be a variety of interactions between tables and data that may occur within the framework of the present invention, and that such interactions may be based on different factors or considerations. The factors or considerations may be related to the type of data and data streams that are utilized by the present invention. The examples of NICU health related data streams presented herein are therefore just one example of data streams that may be utilized by the present invention and therefore, the possible factors or considerations related to such NICU data streams are merely one example of possible factors or considerations that may be integrated in to the present invention. Other data streams, and other areas of data, such as business data, recreational data, or any other type of data that the present invention may be utilized with, may cause other factors or considerations to be incorporated into the present invention.

As another example of linked data, in an embodiment of the present invention, a TA_RelativeTime table may be created and this table may incorporate or link to new attributes.

The framework of the present invention may be constructed to cause a real-time event stream processor analysing the current condition of babies in a NICU to utilize hypotheses generated by the patient characteristic framework.

Within the Functional Agent the realigned temporal abstractions created in the Relative Agent may be further processed. The functional agent may cause extended CRISP-TDM modeling tasks to occur. Such modeling tasks may include any or all of the following steps: rule set generation through exploratory data mining; selecting significant rule sets, null hypothesis formulation; and running statistical processes to test the null hypothesis during confirmatory data mining. The present invention may generally include a data understanding phase, and defining TA abstraction, which may be performed through further extending patient centric attributes within algorithms by gender and gestational age.

A possible end result of the present invention may be a new gender and gestational age defined clinical algorithm for the early prediction of disease based on retrospective clinical data. Such retrospective clinical data may be collected within the Processing Agent and stored in the Static Entity and Event database. The Rules Generating Agent may utilize the clinical algorithms developed in the Functional Agent to provide patient context-specific intelligent monitoring and alerting on real-time patient data streams. Co-mining, may integrate data mining results with expert knowledge. The present invention may further incorporate additional input that may be received in the form of clinician-defined rules.

Figure 26:
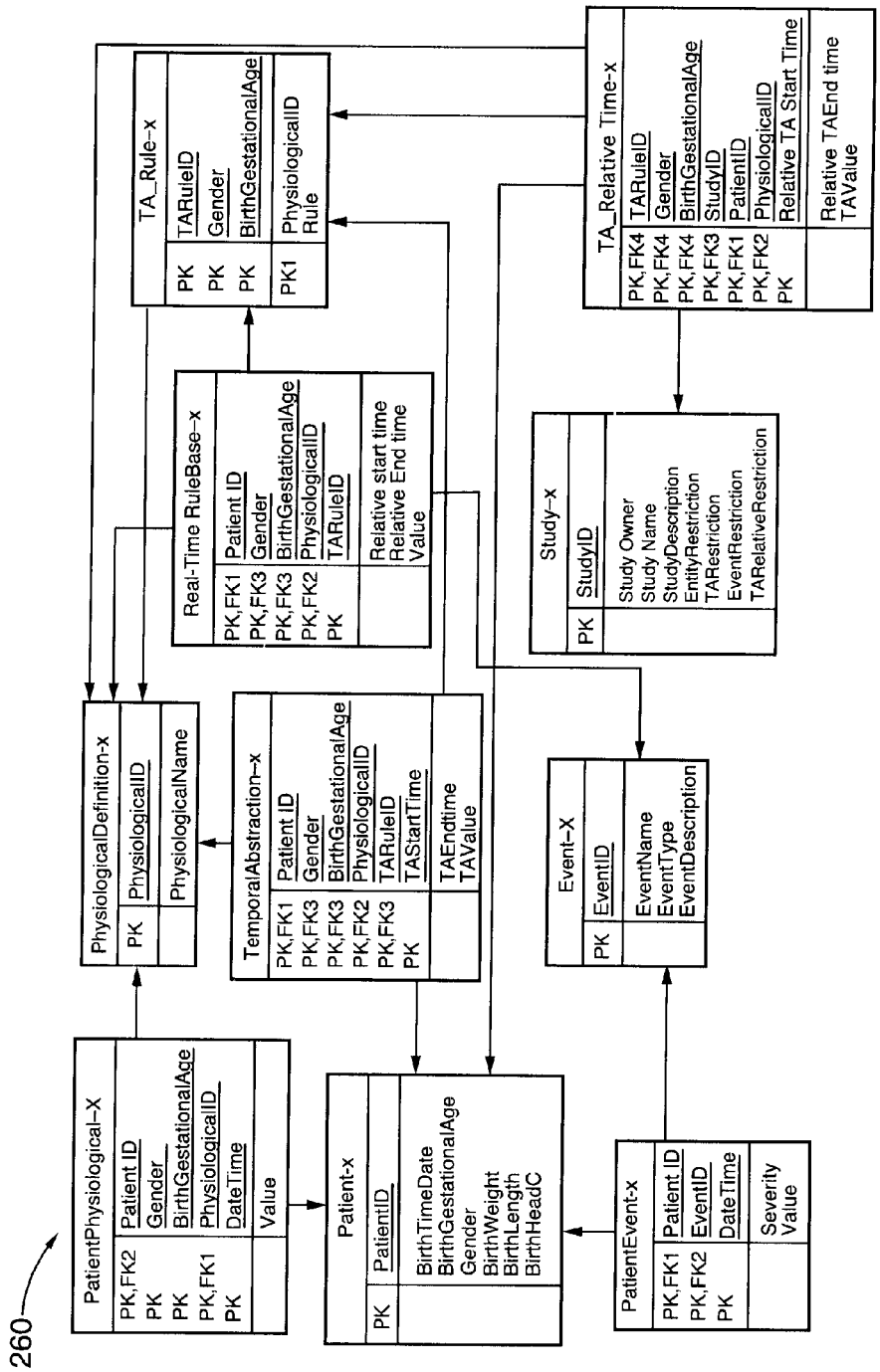
FIG. 26 shows an example of a tables structure of the STDM$''^{+p}_0$ framework that may be included in an embodiment of the present invention.

A skilled reader will recognize that $STDM^{n+p}{}_0$ data storage may be structured in a variety of manners. For example, the $STDM^{n+p}{}_0$ data storage may incorporate interactive tables 260 that are operable to achieve efficient data storage, as shown in FIG. 26. A skilled reader will recognize that the present invention may incorporate other data storage means and structures.

The present invention may be operable to accept extensions to the data storage means and structures it incorporates. For example, extensions made to the PatientPhysiological-x, TemporalAbstraction-x, TA_Rule-x and TA_RelativeTime-x tables from the $STDM^n{}_0$ framework are discussed in detail herein, as may be achieved within their respective corresponding agents.

Figure 27:
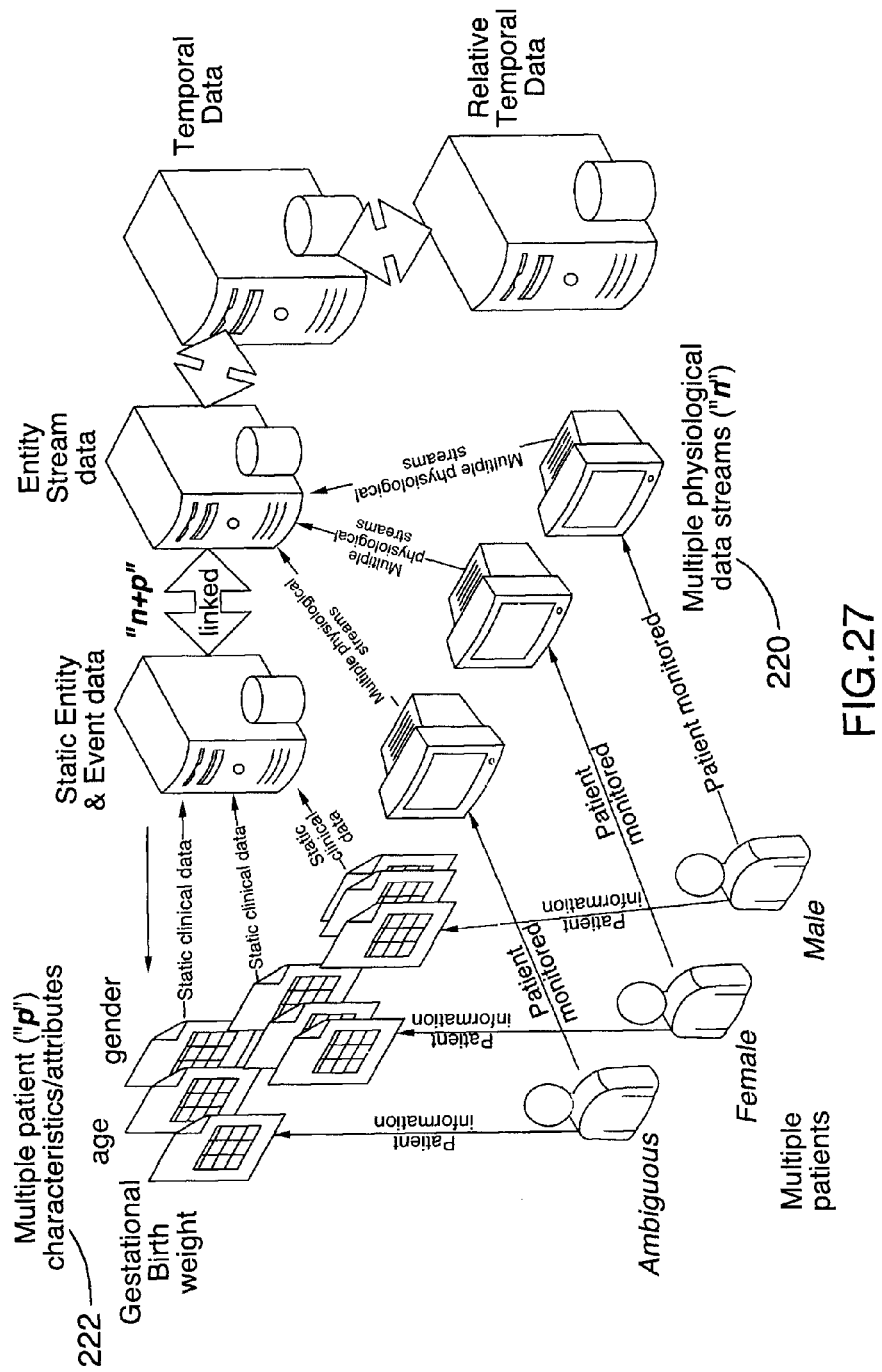
FIG. 27 shows an example of data collection and flow of the STDM$''^{+p}_0$ framework that may be included in an embodiment of the present invention.

The $STDM^{n+p}{}_0$ framework data collection and flow may be in accordance with a variety of the types and manners. An example of one such data collection and flow is shown in FIG. 27, wherein data flows from one or more patients 270 to an Entity Stream data collection means 272 that is linked to a Static Entity and Event Data data storage means 274.

In general, the present invention may incorporate a $STDM^{n+p}{}_0$ framework data collection and flow wherein within the Processing Agent multiple streams of physiological data may be collected within the Entity Stream database. Entity Stream database may be linked to the Static Entity and Event database through the utilization of linking patient attributes such as gender and gestational age. This may provide a structured format supporting a temporal agent wherein temporal abstraction queries may be run once a research study of interest has been defined. In turn, this defined structured format may realign these abstractions within the relative agent at a point of interest relevant to the study defined. In terms of workflow ordering, data may be processed through techniques defined in the Functional Agent. For example, the data may be fed through a data mining system using the clinical algorithms developed in the Functional Agent. In the event that this process indicates the potential early onset of a condition of interest, the intelligent patient monitoring system may indicate this knowledge and the results that are evaluated. The knowledge gained of pattern detection in physiological data may then be encoded. For example, the physiological data may be encoded to meet HL7 and SNOMED-CT standards. The encoded data may be and stored, for example, such as storage as part of the gold standard accepted within clinical databases. A skilled reader will recognize the variety of standards that may be met by the present invention, and that these standards may vary in accordance with the application of the present invention and the type of data streams that are incorporated in the present invention.

One embodiment of the present invention may be a patient characteristic multi-dimensional adaptation to the $STDM''_0$ framework to enabling sub-classifications created by $STDM''^{+p}_0$ framework. One or more of a CRISP-DM model, or a CRISP-TDM, may be incorporated into the framework, and simultaneously a more patient centered approach may be utilized.

A skilled reader will recognize that the present invention may have a variety of embodiments and applications. In the healthcare domain, and in particular in healthcare research, there may be an inherit ongoing limitation restricted by the lack of availability of data to be analysed as 'secondary use' data for the purpose of developing clinically relevant algorithms for use in this domain (Clarke, 2003). As the electron c healthcare domain evolves, so too data mining software developers use to produce well designed analysis tool to pursue knowledge discovery in real-time physiological date streams are required to evolve. With the interest in healthcare domain increasing, aid as issues related to receiving approval of use of data for secondary analysis of health data are resolved, there is a need for the cost and effort barriers to data mining projects to decrease. The $STDM''_0$ framework, as proven by the adoption of the Artemis project described herein, may provide an architecture operable to capture aspects from collection to application of rules in real-time, including newly adopted rules In an embodiment of the present invention, newly defined Patient Characteristic rules may be stored within a single physical database, or other storage means. However, as these findings become more defined and adopted as clinical rules multi-centre studies and multi-centre implementation may occur and the present invention may apply a distributed functionality option to meet such an implementation.

The ability of the present invention to expand to growing needs of data mining in a sector, such as health care, is another benefit of the present invention over the prior art. The present invention offers exploratory data mining to further refine and define patient characteristic rules and this assists in achieving improved care of infants being monitored.

The present invention may be operable not only to explore data collected from medical devices but also to enhance their usefulness in serving the purpose of storing data collected to assist in the improving the provision of better patient care. Every human by nature is created to have genetic differences. Such genetic differences result in each patient having distinct characteristics that start from conception and continue throughout life. When caring for patients, for example, such as critically ill preterm infants, it may be helpful to incorporate individual characteristic in the data gathered that will be utilized as a basis for patient diagnosis and treatment decisions. For example, the Incorporation of attribute data may assist in creating a shift towards individualized treatments of care when considering developing clinical rules that will be adopted by clinical decision support systems or CDSs.

The $STDM''^{+p}_0$ framework of the present invention may enable multi-dimensional data mining to detect patterns of a data subject characteristic. For example, in the NICU context, the present invention may detect patient characteristic predictive temperament. The $STDM''^{+p}_0$ framework may provide a structure that is applicable to the development of patient oriented trends to be captured, analyzed and finding(s) extracted and embedded into algorithms designed to assist in the recognition of predictive trends. For example, such as predictive trends recognizable at the early onset of conditions such as nosocomial infection ("NI").

The present invention may have various embodiments and applications. Some specific examples of embodiments of the present invention are provided herein to offer clarity to the potential aspects and applications of the present invention. These examples are provided merely as possible embodiments of the present invention and a skilled reader will recognize that the scope of the present invention may include other embodiments of the present invention.

EXAMPLES

I. $STDM''_0$ Example: Critical Care

The present invention may be implemented as a clinical monitoring and data mining environment for determining patterns related to diagnoses and, optionally, predicting future diagnoses. A solution manager service 80 for enabling clinicians to carry out the methods may be incorporated in the present invention, as shown in FIG. 3. Within the critical care context, clinical data and physiological data may be used together with temporal rules to create temporal data summary streams of the raw physiological data streams. Physiological data streams may be supplemented by clinical data. These summary streams can represent summaries based on the cross correlation of multiple raw streams.

Users can easily generate individual study based relative temporal data tables in a flexible multi-dimensional environment during the data preparation step that encodes the time series time stamps relative to the $t_0$ point of interest. For example, $t_0$ may refer to an alignment of neonatal patient streams for a set of neonatal patients based on the time that a certain condition was diagnosed for each patient thereby enabling alignment of preceding stream behaviours within the continuum of $t_{-1}, t_{-2}, \ldots, t_n$, where n is the distance back in time of interest for a given study.

Users of the environment can create relative rules that represent a range of functions and/or criteria against the patient, event, physiological and temporal data tables.

Processing Agent

The role of the processing agent is to acquire and prepare the stream data from sensors together with static data for storage within the stream data tables and the static data tables respectively. Within the context of critical care the static data would be supplied by the clinical information systems, for example date of birth or gestational age at birth, and the stream data acquired from medical sensor devices, for example, ECG signals, or collected manually repeatedly over time, for example temperature readings taken manually repeatedly over time.

Static data can be supplied via static data web service, which in the context of critical care could be via HL7 message formats, for example. Stream data can be supplied via stream data web services.

Temporal Agent

The role of the temporal agent is to create new temporal encoded streams at a slower frequency than the data stream or streams being encoded, by abstracting the time interval, representing the trend and/or behaviour of the stream during that summarized time interval. Each data stream is temporally abstracted into appropriate abstractions such as trends (increasing, decreasing) and level shifts (high, low) for example based on the temporal rules driving the temporal abstraction contained in the temporal rules table. Each raw piece of data may belong to several abstractions. For example, a particular measurement may be part of an 'increasing' abstraction, and at the same time be within 'normal' limits. Complex abstractions can also be done across multiple abstracted parameters. Each abstraction stream is stored in the temporal data table.

The relative, functional and rules generating agent may be run together as a set for any given study from $study_1$ to $study_n$. It is also possible to run the temporal agent utilising new temporal rules that are required for a particular study. This principle is Illustrated via the example study below.

(a) Clinical Study Example 1: ECG Instability

A clinical researcher may be determining, for example, whether EGG instability is preceded within the past 24 hours by falls in mean blood pressure to less than gestational equivalent age (eg 35 mm Hg for a 35 weeks gestation baby) for more than 20 seconds concurrently with a fall in peripheral oxygen saturation less than 85% for greater than 20 seconds".

In this example, physiological data streams include ECG, blood pressure and peripheral oxygen saturation.

Firstly, the physiological data stream data for ECG, blood pressure and peripheral oxygen saturation is loaded into the stream data tables by the processing agent via the stream data collection web service. Similarly related clinical data is loaded into the static data table via the static data collection web service.

Through use of the temporal agent, a temporal abstraction rule may be created to create a temporally encoded stream to detect ECG instability based on assessing the ECG stream for each patient. Similarly a temporal rule may be created to determine when mean blood pressure falls below a threshold based on the patient's gestational equivalent age for a time interval of greater than 20 seconds. A temporal rule may be created to determine peripheral oxygen saturation less than 85% for greater than 20 seconds. A complex rule could be created representing where they overlap. These rules could be created using the temporal abstraction web service.

The relative agent selects patients that have been detected to have ECG instability and for this example would use the first occurrence of ECG instability to determine a time point of interest. This time point of interest is shown within FIG. 9 as the circle point of Diagnosis. Examples of where the complex temporal abstraction could have occurred are shown as the rectangular blocks over the streams that proceed the diagnosis. As can be seen in the absolute time representation in FIG. 9, the actual time points for the complex abstractions and the diagnosis of interest occur at different points in actual time for each patient.

For each selected patient the time of the ECG instability is used to reset actual times within all three streams of interest to relative times based on the time of interest becoming $t_0$, as shown in the relative time portion of FIG. 9. The example in FIG. 9 shows the similar relative distance of the episodes of the complex abstractions from the point of the diagnosis of interest for this study.

With the data prepared, temporally abstracted and aligned based on a point of interest, the two step data mining can commence. This two step process supports initial rule generation (exploratory data mining) and then testing of a null hypothesis through confirmatory data mining.

In this example, a hypothesis has already been proposed of a suspected correlation between the behaviour of ECG and the preceding behaviour of mean blood pressure and peripheral oxygen saturation. As a result the rule set can thus be immediately defined based on what has been proposed. However, the study could be altered to perform exploratory data mining on other data streams to see whether other temporal abstractions exist that have a high correlation of occurrence before ECG instability resulting in the need to perform exploratory data mining.

For the purposes of this example, one could encode the hypothesis such that a correlation coefficient of 0.8 is used. This hypothesis is thus represented utilizing a correlation coefficient notation of the form:

$$H_1: \rho_{(X,Y)} > 0.8$$

where:
X represents ECG instability and;
Y represents ABPmean<gestational age for 20 seconds; AND $SaO_2$<85% for the same 20 seconds.

The effective null hypothesis is represented as:

$$H_0: \rho_{(X,Y)} = 0.8$$

The true null hypothesis is represented as:

$$H_0: \rho_{(X,Y)} < 0.8$$

During the confirmatory data mining phase, the correlation between ECG instability with preceding ABPmean and $SaO_2$ falls is determined.

If $H_0$ cannot be accepted then the rule represented by $H_1$ above can be accepted and created as a rule within the Rulebase table. For example, the rule would be a complex abstraction based on the correlation of two simple threshold breaches of ABPmean and $SaO_2$ falls with an alert to potential for ECG stability as the rule action. The rule management web service can add, change or delete rules independent of the rules generating process. Rules can exist as production, test or development rules.

(b) Clinical Study Example 2: Mean Blood Pressure

A clinical researcher may be determining, for example, whether a correlation exists between mean blood pressure and gestational equivalent age (eg 35 mm Hg for a 35 weeks gestation baby) for babies not under treatment for diagnoses beyond those usual due to prematurity.

In this example, physiological data streams includes blood pressure.

An existing temporal rule may be utilized to determine when mean blood pressure falls below a threshold based on the patient's gestational equivalent age for a time interval of greater than 20 seconds.

The relative agent may select patients that satisfy the criteria of not being under treatment for diagnoses beyond usual due to prematurity for the duration of their $35^{th}$ gestational equivalent week. For each selected patient the time of the commencement of the $35^{th}$ week of gestational equivalent age may be used to reset actual times within the stream of interest (mean blood pressure) to relative times based on the time of interest becoming $t_0$ and moving forward for 7 days.

In this example, a hypothesis has already been proposed of a suspected correlation between the behaviour of mean blood pressure and the gestational equivalent age. As a result, the rule set can thus be immediately defined based on what has been proposed.

As in the previous example a null hypothesis can be tested during the confirmatory data mining phase.

(c) Clinical Study Example 3: ECG Instability II

A clinical researcher may be determining, for example, whether ECG instability is preceded within the past 24 hours by common behaviours in physiological streams that occur for 1 minute or more.

In this example, physiological data streams include ECG and other physiological streams.

The temporal abstraction rule created previously to detect ECG instability based on assessing the ECG stream for each patient may be used. All temporal stream encodings on streams other than ECG are included in the study.

The relative agent may select patients that have been detected to have ECG instability and for this example use the first occurrence of ECG instability to determine a time point of interest. For each selected patient, the time of the ECG instability may be used to reset actual times within all streams of interest to relative times based on the time of interest becoming $t_0$.

With the data prepared, temporally abstracted and aligned based on a point of interest, the two step data mining can commence. This two step process supports initial rule generation (exploratory data mining) and then testing of a null hypothesis through confirmatory data mining.

In this example, a hypothesis has not already been proposed and hence the exploratory data mining phase is completed for a training set of patients of a suspected correlation between the behaviour of ECG and the preceding behaviour of other streams supplied.

If a correlation is detected on the training set, then that correlation is transformed into a null hypothesis and tested further on test data sets to determine a correlation factor.

If successful, the rule represented by $H_1$ above can be accepted and created as a rule within the rulebase data table.

I. $SDTDM''_0$ Example

The $SDTDM''_0$ framework of the present invention may be utilized to support clinical research in neonatal intensive care. As an example, through an active collaboration between The Hospital of Sick Children, Toronto, led by Dr. Andrew James, The Women and Infants Hospital (WIHRI), Providence, R.I., led by Dr. James Padbury and the Health Informatics Research team, University if Ontario Institute of Technology (UOIT), Oshawa, led by Dr. Carolyn McGregor, current clinical research activities within the NICU have been utilized to demonstrate the operability of the framework to provide analytical support for the clinical research activities. The research conducted at UOIT was part of the clinical research studies that have been ethically approved at both sites as part of the Artemis project, Artemis is a platform for real-time enactment of clinical knowledge as it relates to multi-dimensional data analysis and clinical research. The Artemis framework is a platform for real-time analysis of clinical knowledge as it relates to multi-dimensional data analysis and clinical research.

There is mounting evidence suggesting changes in physiological stream behaviours occur prior to the diagnosis of certain conditions. The Health Informatics Research group at UOIT focuses on research into earlier detection of late onset neonatal sepsis and episodes of apnoea using physiological stream data being collected from three distributed sites. In this research a number of parameters were collected such as: 1) abstractions for heart rate decelerations in an hourly time window; 2) fall in peripheral oxygen saturation less than 85% for greater than 20 seconds; 3) a lapse in breathing of a neonate of 35 weeks gestation for greater than 15 seconds; and 4) a low heart rate and respiratory rate variability in an hourly segment.

Collection of data for this example of the present invention occurred at three main distributed sites. The first site is located at The Hospital for Sick Children, Toronto, Ontario. Multiple streams of physiological data were generated from this location from the Philips IntelliVue MP70 neonatal monitors at the rate of a reading every 1024 milliseconds. These streams included the constant collection of electrocardiogram derived heart rate (ECG-HR), transcutaneous oxygen saturation (SpO2) and respiration rate (RR) which is standard clinical practice for all patients in the NICU at The Hospital for Sick Children. Diastolic, systolic and mean blood pressures (DBP, SBP and MBP) were also available when collected as part of clinical practice. Currently, these streams were used as part of research into earlier detection of late onset neonatal sepsis. The present invention had access to a combined data set equalling around 115726985 readings has been collected. The complete Artemis deployment occurs in two locations, namely at The Hospital for Sick Children and the UOIT Health Informatics Research (HIR) laboratory and currently supports eight concurrent patients. The following three components are located at The Hospital for Sick Children: (i) the first is responsible for data acquisition from the medical data hub; (ii) the second for online analysis utilizing the InfoSphere Streams Runtime from IBM; and (iii) the third for stream or data persistence utilizing the data integration manager.

Data Persistence occurs to support Online Analysis and Knowledge Extraction. An incremental backup of the data is made each day to a persistence storage mirror located at UOIT and used by the Knowledge Extraction component at UOIT for knowledge discovery. Redeployment occurs after this step which is where new rules are translated to Streams Processing Language (SPL) which is an intermediate language for flexible composition of parallel and distributed data-flow graphs. SFL allows for potential future deployment in the Online Analysis to monitor future patients in real-time.

The second site was situated at The Women and Infants Hospital (WIHRI) in Rhode Island, United States. This site makes use of the SpaceLabs Ultraview SL patient monitors to collect HR, RR, SpO2, Pulse Rate derived from SpO2 sensor and, where collected, continuous DBP, SBP and MBP. The frequency of data coming from this site is in the form of spot readings taken every minute and stored in its raw form at the UOIT. In order to enable data collection from WIHRI, a cloud based environment is setup where data is transported via a secure tunnel to UOIT in the form of HL7 formatted data packets. In this environment, components of the Data Acquisition exist across both sites and all remaining Artemis components are situated at UOIT instead of the hospital. Presently, the data set from WIHRI amounts to around 36546-5 records.

The third site was located at UOIT and comprised 30 second spot readings of retrospective data from The Hospital for Sick Children collected over a time span of two years. The main purpose of this site was to support research for the early detection of multiple clinical diagnoses such as neonatal sepsis and apnoea. As such it contains the Data Persistence, Knowledge Extraction and Redeployment components only.

The Multi-dimensional Distributed Data being collected from the three NICU sites posed some inherent challenges that can prevent normalization of data across the different sites for prior art systems. The main challenge for the present invention was the differences in data frequency that exists from one location to the next. As highlighted earlier, each site generates data differently which creates the lack of consistency between data streams. For instance: (i) the Hospital for Sick Children supplies data at the rate of a reading every 1024 milliseconds; (ii) WIHRI supplies data in the form of spot readings taken every minute; and (iii) UOIT—Retrospective Data which comprises of 30 second spot readings.

Normalization of data may be the first solution that comes to mind when the varied frequencies of data collection are considered. However, the data cannot be normalized because different frequencies are required depending on the type of analysis that needs to be performed. For example, trend analysis temporal abstractions on raw heart rate and respiratory rate data could be performed at spot readings taken every 30 seconds, however, this same technique cannot be applied in the analysis of apnoea because apnoea events can occur between two consecutive 30 second spot readings and hence for example transient falls in blood oxygen saturation of less than 30 seconds would be missed. Thus, it is necessary for the present invention to categorize the abstractions based on similarity as well as frequency in order to effectively run them in a distributed environment.

The Knowledge Extraction component of Artemis implemented the $STDM''_0$ framework. In order to perform temporal abstractions on data, it first processed data from its raw format. The role of the processing agent was to initiate collection of stored physiological and clinical data from external data stores supporting the online analysis or collected via some other means outside of Artemis. $STDM''_0$ was the technique used in the knowledge extraction component of Artemis. Within the first two distributed sites, as detailed herein, the processing agent performed the replication of the data from the Online Analysis Data Persistence component to the Knowledge Extraction Data Persistence component. Once the data had passed from the external collection phase, the processing agent converted the data to the required format if and as necessary and then the data was structured and stored in the clinical data and physiological data tables accessible by the Knowledge Extraction component. After the completion of this phase, the Temporal Agent began to process data in order to create the Temporal Abstractions.

Once the processing agent structured and stored the data in local data stores, the Temporal Agent processed the data using rules defined in the Temporal Rules Table. Temporal Abstractions were created using the temporal rules and the physiological data that has been collected from the monitoring devices.

In this example the Temporal Agent had six functions: (i) it retrieved the physiological data from the physiological data store for each parameter for each patient; (ii) it retrieved relevant abstraction rules from the Temporal Rules Table; (iii) t applied the rules to the physiological data, creating simple abstractions for individual data streams for individual patients; (iv) the created abstractions were stored in the $STDM''_0$ Temporal Data store; (v) complex abstractions were created from the simple abstractions, based on any rules found in the Temporal Rules Table; and (vi) any complex abstractions created were stored in the $STDM''_0$ Temporal Data store.

Data for each patient may consist of multiple time stamped data streams. The time stamped physiological readings were first abstracted individually to simple temporal abstractions and later can be used to create complex abstractions. A typical abstraction may address level shifts i.e. increase, decrease or stable from point x or trends i.e. changes over a set period. Since a time stamped physiological reading for a certain patient can be part of a number of simple abstractions it is computationally efficient to perform both types of abstractions on one data set.

In order to elaborate further, an example of an abstraction run hourly on the respiratory rate (RR) value in a non-distributed setting is relied upon herein. In order to analyze patient data, a 60 minute period for the abstraction was undertaken with the goal of finding when the RR value falls below a specific threshold. The RR value was a value that had a threshold value of 10. The abstractions created were stored in the Temporal Abstraction Table which condenses and adds context to the data.

Once the Temporal Agent has created the abstractions from physiological data, it is common for this data to be used in various clinical research studies. Once the abstractions have been created they are stored locally in the $STDM''_0$ data stores until they are needed for a particular study. When a study is prepared, it will often be necessary to realign the time of abstractions relative to a particular point in time of interest. The Relative Rule table, which specifies a particular alignment of abstractions for a particular study, holds the information about any relative rules that my need to be applied to the abstractions stored in the Temporal Abstraction table.

The Relative Agent realigns the time of abstractions relative to a particular point in time that is of interest by calculating the start and finish times for each abstraction relative to a particular event. If the aim of a research study is to find new trends and patterns that can be indicative of the onset of a condition it will be essential to realign the time of each patient's abstractions relative to the time of the patient being diagnosed with the condition. The abstractions that have been relatively aligned are then stored in the relative temporal data store for further processing. It is also common for different research studies to use the same temporal abstractions which can lead to different re-alignment techniques to be applied to the same data. This is also the reason why every re-aligned Temporal Abstraction is stored in the relative temporal data table specific to the study that has utilized it.

As an example the structure of the Relative Temporal Abstraction table may be operable to analyze patient data, so that a 60 minute period is considered for abstraction with the goal of finding when the HR value falls below a specific threshold, which in this case is a value has a threshold value of 100.

In order to explain the Relative Temporal Abstraction process further, consider the example of Heart Rate Variability (HRV). Once the TAs have been deployed via the TA_Rule table, hourly summaries of HRV are created and stored in the TA table. In this case the event of interest for the TA was the drop in the HR value below 100 within a set period.

To enable the detection of particular patterns of this abstraction at a particular time before the event of interest, re-alignment of the abstractions relative to the time of the event of interest is necessary. The periods of interest would be abstracted by the temporal agent and stored locally at each site. The role of the relative agent is to realign the time of the TAs that have been created previously, with an event of interest, thus giving the relative TAs a start time and end time relative to the point of diagnosis. This will enable the comparison and mining of the abstractions to identify particular behaviours that may indicate the onset of the condition being researched.

The re-aligned Temporal Abstractions form the basis for exploratory and confirmatory data mining, processed by the Functional Agent. The Functional Agent performs data mining tasks used to enable detection of interesting trends and patterns for a particular study. Exploratory data mining is used to analyse the re-aligned Temporal Abstractions across multiple data streams for multiple patients in order to detect new trends and patterns that might present in the data prior to or after the event of interest. The Temporal Abstractions created from the physiological data for each patient that is part of the study must be realigned based on the time of diagnosis as this allows for the search and comparison of all the patients' abstractions regardless of the actual time of the abstractions or the actual time of diagnosis.

Once possible trends and patterns have been discovered, they need to be evaluated by the clinician to enable the creation of a hypothesis. This also allows for the selection of the rules of significance based on the results of the exploratory data mining exercise. The next phase of confirmatory data mining begins with the formulation of the null hypothesis for any results that arouse interest and further investigation.

The Rules Generating Agent utilizes findings made by the Functional Agent to allow for the creation of rules that can be defined in the real-time rules database.

The hypotheses created via the exploratory data mining phase are used by the Rules Generating Agent to create rules that can be stored and utilized by an event stream processor which allows for the application of abstractions on real-time data streams which in turn can help establish these rules in a live analytical system to aid clinicians in real time analysis of data.

Figure 18:
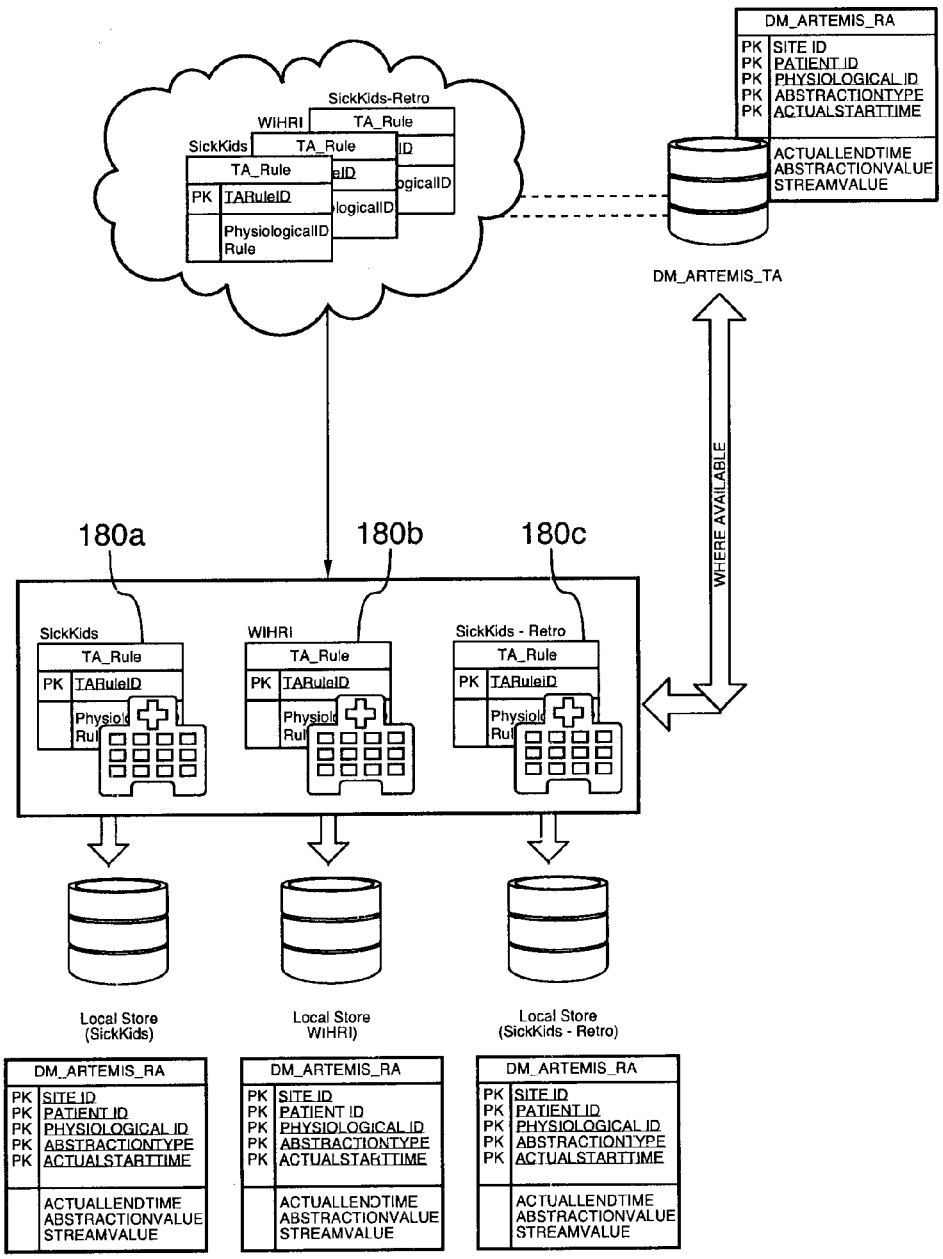
FIG. 18 shows an example of a distributed temporal rules environment operable to manage multiple Temporal Rule tables that may be included in a possible embodiment of the present invention.

One of the limitations of the $STDM''_0$ framework was the notion of only one Temporal Rule table which does not address the area of data distribution and lacks a structure which can support multicenter studies. Another limitation was the lack of clarity on how the Temporal Abstractions will be kept consistent in different sites. In this section, a demonstration of the distributed temporal rules environment is presented, which highlights the management of multiple Temporal Rule tables 180a, 180b, 180c, as shown in FIG. 18. This will also enable the Temporal Abstractions to be consistent across the distributed sites.

As discussed, there are three different multi-dimensional distributed sites which would need to run the Temporal Abstractions. Due to current health care policies and improved patient privacy concerns, it is required that certain types of data exist locally at each site. However, the Temporal Rules do not contain patient identifying information and thus can be decentralized to allow for consistency, better control over the security and better accessibility. In the case of our multi-dimensional distributed environment, there are four main steps to enable the distribution of some of the data: (i) The Temporal Rules exist at a central hub i.e. at UOIT in this scenario. When TA's need to be run, the associated rules are deployed simultaneously for each participating site. The TA rules deployed for each site also contain the SQL query that needs to be run to perform the abstraction at each site as this is supported by the TA_Rule table; (ii) Once the Temporal Rules have been deployed, they are run locally at each of the three sites; (iii) A SITE_ID tag is also attached to each abstraction that is run at these sites in order to allow for comparison of results across sites when needed; and (iv) The results of the Temporal Abstractions are stored locally at each site (DM_ARTEMIS_TA). Where available, these results will also be populated back at the central UOIT store under the DM_ARTEMIS_TA data table.

The present invention may include distributed Temporal Abstraction tables existing at each local multi-dimensional distributed site. In this table, the data shown contains a SITE_ID tag of SK indicating the data belongs to The Hospital of Sick Children. A similar structure is adopted for each distributed site which is identified by their unique SITE_ID i.e. WIHRI being identified as WI and the Sick-Kids Retrospective data being identified as SK30.

As policies regarding the handling of data and its privacy will differ across the multi-dimensional distributed sites; it may be helpful to support the data in a distributed setting. By having regulatory requirements that will govern where the data has to reside and how it can be interacted with it may be possible to manage sensitive patient data properly and at the same time improve patient outcomes at the health facilities.

The Relative Agent may realign the time of abstractions relative to a particular point in time that is of interest. Depending on the study taking place, the temporal abstractions it may be necessary to realign relative to a particular point in time if the behaviour of certain parameters in the time leading up to a diagnosis needs to be studied. The Relative Rule table, which specify a particular alignment of abstractions for a particular study, holds the information about any relative rules that may need to be applied to the abstractions stored in the Temporal Abstraction table.

Figure 19:
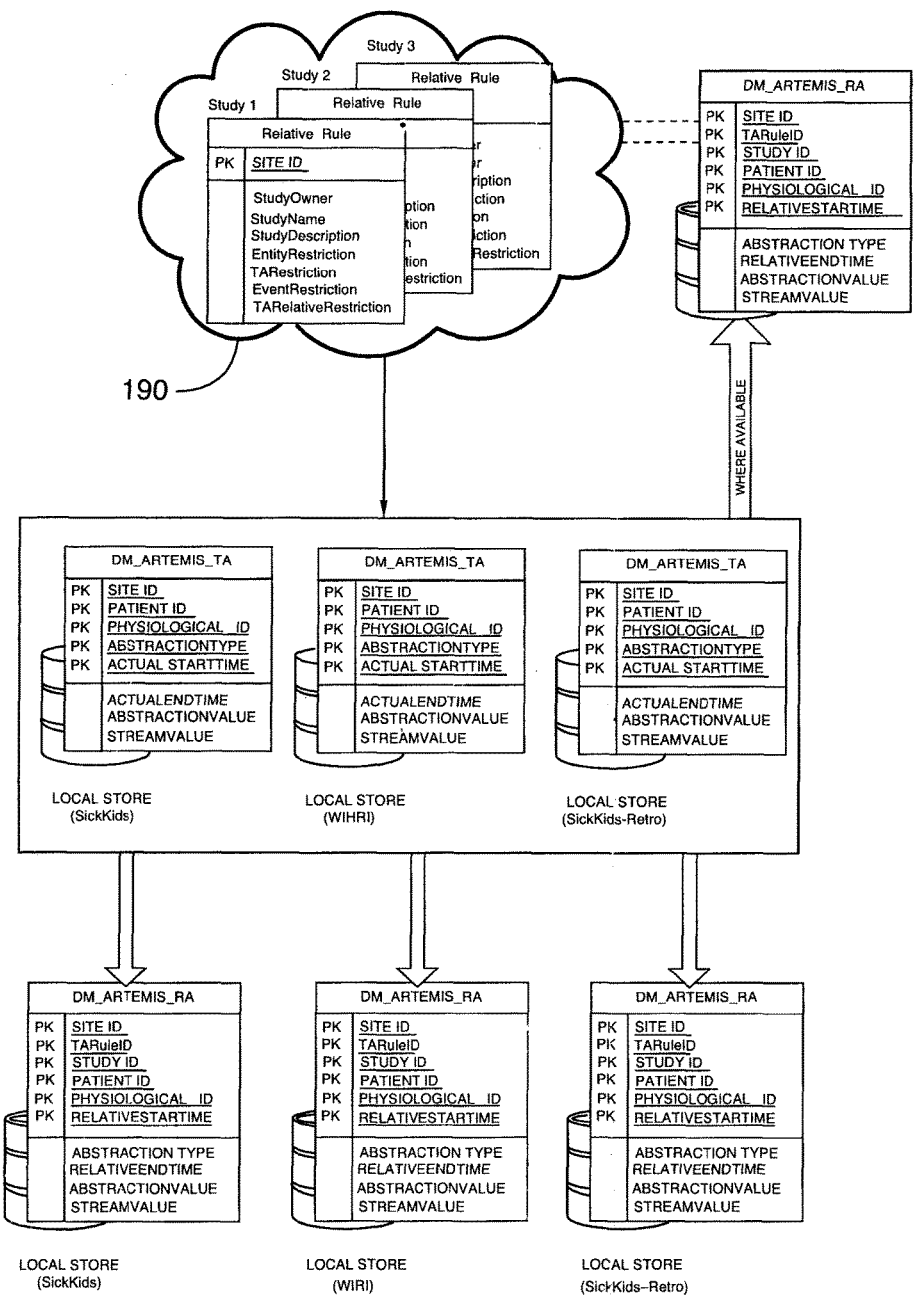
FIG. 19 shows an example of the structure supporting the distribution of Relative Rules that may be included in a possible embodiment of the present invention.

As shown in FIG. 19, the present invention may incorporate a structure supporting the distribution of Relative Rules, for example, such as the distribution of multiple Relative Rules tables through a network, or cloud environment 190. As discussed earlier, the $STDM''_0$ framework presents the notion of only one Relative Rule table which is not suited in multi-centered studies. The following three step approach is taken to enable the distribution of Relative Rules: (i) Relative rules for each study are deployed from the central data store (at UOIT). A separate study table exists for each participating facility and is assigned a unique StudyID; (ii) Once deployed, the Temporal Abstractions table created at each site is accessed locally in order to perform the Relative Alignments needed for the particular study; and (iii) The re-aligned Temporal Abstractions are then stored in the relative temporal data tables specific to the study and the site Each site is identified by a unique StudyID and SITE_ID. Where available, these results will also be populated back at the central UOIT store under the DM_ARTEMIS_RA data table.

A distributed Relative Temporal Abstraction table may include data that contains a SITE_ID tag of WI indicating the data belongs to The Women's and Infants Hospital. The corresponding TARuleID and unique STUDY_ID attributes are also contained in this table. A similar structure is adopted for each distributed site which is identified by their unique SITE_ID i.e. SickKids being identified as SK and the SickKids Retrospective data being identified as SK30.

The realigned temporal abstractions created by the Relative Agent may be further processed by the Functional Agent. In the $STDM^n{}_0$ framework the Functional Agent is responsible for data mining tasks used to enable detection of interesting trends and patterns for a particular study. If the particular study is exploring the possibility of communal patterns or trends being exhibited in the physiological data of neonates in the time period leading up to diagnosis of a particular condition, then the Temporal Abstractions created for each patient that is part of the study must be realigned based on the time of diagnosis. This enables the comparison of all the abstractions for all the patients regardless of the actual time of the abstractions and diagnosis.

The Functional Agent utilizes exploratory data mining to detect new trends and patterns in multiple parameters. These trends and patterns are then evaluated by the clinician or researcher to create a hypothesis. Once the hypothesis is created from trio result of the exploratory data mining, a null hypothesis can be established and tested with confirmatory data mining techniques.

Figure 20:
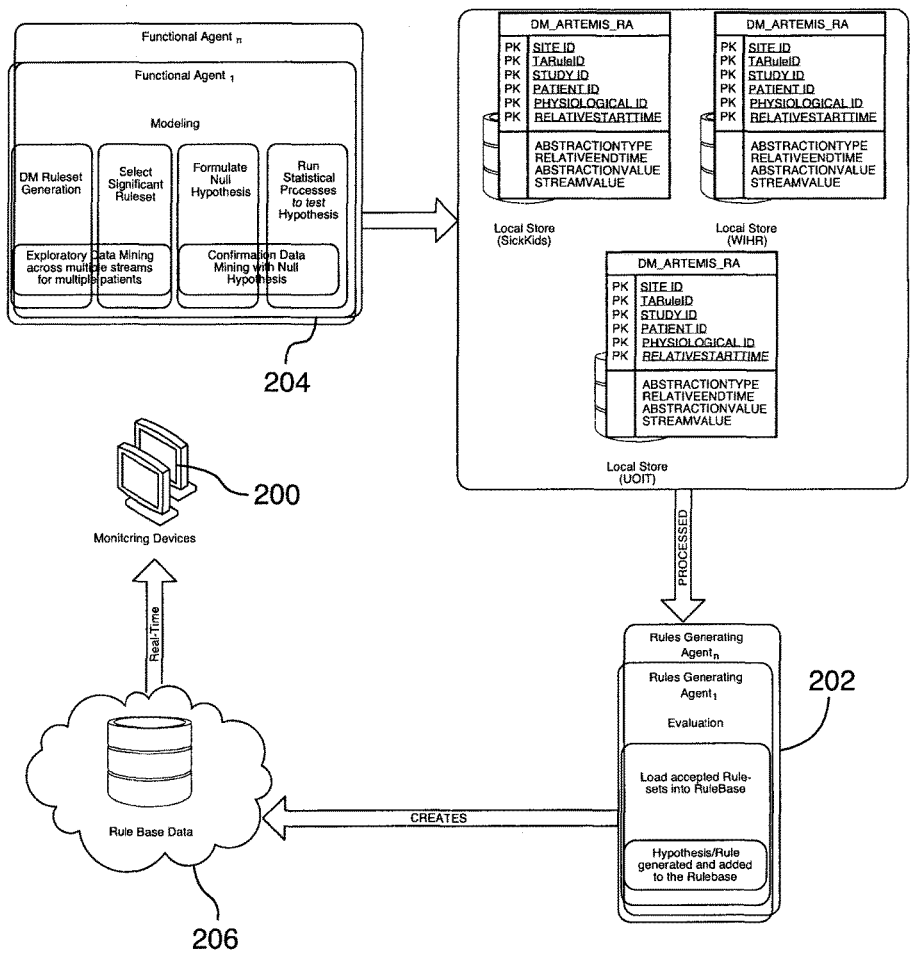
FIG. 20 shows a real-time monitoring system aiding clinicians in early detection of events of interest for better diagnosis and treatment that may be an embodiment of the present invention.

The Rules Generating Agent 202 processes the hypotheses created by the functional agent 204 into appropriate rules that can be stored in the Rule Base 206. The generated rules can further be used in a real-time monitoring system 200 to assist clinicians, for example, such as in the early detection of events of interest for better diagnosis and treatment, as shown in FIG. 20.

II. $STDM^{n+p}{}_0$ Example

A clinical research study example for neonatal apnoea spells demonstrates, an example of an application of an embodiment of the present invention incorporating the $STDM^{n+p}{}_0$ framework. The application results in a multi-dimensional model incorporating gender and gestational age, to define patient characteristic thresholds for these attributes in relation to thresholds set for the detection of apnoea spells and thereby to assist in the support of clinical research within a NICU context.

The objective of the case study is to support the analysis of apnoeic events in neonates. Apnoeic spells are associated with many conditions including late onset neonatal sepsis. Within this research demonstration the following rule for an apnoea spell is utilised: "A lapse in breathing of a neonate for greater than 15 seconds is of clinical relevance (respiratory rate (RR)<25). At all neonatal gestational ages, a fall in peripheral oxygen saturation less than 85% for greater than 20 seconds combined with a HR of less than 108 bpm (100 bpm for male) is also of clinical relevance" (Hein, Ely, & Lofgren, April 1998) (Catley C., Smith, McGregor, James, & Eklund, 2010. To date, as indicated in Chapter 3, HR<100 is the threshold parameter applied (American Heart Association, 2006).

Recent literature states that gender plays a significant role in defining HR differences: newborn male infants have lower baseline HR than newborn females (Nagy & Orvos, 2000) (Krueger, van Oostrom, & Shuster, 2010). These findings suggest that the known gender-related HR differences that are apparent throughout life are also present at the very beginning of life and should be considered when investigating physiological markers for conditions that affect the health and development of the newborn infant (Nagy & Orvos, 2000). The two patient identifiers (Stravroudis, Miller, & Lehmann, 2008) this research proposes for inclusions are that of gestational age end gender to improve accuracy of diagnosis, treatment and critical care of neonates. The inclusion of gender and gestational age sets the stage for the motivation in choosing an apnoea case study to demonstrate the extended patient characteristic framework.

As such, this retrospective research proposes that the physiological stream behaviour thresholds may be more accurate for an individual baby monitored in real-time if they are adjusted based on patient characteristics, such as gender and gestational age. The object of this demonstration is to extend the apnoea spell research to enable the analysis of apnoea spells in association with gender and gestational age. Specifically, through a demonstration of how the extended $STDM^{n+p}{}_0$ framework enables inclusion of patient characteristics within the analysis of the temporal behaviours of the physiological data streams.

Data used within this demonstration was collected and stored through research investment made by the Canada Research Chair program together with an IBM First-of-a-Kind award and resulted in the implementation of the Artemis platform at The Hospital for Sick Children, Toronto, Ontario, Canada. Artemis is a framework to support real-time clinical decision support, together with retrospective clinical research. The goal of the Artemis research project is to provide a flexible platform for the real-time analysis of time series physiological data streams extracted from a range of monitors to detect clinically significant conditions that may adversely affect health outcomes. Artemis supports data collected from multiple physical monitoring devices as well as from the SickKids NICU's Clinical Information Management System (CIMS) and information from the laboratory information system in the hospital. The Artemis platform supports the ingestion and storage of multiple real-time data streams from multiple patients, while analysing for multiple conditions for the purposes of real-time and retrospective analysis, and data-mining (Blount, Ebling, et al., 2010).

The first implementation of Artemis has been utilizing the Philips Intellivue MP70 Neonatal monitors. These devices produce multiple streams of physiological data collected from each patient at a rate of one reading every 1024 ms. This case study demonstration will utilise a reduced data set containing three of these physiological data streams, specifically: electrocardiogram derived RR, $SpO_2$ and HR (ECG-HR).

This chapter will provide an in depth description on how the collected neonatal raw physiological and clinical data moves through the extended $STDM^{n+p}{}_0$ framework, with particular attention paid to the Processing and Temporal Agents that will support defining the patient characteristic clinical temporal rules where new patient characteristic trends and patterns of apnoea will be unveiled. The $STDM^{n+p}{}_0$ framework is presented in FIG. 6-1.

The study of interest, such as apnoea spells in this demonstration, will determine the parameters placed on the data that in turn produces the temporal abstractions collected. The thresholds applied to the different streams and used by this study are as follows:

RR<25 for greater than 15 seconds, peripheral oxygen saturation ($SpO_2$)<85% for greater than 20 seconds combined with a HR of less than 108 bpm (100 bpm for male) for a female neonate of 35 weeks gestational age is all of clinical relevance. These thresholds are applied to their respective streams to create the temporal abstractions that are then stored within the $STDM^{n+p}{}_0$ data storage framework.

The role of the Processing Agent is to initiate access, as well as integration and collection of physiological and clinical data stored from multiple databases. Within this chapter, the mapping of the data from the different de-identified data stores acquired from the NICU will be described in detail and demonstrated. Tasks undertaken by the Processing Agent occur within the Data Acquisition component of the Artemis System Architecture shown in FIG. 6-2.

Artemis is an REB approved collaborative project between SickKids, IBM and UOIT. While the Artemis framework contains components for Data Acquisition, Online Analysis, Data (stream) Persistence, Knowledge Extraction and Redeployment, the demonstration in this example has focused on the Data Persistence and Knowledge Extraction components only. Some details will also be provided on knowledge extracted which then transferred and deployment occurs for real-time use.

Within Artemis there are two copies of Data Persistence: one used to support the Online Analysis and an incremental replica version of the Data Persistence which receives new data each day from the Online Analysis Data Persistence copy. The Knowledge Extraction copy of the Data Persistence is represented by the Data Management layer of the $STDM^{n+p}{}_0$ framework.

From SickKids there are two main Database storage components within the Data Management layer that will be the focus of this example, those being the Clinical Information Management System (CIMS) and physiological data information management (DIM). Both of these sources of data are stored by the 'Static Entity and Event Data' and the 'Entity Stream Data' Database found within the Data Management layer in the framework provided above.

The CIMS database contains all patient source data. Of primary concern for the purposes of this research is the demographic details and physiological measurements at time of birth (gender and gestational age inclusive).

As demonstrated in the above CIMS defined table structures, the Artemis project receives de-identified patient characteristic information in the A_PATIENT table, where the attribute emtek_id has been substituted to attribute artemis_id to maintain anonymity of patients enrolled in the project.

Each preterm infant admitted is registered and clinical data entered into a table and stored within the CIMS database. The gestational age was broken down into weeks plus days.

The DIM database contains all enrolled patients' physiological data, collected via medical attached devices such as the MP70, Each preterm infant enrolled in Artemis has multiple physiological data measurements collected. Each physiological data measurement has a timestamp to the millisecond for every data point collected. The physiological stored files contain the timestamp, patient_id, and the named physiological reading. FIG. 6-4 corresponds to the patient's physiological_id table. Artemis has implemented a horizontal split of the table such that each physiological data reading is on their own.

To enable physiological thresholds to be driven by gender and gestational age, additional attributes will be included in TA tables that will be detailed further in the Temporal Agent section.

The first 'A_PATIENT' table in the above CIMS structure demonstrates how information is drawn from and related to the NICU source data regarding the admitted patient. Primarily of interest in this example is the physiological data initially collected such as dob, gender and gest_age.

In order for the data to pass through to the processing agent the following table structures need to be mapped. Mapping creates the links between the two different databases to enable ease of coupling data elements. Once all mapping of valuable input data is finished, the Processing Agent has completed its tasks in preparation for the data to then be passed on to the Temporal Agent.

The Temporal Agent utilizes data detailing gender and gestational age from the patient table that has been placed in data stores by the Processing Agent. Thresholds are applied to their respective streams to create the temporal abstractions that are then stored within the $STDM^{n+p}{}_0$ data storage framework. The Temporal Agent uses the rules defined in the temporal rules table to create temporal abstractions from the physiological data that has been collected from the MP70 neonatal monitoring equipment used by The Hospital for Sick Children.

The TA rules are executed on data for a predefined time. The example used for this demonstration consists of 20 second sample with one reading every 1024 ns. The data used for this demonstration has three main streams of time-stamped physiological readings which have been abstracted separately into simple temporal abstractions. A particular time-stamped physiological reading for a particular patient can be part of several simple abstractions. The following abstractions are designed to demonstrate that minor adjustments made to abstraction threshold parameters produce significantly different result that may be causal to clinically significant outcomes.

Gestational age has clinically been accepted as a threshold parameter for mean blood pressure for example: "Given a hypothetical newborn baby born 5 weeks premature (35 weeks gestational age), a fall in mean blood pressure less than 35 mm Hg is clinically relevant" (Catley, Smith, McGregor, & Tracy, 2009).

The abstraction rule applied to the MBP data is based on gestational age the first example will a 35 week old therefore using a threshold a follows:

Low=MBP<35, and Normal=MBP>35 would produce TA results as follows:

TABLE 6-7

TA result on MBP of a GA 35 week old neonate

| Patient_ID | Physiological_ID | Abstraction Type | Abstraction Value | ActualStartTime | ActualEndTime |
| --- | --- | --- | --- | --- | --- |
| sample 1 | 4 | Level shift | Low | 20071201 10:59:21.033 | 20091201 10:59:28.201 |
| sample 1 | 4 | Level shift | Normal | 20071201 10:59:29.225 | 20091201 10:59:40.489 |

However, if the same data was retrieved from a neonate with a gestational age of 39 weeks, amending the threshold as follows: Low=MBP<39, and Normal=MBP>39 would produce TA results as follows in Table 6-8:

TABLE 6-8

TA results on MBP of a GA 39 week old neonate

| Patient_ ID | Physiological_ ID | Abstraction Type | Abstraction Value | ActualStartTime | ActualEndTime |
|---|---|---|---|---|---|
| sample 1 | 4 | Level shift | Low | 20071201 10:59:21.033 | 20091201 10:59:34.345 |
| sample 1 | 4 | Level shift | Normal | 20071201 10:59:35.369 | 20091201 10:59:40.489 |

The MBP TA results, as demonstrated, have shown significantly different TA outcomes with only the consideration of gestational age taken into account when defining the threshold rules. This research would like to demonstrate further significant outcomes by incorporating gender into generating the threshold rules defining the algorithms.

The case study is a demonstration of how data collected by the current Artemis pilot could be used through the secondary use of data for new knowledge creation. The following three tables contain a thirty second segment of raw physiological data readings collected every 1024 ms, specifically focusing on RR, $SpO_2$ and HR, that will used throughout the duration of the case study. TAs may be performed on the RR, $SpO_2$ and HR values plotted above and below the threshold for each of the streams under investigation. The threshold is gender dependant and invoked by the integration of the patient table containing the gestational age, which in turn constantly amends TAs created for the different data streams as determined by the rules for that particular data stream stored in the TA_Rule table.

Figure 28:
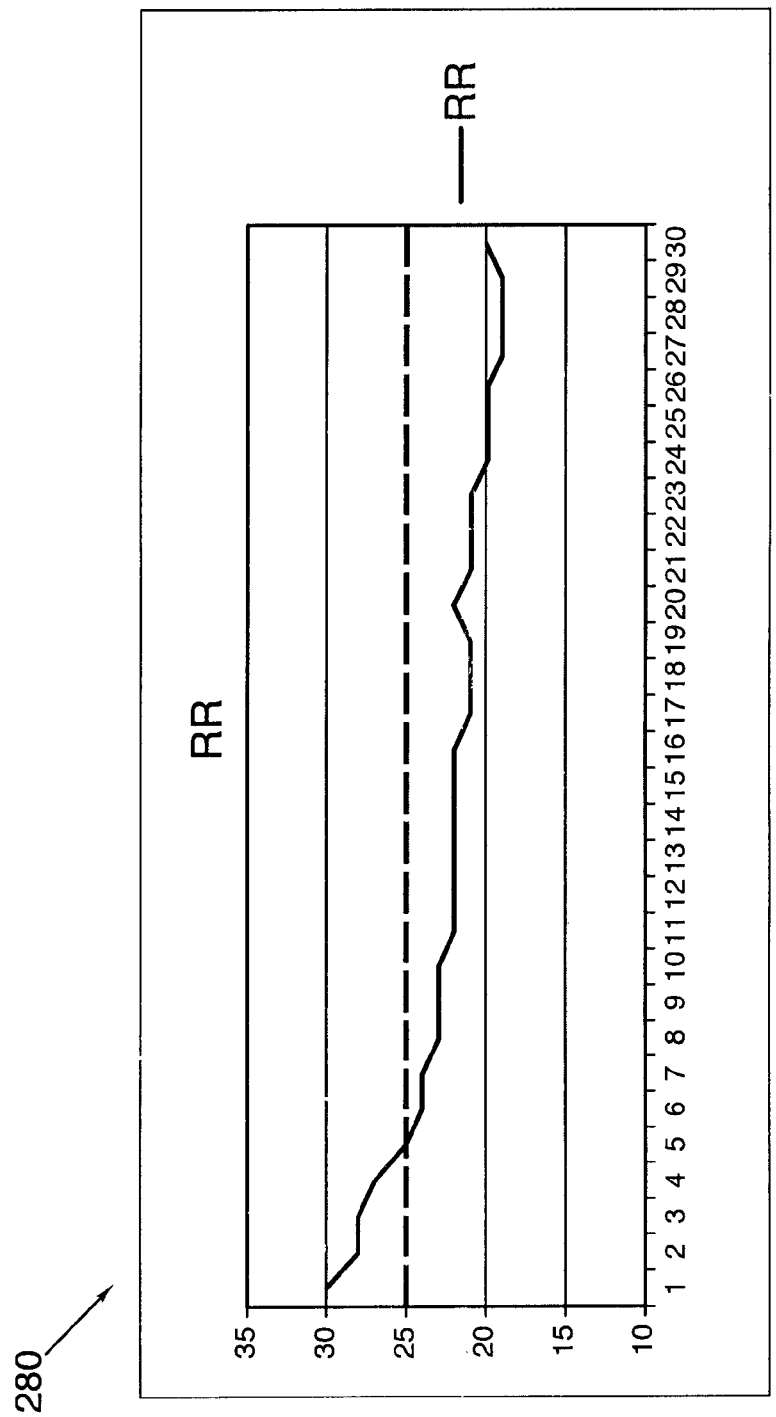
FIG. 28 shows a graphical example of a representation of the values in the table that can be reduced into normal and low abstractions in accordance with an embodiment of the present invention.

Abstractions were conducted on the RR readings, where continuously monitored intervals of RR values at or above a reading of 25 are categorized into 'normal RR' abstraction, and continuous intervals of RR values below 25 are made into a 'low RR' abstraction. As shown in FIG. 28, the values in the table 280 can be reduced into normal and low abstractions.

The rule for this particular abstraction, as presented within this case study, will be:
RR>25
RR<25

Figure 29:
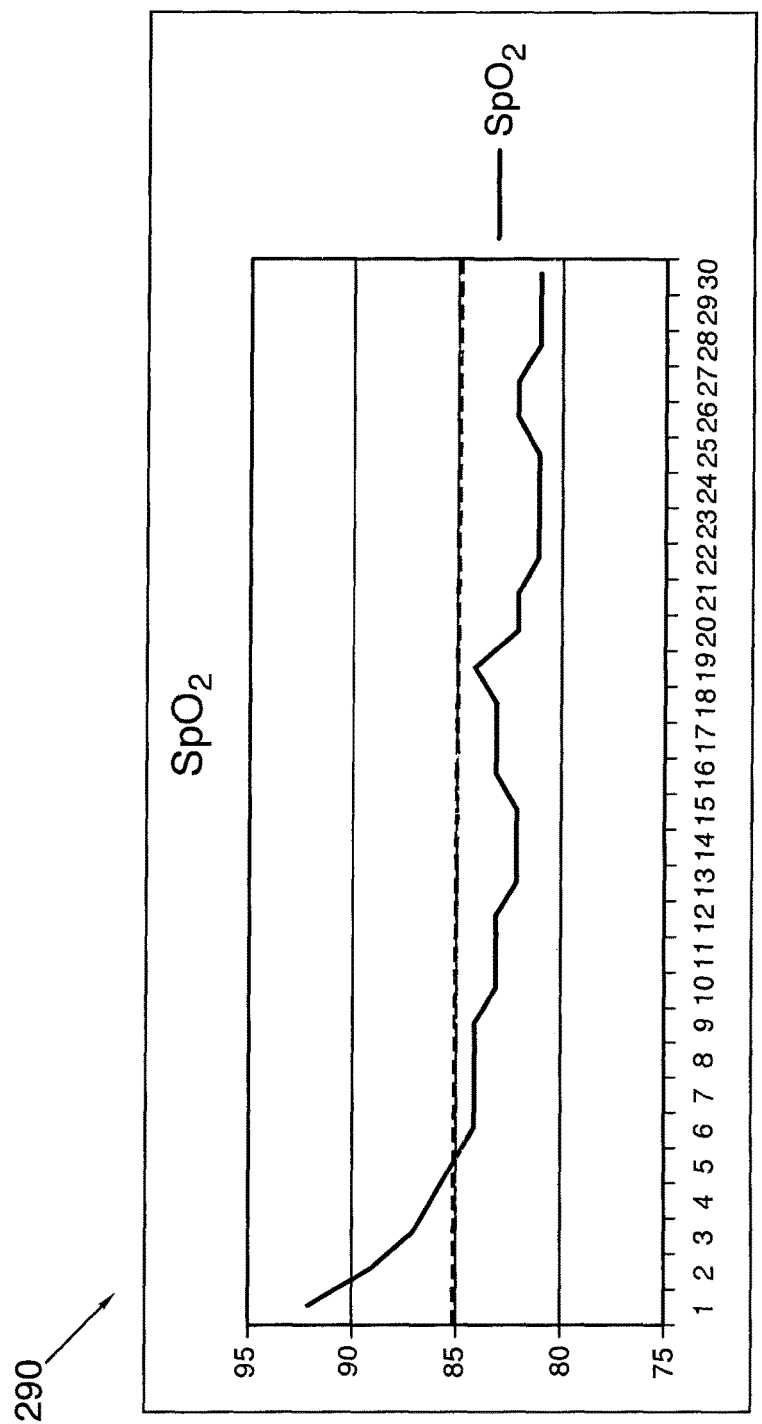
FIG. 29 shows a graphical example of a representation of abstractions that may be conducted on SpO$_2$ in accordance with an embodiment of the present invention.

Abstractions were conducted on the $SpO_2$ readings, where continuous intervals of $SpO_2$ values at or above the 85% are categorized into 'normal' abstractions, and continuous intervals of $SpO_2$ values below 85% are made into a 'low' abstraction. As shown in FIG. 29, the table 290 of the abstractions show that abstractions were created from the $SpO_2$ values against the 85% threshold.

$SpO_2$ threshold of 85% is indicated by the dotted line. $SpO_2$ readings of 85 and above are seen as normal, and readings below 85 can be problematic to the health and future of the neonate. The rule for this particular abstraction, using 85 as a threshold as presented within this case study, will be:
Low=$SpO_2$<85
Normal=$SpO_2$>85

The first 4 readings in FIG. 29 are within the normal range, with a start time at 9.011 seconds and end time at 13.107 seconds, creating a 'normal' abstraction. The next readings are below the 85% threshold and therefore would create a 'low' abstraction, starting at 14.131 seconds and finishing at 38.707 seconds.

Figure 30:
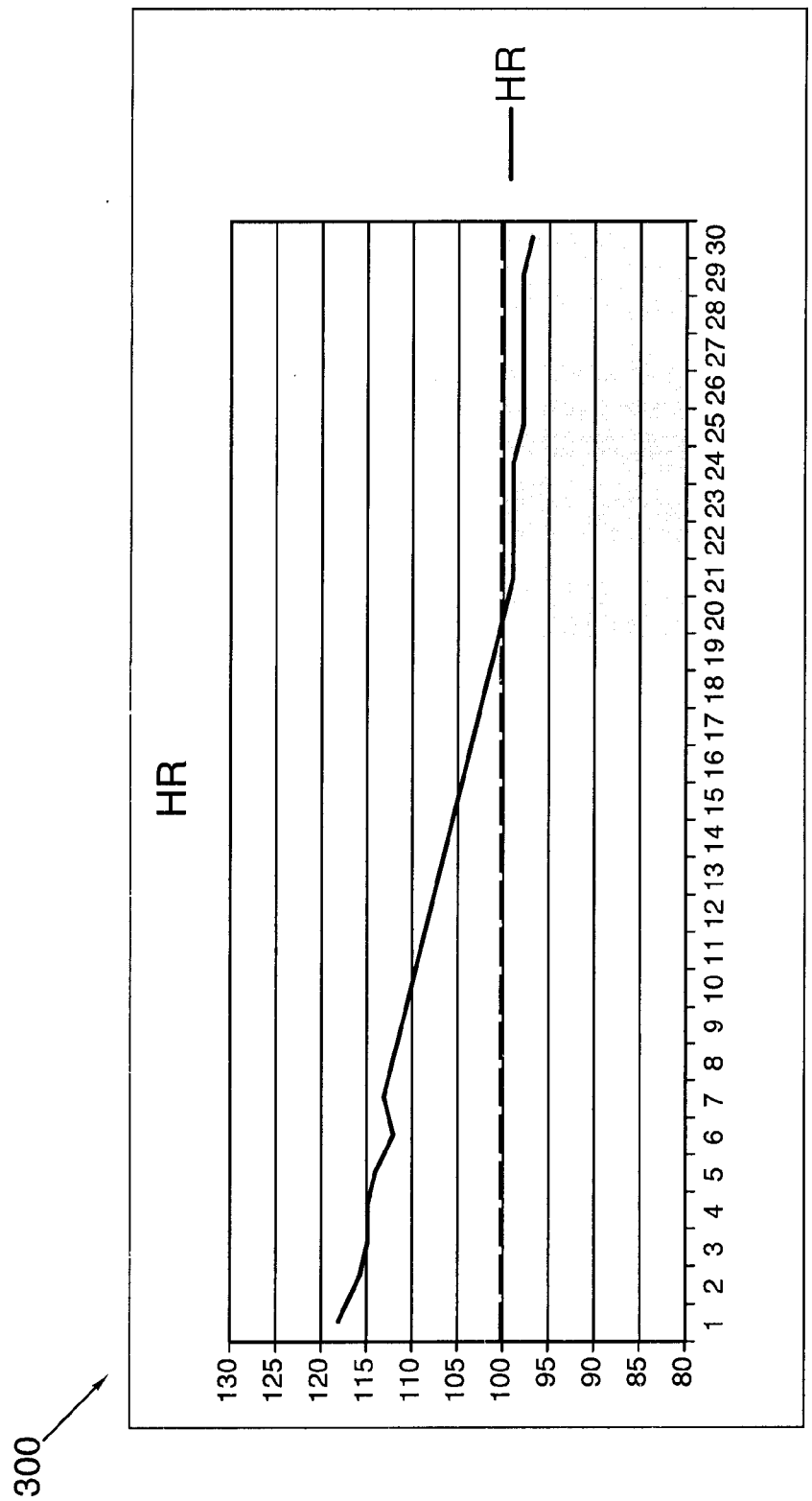
FIG. 30 shows the significance that gender and gestational age can have on HR values showing threshold parameters for a male neonate of 35 weeks GA against the threshold of 100 in accordance with an embodiment of the present invention.

The table 300 shown in FIG. 30, represents the significance that gender and gestational age can have on HR values showing threshold parameters for a male neonate of 35 weeks GA against the threshold of 100 (which is gender and gestational age dependant, male and 35 weeks).

The rule used to abstract the HR for a male neonate of 35 weeks GA parameter is:
Low=HR<100
Normal=HR>100

FIG. 30 shows that the first 19 readings are not within and below the norm al range from the first value until values cross the threshold at time of 28.467 seconds, creating a 'low' abstraction. The readings that followed were all below the 100 bpm threshold and therefore would create a 'low' abstraction, starting at time of 28.467 seconds and finishing at 38.707 seconds.

Figure 31:
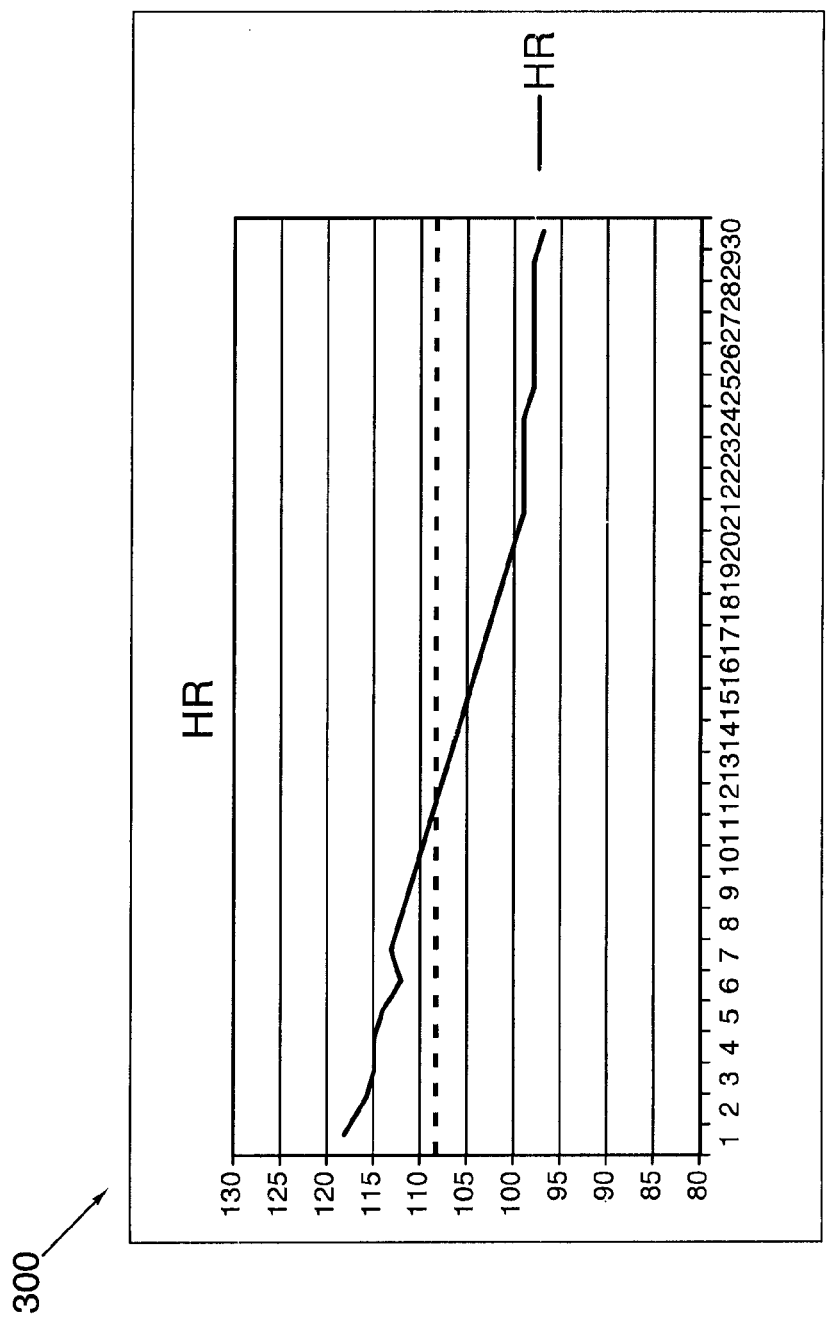
FIG. 31 shows that results can differ significantly when compared to those obtained from a threshold that would be applied to a female neonate of 35 weeks gestational age in accordance with an embodiment of the present invention.
Figure 32:
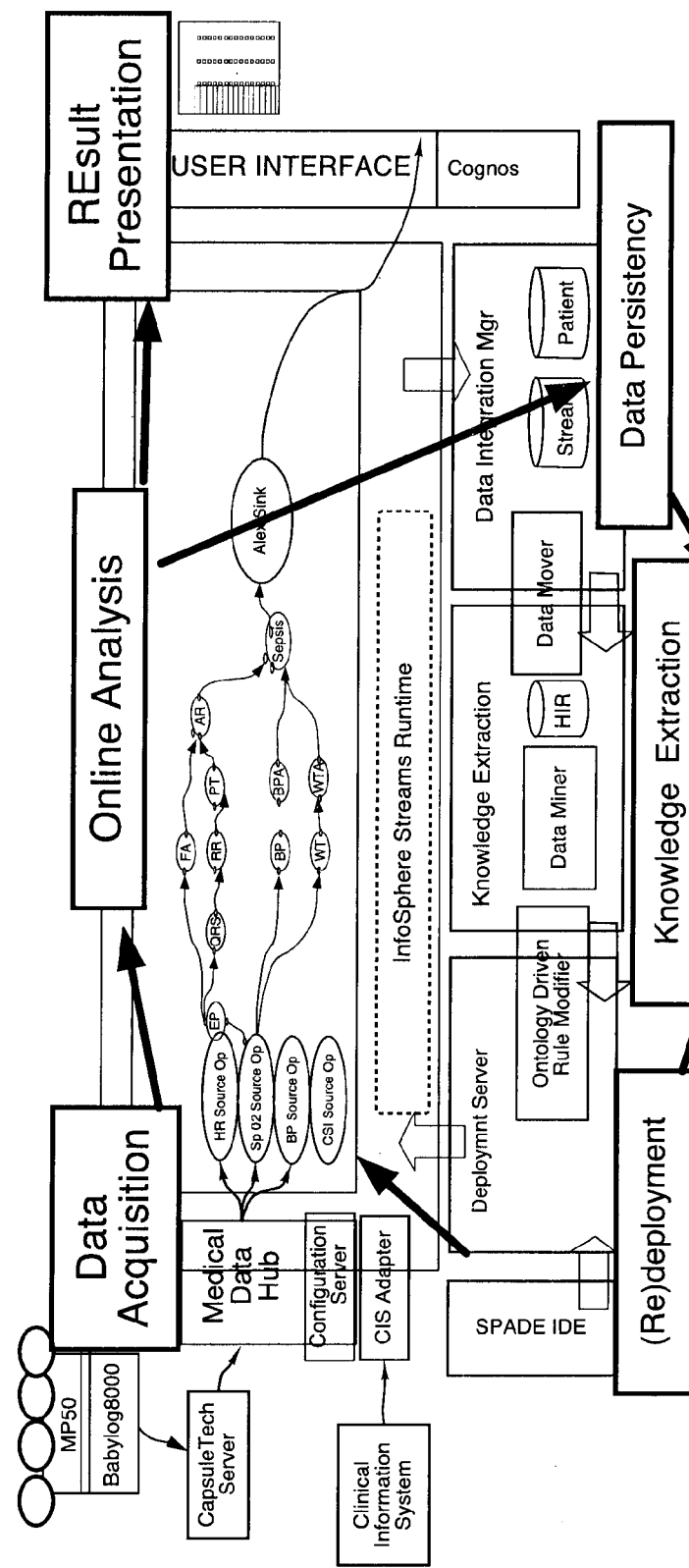
FIG. 32 shows a schematic block diagram of an example system architecture in accordance with an embodiment.

These results differ significantly when compared to those obtained from the threshold that would be applied to a female neonate of 35 weeks gestational age, as shown in FIG. 31.

The rule used to abstract the HR for a female neonate of 35 weeks GA parameter is:
Low=HR<108
Normal=HR>108

As shown in FIG. 31, the first 11 readings are not within and below the normal range from the first value until values cross the threshold at time of 19.251 seconds creating a 'low' abstraction. The readings that followed were all below the 108 bpm threshold and therefore would create a 'low' abstraction, starting at time of 20.275 seconds and finishing at 38.707 seconds.

Temporal abstractions have been shown on three data streams for this case study in ongoing clinical investigation and patient centric research. TAs were created for the different data streams as determined by the temporal abstraction rules.

The next step within the CRISP-TDM methodology is blending abstractions from different data streams to create complex abstractions. Complex abstractions can be created from simple abstractions such as those created above for RR, $SpO_2$ and HR readings. For example, a complex abstraction can be specified when all streams being monitored are below their respective thresholds. The rule that must hold true for this example is RR 15 seconds & $SpO_2$<85 AND HR<108, meaning only intervals where both these conditions are of interest for this particular complex abstraction.

There is one time interval in this sample section of monitoring data that can be used for the complex abstractions where all three parameters have a low abstraction at the same time. These complex abstractions are stored for referencing purposes in the data store.

Every abstraction created from physiological data in the Temporal Agent can be a part of many different clinical research studies. Both simple and complex abstractions are stored until needed in future studies. The Relative Agent in the $STDM^{n+p}{}_0$ Framework does not commence until a particular study is completed. Once a point in time of interest in the study is discovered, it is advantageous to realign the time of abstractions relative to that particular time. The aim of this case study is to find new trends and patterns that can be indicative to the onset of a condition in the physiological parameters of the patient pre diagnosis; therefore, the next phase of the CRISP-TDM framework is to realign the time of abstraction relative to the particular point of interest. The point of interest is the time when the patient was diagnosed with a cot edition across multiple streams of physiological data, in comparison with multiple patients with the same diagnosis.

To enable the detection of particular pattern of these abstractions, at a particular time before diagnosis, realignment of the abstraction relative to the time of diagnosis is necessary. As these abstractions are using absolute time for the start and finish time for each abstraction, it will usually be necessary to give these abstractions start and finish times relative to a particular event that is of interest, such as the time of diagnosis. This will enable the comparison and mining of the abstractions, allowing the distance from time of diagnosis, or another event, to be taken into account.

Clinical researchers looking for cross correlated changes in the temporal physiological data of patients with a particular condition are interested in changes in this temporal data that may be able to indicate the onset of this condition. They need to be able to identify similar patterns or changes in the data that occur at similar times before diagnosis for multiple patients. Using absolute times for the start and end time of abstractions give absolutely no indication of what time this abstraction takes place in relation to the diagnosis.

Abstractions from a patient's $SpO_2$ physiological data stream may include start and end times for each abstraction that are absolute times recorded by the monitoring equipment in use. For example, a first abstraction may have a start time of 20090807 11:04:09.011 and a finish time of 20090807 11:04:13.107. For the purpose of this case study demonstration, if the patient was diagnosed one hour after the start time of the first abstraction recorded, the relative start time for this abstraction would be 00000000_01:00:00.000, exactly one hour before diagnosis. The relative times are created by calculating the difference between the actual times and the time of diagnosis. Trends and patterns in data of interest occur before diagnosis, and therefore data after the diagnosis or event should not be realigned. Table 6-17 contains the relatively aligned temporal abstractions for this particular example.

These patient characteristic physiological data parameters will be stored within tables found in the Temporal and Relative Temporal databases. Although static in nature for the purposes of this demonstration, this is an iterative process that is continually deployed on all data as it is being continuously collected.

The functional agent is the agent that performs the framework data mining tasks. This is where exploratory data mining is used to detect new trends and patterns in multiple parameters to create hypotheses that can be tested via null hypothesis testing through confirmatory mining. This is demonstrated in the case study, wherein trends and patterns are searched for in the temporal abstractions that indicate the onset of apnoea events based on gender and gestational age; such events are also possible cofounders for nosocomial infection.

Considering the case study demonstrated above, further investigations could be placed on the relationship between the various streams of data such as blood oxygen saturation and whether the rule of $SpO_2$ equaling GA holds true for both ganders based on temporal abstractions stored from that study. First exploratory data mining will be exercised to find new hypotheses. An example of such a hypothesis is as follows:

[Breathing pause and {$SpO_2$<87 (Female) or <85 (Male)} and {HR<108 (Female) or <100(Male)}]>15 seconds ⇒ Central Apnoea Once the hypothesis is formulated the null hypothesis can then be created and tested. A null hypothesis would state that there is no difference in the $SpO_2$ readings between female and male infants. If confirmatory mining proves the null hypothesis to be correct, the process is discontinued. However, if confirmatory mining proves the $SpO_2$ readings are in fact different for female and male neonates, the null hypothesis is disproven which warrants further investigations. Clinicians' input and judgment will decide if the hypothesis is sound enough to be adopted as a rule for an intelligent monitoring system or whether further investigation is required. If it is decided that the hypothesis is of sound nature then it is passed on to the rules generating agent.

All rules generated through hypothesis that are created and tested within the Functional Agent and that are clinically approved and adopted by physicians are then stored in the Rule Generating Agent. These rules are available to be used by intelligent monitoring and alerting systems.

A skilled reader will recognize that the $STDM^{n+p}{}_0$ framework of the present invention may be applied to the clinical research subject area of investigation for potential onset indicators for sepsis and other multivariable conditions such as apnoea.

Once thresholds have been derived and hypotheses have been created, tested, and then transformed into rules within this framework, the next stage is enabling the distribution of the framework to interact with the other Artemis locations.

TABLE 6-17

Relative aligned temporal abstractions

| Patient_ID | Gender | GA | Physiological_ID | Abstraction Type | Abstraction Value | ActualStartTime | ActualEndTime |
|---|---|---|---|---|---|---|---|
| Testpatient | F | 35 | 2 | Level shift | Normal | 00000000 01:00:00.000 | 00000000 00:59:55.904 |
| Testpatient | F | 35 | 2 | Level shift | Low | 00000000 00:59:54.880 | 00000000 00:59:30.304 |

The STDM$^{n+o}$ framework will continue to be developed in the Artemis project with a more rich set of actual de-identified data sets from The Hospital for Sick Children, Toronto, Canada, Women and Infants Hospital, Providence, R.I. and Westmead Hospital, Westmead, Australia and multiple other hospitals around the world as the project continues to gain researchers' interest across the globe.

Once the functional agent's exploratory and confirmatory data mining tasks have been deployed and these newly developed patient characteristic hypothesis it is then up to clinicians' judgment whether to adopt the patient characteristic rule(s) for intelligent monitoring systems (CDSS). When considering the development of clinical rules that will be adopted into CDSS it may be important not to adopt a one size fits all approach. This STDM$^{n+p}_0$ framework as presented within this case study chapter has demonstrated a way of creating more individualize patient characteristic approach to neonatal treatment of care.

This framework will provide clinical research within the NICU with the flexibility to adjust physiological data thresholds to meet the changing needs of the developing patient being monitored. These thresholds will be patient characteristic derived and based on trends and patterns discovered with the intent of improving patient outcomes.

III. Further Examples

The present invention can be implemented for data mining outside the field of clinical research. For example, a user may be determining a relationship between shopping patterns for two different types of products, computer network traffic characteristics before a router failure, electricity usage behaviours related to certain weather and sport events through the analysis of smart meter data, car telemetry systems information preceding a certain style of component failure within a vehicle, expected operating behaviours of a certain make and model of vehicle after a certain mileage or age, nuclear power plant operations sensor readings before equipment failure or near failure, share price purchasing trends preceding a certain share price movement behaviour, or distance in time from a company announcement to a certain share prim movement behaviour between companies.

It will be appreciated by those skilled in the art that other variations of the embodiments described herein may also be practiced without departing from the scope of the invention. Other modifications are therefore possible. For example, it may also be possible for software to be loaded onto a computer or an application on a dedicated website or online sales portal. Additionally, it may be possible to integrate the system with lead generation/marketing automation programs to automatically assign persona based on behaviour

What is claimed is:

1. A computer implemented data mining method for controlling mining of data streams in a distributed computing environment configured to provide a distribution layer operable to maintain consistencies across multiple distributed computing systems when performing distributed data processing and analysis, wherein different attributes are associated with each of a plurality data streams, the computer implemented data mining method comprising:
   (a) using a central distribution computer system component to store and maintain consistency of a data mining framework configured to support data mining across the multiple distributed computing systems, the data mining framework including at least:
   (i) a series of temporal rules deployable to a subset of multiple distributed computing systems that are targets for a query; and
   (ii) relative rules adapted for relatively aligning time series multi-dimensional data based on at least one time point of interest, the central distribution computer system being configured for determining a subset of particular temporal rules that are applicable to the time series multi-dimensional data associated to a particular site, based on the different attributes associated with the data streams;
   (b) distributing, from the central distribution computer system to the multiple distributed computing systems, the series of temporal rules and the relative rules to be applied by each distributed computing systems of the multiple distributed computing systems to pre-process the time series multi-dimensional data and to generate new temporally abstracted and relatively aligned time series data representing trends and patterns that include one or more indications of a potential future clinical event;
   (c) collecting, and cleaning at the multiple distributed computing systems, the time series multi-dimensional data, the time series multi-dimensional data obtained through one or more corresponding data streams of the plurality of data streams;
   (d) temporally abstracting, at the multiple distributed computing systems, the collected and cleaned time series multi-dimensional data by accessing and applying the applicable temporal rules so as to generate temporally abstracted time series multi-dimensional data categorized both on similarity and frequency, and relatively aligning the temporally abstracted time series multi-dimensional data based on an at least one time point of interest by accessing and applying the applicable relative rules; and
   (e) collecting the temporally abstracted and relatively aligned time series multi-dimensional data from the multiple distributed computing systems to provide multi-dimensional, temporal, multi-site time series data for use in data mining operations.

2. The method of claim 1, comprising managing the distribution and application of the temporal rules and the relative rules across the multiple distributed computing systems to support the data mining operations across the multiple distributed computing systems in real time or near real time.

3. The method of claim 1, wherein the different attributes may include one or more of: (a) data structure, (b) data collection frequency, or (c) the type of device collecting the data, including at least one of: manufacturer/model, approach of device to data correction or mechanism used for identifying artefacts in signals.

4. The method of claim 3, comprising distributing applicable temporal rules and applicable relative rules based on the attributes associated with the relevant data streams.

5. The method of claim 4, wherein each data stream of the plurality of data streams relates to a corresponding human subject, and wherein the central distribution computer system is configured to (a) initiate creation of simple abstractions for each human subject, store of the simple abstractions locally at each site, and tag the corresponding data streams using site identification data, and (b) initiate creation of complex abstractions using applicable temporal rules and tag the complex abstractions with tagging information defined by the central distribution computer system to enable access for multi-site data mining operations initiated by the central distribution computer system.

6. The method of claim 1, wherein the time series multi-dimensional data is associated with two or more distributed computing systems, and optionally is generated by two or more types of devices, and further is associated with two or more research studies.

7. The method of claim 5, comprising generation of patient monitoring data in real time or near real time for use in connection with one or more patient care systems or patient monitoring systems.

8. The method of claim 5, comprising dynamically defining groups or sub-groups of human subjects, or characteristics associated with such groups or sub-groups, and enabling data mining operations in real time or near real time based on such groups or sub-groups.

9. The method of claim 1, comprising the use of the results of the data mining operations to perform multi-site research data operations across each of the distributed computing systems.

10. The method of claim 1, wherein the time series multi-dimensional data includes physiological data collected by medical devices, wherein at least one of the data structure and frequency of the time series multi-dimensional data collected by the medical devices varies.

11. The method of claim 2, comprising storing the temporal rules and the relative rules in a data store that includes a hierarchy based on simple rules to complex rules.

12. The method of claim 1, wherein at least one data mining operation is based on null hypothesis testing.

13. A data mining computer system for mining data from multiple distributed computing systems, wherein different attributes may be associated with data streams, the system controlling mining of the data streams in a distributed computing environment configured to provide a distribution layer operable to maintain consistencies across the multiple distributed computing systems when performing distributed data processing and analysis, the system comprising:
  (a) a central distribution computer system component configured to store and maintain a data mining framework configured to support data mining across the multiple distributed computing systems, the data mining framework including at least:
    (i) a series of temporal rules deployable to a subset of multiple distributed computing systems that are targets for a query and
    (ii) relative rules adapted for relatively aligning time series multi-dimensional data based on at least one time point of interest, the central distribution computer system being configured for determining a subset of particular temporal rules that are applicable to data associated to a particular site based on the different attributes associated with the data streams;
    the central distribution computer system component configured to distribute to the multiple distributed computing systems the data mining framework, including at least the series of temporal rules and the relative rules to be applied by each distributed computing systems of the multiple distributed computing systems to pre-process the time series multi-dimensional data and to generate new temporally abstracted and relatively aligned time series data representing trends and patterns that include one or more indications of a potential future clinical event;
  (b) one or more devices associated with two or more of the multiple distributed computing systems, the devices collecting data in a plurality of data streams at the multiple distributed computing systems; and
  (c) at least one local computer at each distributed computing system connected to central distribution computer system;
wherein:
  the central distribution computer system is configured to manage the temporal abstraction and relative alignment of the data streams so as to support data mining operations for multi-dimensional data across the multiple sites by:
  accessing, from the at least one local computer, information regarding the different attributes for the data streams;
  providing, to the at least one local computer, the applicable temporal rules and applicable relative rules thereby enabling temporal abstraction of the time series multi-dimensional data to generate temporally abstracted time series multi-dimensional data, and to generate relative alignment of the temporally abstracted time series multi-dimensional data based on an at least one time point of interest in a way that addresses the different attributes; and
  collecting the temporally abstracted and relatively aligned time series multi-dimensional data from the multiple sites by communicating with the at least one local computer and initiating the retrieval and transfer of the temporally abstracted and relatively aligned data based on a data mining request.

14. The data mining computer system of claim 13, wherein the data mining computer system configured to manage distribution and application of the temporal rules and the relative rules across the multiple sites to support data mining operations across the multiple sites in real time or near real time.

15. The data mining computer system of claim 13, wherein the different attributes may include one or more of: (a) data structure, (b) data collection frequency, or (c) the type of device collecting the data (including manufacturer/model, approach of device to data correction or mechanism for identifying artefacts in signals).

16. The data mining computer system of claim 15, wherein the central distribution computer system is configured to distribute applicable temporal rules and applicable relative rules based on the attributes associated with the relevant data streams.

17. The data mining computer system of claim 16, wherein each data stream relates to a human subject, and wherein the central distribution computer system is configured to (a) initiate creation of simple abstractions for each human subject, and storage of the simple abstractions locally at each site, and tagging of the data streams using site identification data, and (b) initiate creation of complex abstractions using the applicable temporal rules and tagging of the complex abstractions with tagging information defined by the central distribution computer system so as to enable access for multi-site data mining operations initiated by the central distribution computer system.

18. The data mining computer system of claim 15, wherein the central computer system is configured to generate patient monitoring data in real time or near real time for use in connection with one or more patient care systems or patient monitoring systems.

19. The data mining computer system of claim 18, wherein each data stream is associated with a particular human subject, and the computer system is configured to dynamically define groups or sub-groups of human subjects, or characteristics associated with such groups or sub-groups, and thereby permit data mining operations in real time or near real time based on such groups or sub-groups.

\* \* \* \* \*